(12) United States Patent
García Collazo et al.

(10) Patent No.: US 11,440,898 B2
(45) Date of Patent: Sep. 13, 2022

(54) ISOQUINOLINE COMPOUNDS, METHODS FOR THEIR PREPARATION, AND THERAPEUTIC USES THEREOF IN CONDITIONS ASSOCIATED WITH THE ALTERATION OF THE ACTIVITY OF BETA GALACTOSIDASE

(71) Applicant: Minoryx Therapeutics S.L., Barcelona (ES)

(72) Inventors: Ana Maria García Collazo, Barcelona (ES); Marc Martinell Pedemonte, Barcelona (ES); Elena Cubero Jordà, Barcelona (ES); Xavier Barril Alonso, Barcelona (ES); Laura Pilar Rodriguez Pascau, Barcelona (ES)

(73) Assignee: Minoryx Therapeutics S.L., Barcelona (ES)

( * ) Notice: Subject to any disclaimer, the term of this patent is extended or adjusted under 35 U.S.C. 154(b) by 600 days.

(21) Appl. No.: 16/473,966

(22) PCT Filed: Dec. 27, 2017

(86) PCT No.: PCT/IB2017/058438
§ 371 (c)(1),
(2) Date: Jun. 26, 2019

(87) PCT Pub. No.: WO2018/122746
PCT Pub. Date: Jul. 5, 2018

(65) Prior Publication Data
US 2020/0071294 A1    Mar. 5, 2020

(30) Foreign Application Priority Data
Dec. 28, 2016   (EP) .................................... 16382660

(51) Int. Cl.
| | | |
|---|---|---|
| *C07D 401/12* | (2006.01) | |
| *A61K 31/472* | (2006.01) | |
| *A61K 31/4725* | (2006.01) | |
| *A61K 31/5377* | (2006.01) | |
| *A61K 38/47* | (2006.01) | |
| *A61K 45/06* | (2006.01) | |

(Continued)

(52) U.S. Cl.
CPC .......... *C07D 401/12* (2013.01); *A61K 31/472* (2013.01); *A61K 31/4725* (2013.01); *A61K 31/5377* (2013.01); *A61K 38/47* (2013.01); *A61K 45/06* (2013.01); *C07D 217/22* (2013.01); *C07D 401/14* (2013.01); *C07D 405/12* (2013.01); *C07D 405/14* (2013.01); *C07D 417/14* (2013.01)

(58) Field of Classification Search
CPC combination set(s) only.
See application file for complete search history.

(56) References Cited

U.S. PATENT DOCUMENTS

| | | |
|---|---|---|
| 2005/0054850 A1 | 3/2005 | Wu et al. |
| 2005/0165032 A1 | 7/2005 | Norman et al. |

(Continued)

FOREIGN PATENT DOCUMENTS

| | | |
|---|---|---|
| DE | 19740785 A1 | 8/1998 |
| EP | 1433776 A1 | 6/2004 |

(Continued)

OTHER PUBLICATIONS

Caciotti, A., et al., "GM1 gangliosidosis and Morquio B disease: an update on genetic alterations and clinical findings," *Biochim Biophys Acta* 1812(7): 782-790, Elsevier, Netherlands (2011).

(Continued)

*Primary Examiner* — Heidi Reese
(74) *Attorney, Agent, or Firm* — Sterne, Kessler, Goldstein & Fox P.L.L.C.

(57) ABSTRACT

The application is directed to compounds of formula (I):(I), and formula (IA):(IA) and their salts and solvates, wherein $R^1$, $R^2$, $R^3$, $R^4$, $R^5$, n, $A^1$, $A^2$, $A^3$, and Y are as set forth in the specification, as well as to a method for their preparation, pharmaceutical compositions comprising the same, and use thereof for the treatment and/or prevention of conditions associated with the alteration of the activity of β-galactosidase, specially galactosidase beta-1 or GLB 1, including GM 1 gangliosidoses and Morquio syndrome, type B.

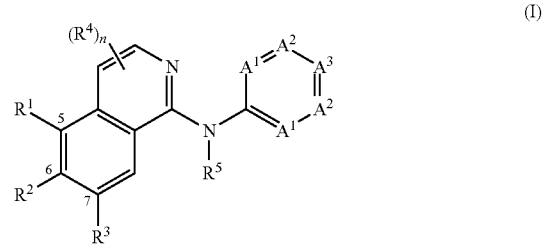

(I)

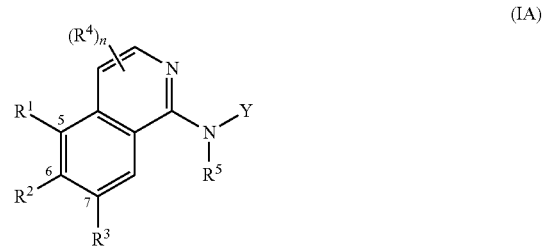

(IA)

23 Claims, 4 Drawing Sheets

(51) Int. Cl.
*C07D 217/22* (2006.01)
*C07D 401/14* (2006.01)
*C07D 405/12* (2006.01)
*C07D 405/14* (2006.01)
*C07D 417/14* (2006.01)

(56) References Cited

U.S. PATENT DOCUMENTS

| | | |
|---|---|---|
| 2009/0053192 A1 | 2/2009 | Millan et al. |
| 2010/0160355 A1 | 6/2010 | Degoey et al. |
| 2016/0207933 A1 | 6/2016 | Bourque et al. |

FOREIGN PATENT DOCUMENTS

| | | |
|---|---|---|
| WO | WO 9724328 A1 | 7/1997 |
| WO | WO 0064888 A1 | 11/2000 |
| WO | WO 0158899 A1 | 8/2001 |
| WO | WO 2004078114 A2 | 9/2004 |
| WO | WO 2005085227 A1 | 9/2005 |
| WO | WO 2005086904 A2 | 9/2005 |
| WO | WO 2006053109 A1 | 5/2006 |
| WO | WO 2006058905 A1 | 6/2006 |
| WO | WO 2006076644 A2 | 7/2006 |
| WO | WO 2006100586 A1 | 9/2006 |
| WO | WO 2007022380 A2 | 2/2007 |
| WO | WO 2007056221 A2 | 5/2007 |
| WO | WO 2007059299 A1 | 5/2007 |
| WO | WO 2008008234 A1 | 1/2008 |
| WO | WO 2008017710 A1 | 2/2008 |
| WO | WO 2008034575 A1 | 3/2008 |
| WO | WO 2009049421 A1 | 4/2009 |
| WO | WO 2009064959 A1 | 5/2009 |
| WO | WO 2010046517 A1 | 4/2010 |
| WO | WO 2010075376 A2 | 7/2010 |
| WO | WO 2011049737 A1 | 4/2011 |
| WO | WO 2012068589 A2 | 5/2012 |
| WO | WO 2014120995 A2 | 8/2014 |
| WO | WO 2015014900 A1 | 2/2015 |
| WO | WO 2015069594 A1 | 5/2015 |
| WO | WO 2015076800 A1 | 5/2015 |
| WO | WO 2015162516 A1 | 10/2015 |
| WO | WO 2016022645 A1 | 2/2016 |
| WO | WO 2016120808 A1 | 8/2016 |

OTHER PUBLICATIONS

International Search Report and Written Opinion for International Application No. PCT/IB2017/058438, European Patent Office, Netherlands, dated Mar. 13, 2018, 10 pages.

Ogawa, S., et al., "Chemical Modification of the β-Glucocerebrosidase Inhibitor *N*-Octyl-β-valienamine: Synthesis and Biological Evaluation of 4-Epimeric and 4-*O*-(β-D-Galactopyranosyl) Derivatives," *Bioorganic & Medical Chemistry* 10(6): 1967-1972, Elsevier, Netherlands (2002).

Suzuki, Y., "Visions and Reflections (Minireview), Chemical chaperone therapy for $G_{m1}$-gangliosidosis," *Cell. Mol. Life Sci.* 65: 351-353, Birkhauser Verlag, Switzerland (2008).

English language abstract of WO 2010046517-A1 (FP5), Espacenet, European Patent Office, Germany, accessed Apr. 6, 2020, 2 pages.

English language abstract of DE 19740785-A1 (FP9), Espacenet, European Patent Office, Germany, accessed Apr. 10, 2020, 3 page.

ISOQUINOLINE COMPOUNDS, METHODS FOR THEIR PREPARATION, AND THERAPEUTIC USES THEREOF IN CONDITIONS ASSOCIATED WITH THE ALTERATION OF THE ACTIVITY OF BETA GALACTOSIDASE

CROSS-REFERENCE TO RELATED APPLICATION

This application claims priority to European Patent Application No. EP16382660.5, filed on Dec. 28, 2016, the entirety of which is incorporated by reference herein.

FIELD OF THE DISCLOSURE

The present disclosure is related to isoquinoline compounds, with new processes for their preparation, and to the use thereof in the treatment and/or prevention of conditions associated with the alteration of the activity of beta galactosidase, specially galactosidase beta-1 or GLB1, including GM1 gangliosidoses and Morquio syndrome, type B.

BACKGROUND OF THE DISCLOSURE

GM1 gangliosidosis and Morquio B syndrome, both arising from beta-galactosidase (GLB1) deficiency, are very rare lysosomal storage diseases with an incidence of about 1:100,000-1:200,000 live births worldwide (Caciotti A. et al., *Biochim Biophys Acta* 1812(7):782-890 (July 2011)). Said conditions associated with GLB1 are known to be caused by a deficiency of the enzyme β-galactosidase due to mutations in the GLB1 gene.

β-Galactosidase cleaves β-galactose from different substrates, and deficiencies in its activity cause said substrates (i.e., gangliosides, and oligosaccharides carrying terminal β-linked galactose, such as ganglioside GM1 and glycosaminoglycans such as keratin sulfate) to accumulate in patients suffering from conditions associated with GLB1 activity such as GM1 gangliosidosis and Morquio B syndrome.

Suzuki et al. (*Cell. Mol. Life Sci.* 65:351-353 (2008)) reported that the mutations of the GLB1 gene result in an unstable mutant β-galactosidase enzyme protein with normal or near-normal biological activity. The mutant enzyme protein seems to be unstable at neutral pH in the endoplasmic reticulum (ER)/Golgi apparatus, and rapidly degraded because of inappropriate molecular folding and this is the reason for its impaired activity. The authors also reported that the use of a competitive inhibitor binding to misfolded mutant protein as a molecular chaperone (i.e. a small molecule that interacts with a misfolded protein to achieve a recovery on its activity) resulted in the formation of a stable molecular complex at neutral pH. The protein-chaperone complex was safely transported to the lysosome, where it dissociated under the acidic conditions. In this way the mutant enzyme remained stabilized, and its catalytic function was enhanced.

Several patents and publications have since then explored the use of chaperones to treat conditions associated with the alteration of the activity of GLB1: WO 2008/034575 A, WO 2006/100586 A, WO 2009/049421 A, WO 2010/046517, EP 1 433 776 A and Ogawa S. et al., *Bioorg. Med. Chem.* 10(6), 1967-1972 (2002).

Therefore, small molecules capable of binding allosterically or competitively to mutated β-galactosidase enzyme thereby stabilizing the enzyme against degradation (chaperones) constitute an important therapeutic target in conditions associated with the alteration of the activity of beta galactosidase, specially galactosidase beta-1 or GLB1.

It has been surprisingly found that compounds of general formula (I) are capable of binding to beta galactosidase thereby stabilizing the enzyme against denaturation.

BRIEF SUMMARY OF THE DISCLOSURE

In one aspect, the present disclosure provides compounds represented by formulae (I) and (IA), and the salts and solvates thereof, collectively referred to herein as "Compounds of the Disclosure" (each individually referred to hereinafter as a "Compound of the Disclosure").

In one aspect, the present disclosure provides compounds of formula (I),

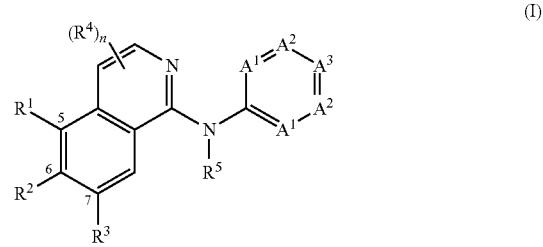

and salts and solvates thereof (for example pharmaceutically acceptable salts and solvates thereof), wherein $R^1$, $R^2$, $R^3$, $R^4$, $R^5$, $A^1$, $A^2$, $A^3$, and n are defined as follows:

each of $A^1$ is independently selected from the group consisting of nitrogen and CH; and each of $A^2$ and $A^3$ is independently selected from the group consisting of nitrogen, CH, and $C(R^6)$; wherein each $A^1$ is CH and each of $A^2$ and $A^3$ is independently selected from CH and $C(R^6)$, provided that only one of $A^2$ and $A^3$ is $C(R^6)$; or exactly one of $A^2$ and $A^3$ is $C(R^6)$ and no less than one and no more than two of $A^1$, $A^2$, and $A^3$ are nitrogen;

$R^1$, $R^2$, and $R^3$ are each independently selected from the group consisting of hydrogen, halogen, —CN, —ORb, and —$C_{1-4}$ alkyl, wherein said —$C_{1-4}$ alkyl group is optionally substituted by 1, 2 or 3 independently selected halogen atoms, with the proviso that at least one $R^1$, $R^2$, and $R^3$ is other than hydrogen;

$R^6$ is —B—NH—$R^7$;

B is —CO— or —$SO_2$—;

each $R^4$ is independently selected from the group consisting of halogen, —$C_{1-4}$ alkyl, —$C_{1-4}$ alkoxy, —CN and hydroxy;

n has a value selected from 0, 1 or 2;

$R^5$ is hydrogen or —$C_{1-4}$ alkyl;

$R^7$ is selected from the group consisting of —$C_{1-4}$ alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, (5- to 10-membered)-$C_{1-9}$ heteroaryl, —$C_{1-4}$ alkyl-(5- to 10-membered)-$C_{1-9}$ heteroaryl, (5- to 10-membered)-$C_{1-9}$ heterocyclyl, and —$C_{1-4}$ alkyl-(5- to 10-membered)-$C_{1-9}$ heterocyclyl; said alkyl, cycloalkyl, alkylcycloalkyl, aryl, alkylaryl, heteroaryl, alkylheteroaryl, heterocyclyl, and alkylheterocyclyl groups optionally being substituted with 1, 2, or 3 groups independently selected from the group consisting of halogen, hydroxy, —CN, —ORb, —SRb, —N(Rb)$_2$, —$C_{1-4}$alkyl optionally substituted with 1, 2, or 3 halogen atoms, optionally substituted $C_{6-10}$ aryl, optionally substituted (5- to 10-membered)-$C_{1-9}$ heteroaryl, and (5- to 10-membered)-$C_{1-9}$ heterocyclyl; said cycloalkyl, alkylcycloalkyl, aryl, alkylaryl, heteroaryl, alkylheteroaryl, heterocyclyl, and alkylheterocyclyl is optionally fused to a further (second) ring, and each Rb is independently hydrogen, —$C_{1-4}$ alkyl, —$C_{3-10}$ cycloalkyl, or (5- to 10-membered)-$C_{1-9}$ heterocyclyl; said alkyl, cycloalkyl or heterocyclyl groups optionally being substituted by 1, 2 or 3 fluorine atoms.

In another aspect, the present disclosure provides compounds of formula (IA),

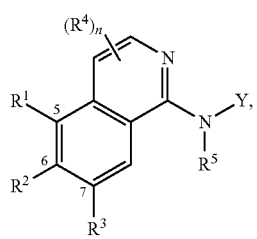

(IA)

and solvates and salts thereof, wherein $R^1$, $R^2$, $R^3$, $R^4$, $R^5$, n, and Y are as defined below.

In another aspect, the present disclosure provides a pharmaceutical composition comprising a compound of any one of formulae (I) and (IA), or a pharmaceutically acceptable salt or solvate thereof, as defined herein and at least one pharmaceutically acceptable excipient.

In another aspect, the present disclosure provides compounds of any one of formulae (I) and (IA) as defined herein, or pharmaceutically acceptable salts or solvates thereof, for use in the prevention or treatment of a condition associated with the alteration of the activity of GLB1.

In another aspect, the present disclosure provides use of a compound of any one of formulae (I) and (IA), or a pharmaceutically acceptable salt or solvate thereof, as defined herein, in the preparation of a medicament for the prevention or treatment of a condition associated with the alteration of the activity of GLB1.

In another aspect, the present disclosure provides a method for the prevention or treatment of a condition associated with the alteration of the activity of GLB1, which comprises the administration to a patient needing such prevention or treatment, of a therapeutically effective amount of at least one compound of any one of formulae (I) and (IA), or a pharmaceutically acceptable salt or solvate thereof, as defined herein.

In another aspect, the present disclosure provides a method of treating or preventing a condition associated with the alteration of the activity of GLB1 in a patient, comprising administering to the patient in need thereof an effective amount of a Compound of the Disclosure, or a pharmaceutically acceptable salt or solvate thereof.

In another aspect, the present disclosure provides a method of treating GM1 gangliosidosis or Morquio B syndrome in a patient, comprising administering to the patient in need thereof an effective amount of a Compound of the Disclosure, or a pharmaceutically acceptable salt or solvate thereof.

In another aspect, the present method of treating GM1 ganglisidosis or Morquio B syndrome in a patient further comprises administering to the patient an effective amount of an enzyme for enzyme replacement therapy. In one embodiment, the enzyme is β-galactosidase or an analog thereof.

In another aspect, the method further comprises administering to the patient a small molecule chaperone. In one embodiment, the small molecule chaperone binds competitively to an enzyme. In another embodiment, the small molecule chaperone is selected from the group consisting of iminoalditols, iminosugars, aminosugars, thiophenylglycosides, glycosidase, sulfatase, glycosyl transferase, phosphatase, and peptidase inhibitors.

In another aspect, the present disclosure provides a method of increasing β-galactosidase activity in a patient in need thereof, comprising administering to the patient an effective amount of a Compound of the Disclosure, or a pharmaceutically acceptable salt or solvate thereof.

Other aspects and advantages of the disclosure will be readily apparent from the following detailed description of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the disclosure as claimed.

DETAILED DESCRIPTION OF THE DISCLOSURE

Figure 1A:
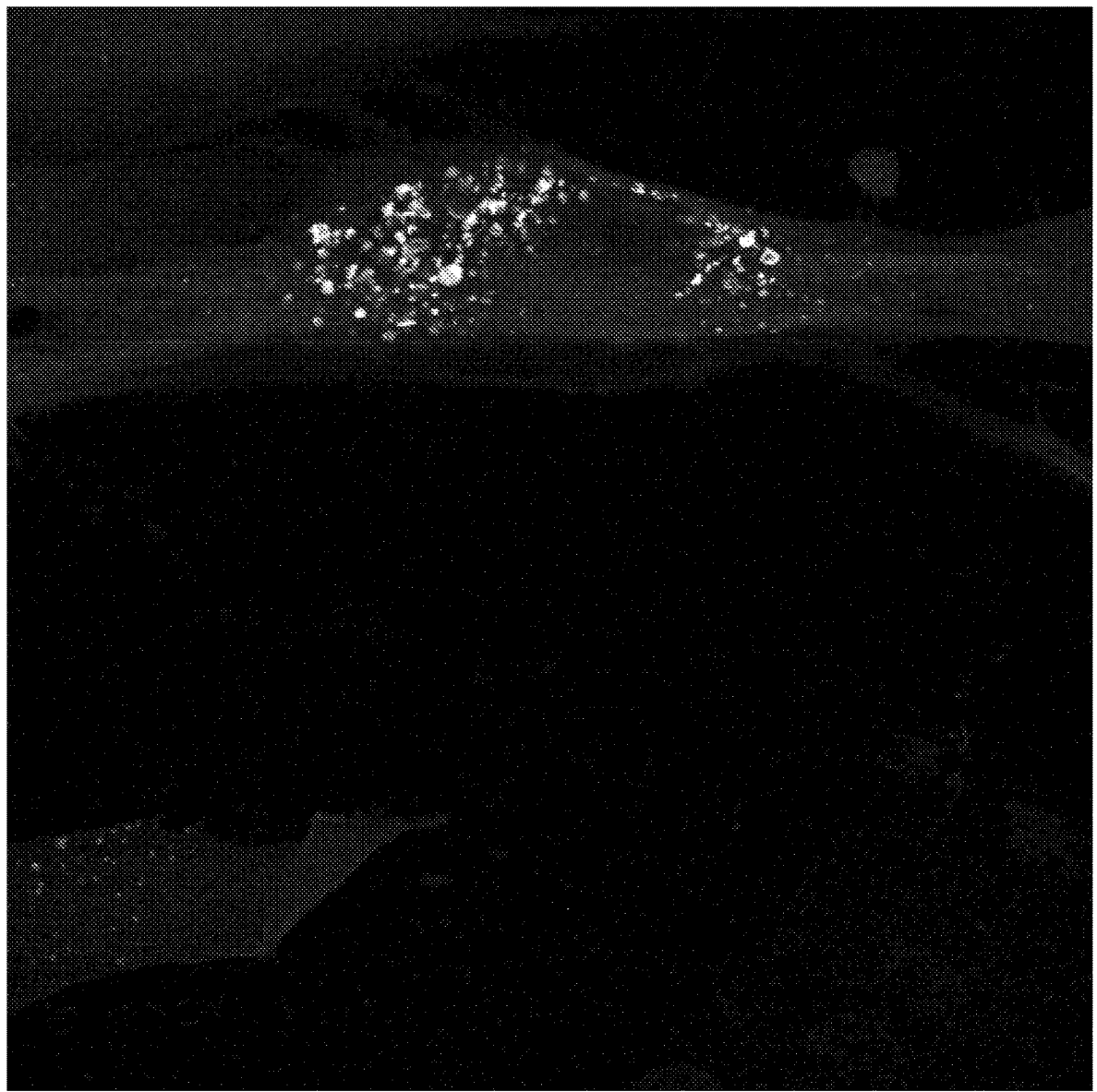
FIGS. 1A and 1B show accumulation of GM1 ganglioside in GM11473 untreated cells.

One aspect of the disclosure is based on the use of Compounds of the Disclosure for binding allosterically to mutated β-galactosidase enzyme and, thereby, stabilizing the enzyme against denaturation. In view of this property, Compounds of the Disclosure are useful for preventing or treating conditions associated with the alteration of the activity of β-galactosidase, and especially galactosidase beta-1 or GLB1, including GM1 gangliosidoses and Morquio syndrome, type B.

In one aspect, the present disclosure provides compounds of formula (I),

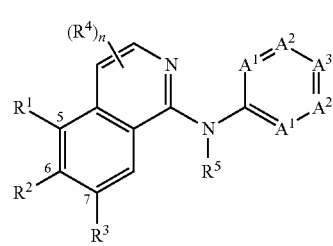

(I)

and salts and solvates thereof (for example pharmaceutically acceptable salts and solvates thereof), wherein $R^1$, $R^2$, $R^3$, $R^4$, $R^5$, $A^1$, $A^2$, $A^3$, and n are as defined below:

each of $A^1$ is independently selected from the group consisting of nitrogen and CH; and each of $A^2$ and $A^3$ is independently selected from the group consisting of nitrogen, CH, and $C(R^6)$; wherein
each $A^1$ is CH and each of $A^2$ and $A^3$ is independently selected from CH and $C(R^6)$, provided that only one of $A^2$ and $A^3$ is $C(R^6)$; or
exactly one of $A^2$ and $A^3$ is $C(R^6)$ and no less than one and no more than two of $A^1$, $A^2$, and $A^3$ are nitrogen;
$R^1$, $R^2$, and $R^3$ are each independently selected from the group consisting of hydrogen, halogen, —CN, —ORb, and —$C_{1-4}$ alkyl, wherein said —$C_{1-4}$ alkyl group is optionally substituted by 1, 2 or 3 independently selected halogen atoms, with the proviso that at least one $R^1$, $R^2$, and $R^3$ is other than hydrogen;
$R^6$ is —B—NH—$R^7$;
B is —CO— or —$SO_2$—;
each $R^4$ is independent selected from the group consisting of halogen, —$C_{1-4}$ alkyl, —$C_{1-4}$ alkoxy, —CN and hydroxy;
n has a value selected from 0, 1 or 2;
$R^5$ is hydrogen or —$C_{1-4}$ alkyl;
$R^7$ is selected from the group consisting of —$C_{1-4}$ alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, (5- to 10-membered)-$C_{1-9}$ heteroaryl, —$C_{1-4}$ alkyl-(5- to 10-membered)-$C_{1-9}$ heteroaryl, (5- to 10-membered)-$C_{1-9}$ heterocyclyl, and —$C_{1-4}$ alkyl-(5- to 10-membered)-$C_{1-9}$ heterocyclyl; said alkyl, cycloalkyl, alkylcycloalkyl, aryl, alkylaryl, heteroaryl, alkylheteroaryl, heterocyclyl, and alkylheterocyclyl groups optionally being substituted with 1, 2, or 3 groups independently selected from the group consisting of halogen, hydroxy, —CN, —ORb, —SRb, —N(Rb)$_2$, —$C_{1-4}$alkyl optionally substituted with 1, 2, or 3 halogen atoms, optionally substituted $C_{6-10}$ aryl, optionally substituted (5- to 10-membered)-$C_{1-9}$ heteroaryl, and (5- to 10-membered)-$C_{1-9}$ heterocyclyl; said cycloalkyl, alkylcycloalkyl, aryl, alkylaryl, heteroaryl, alkylheteroaryl, heterocyclyl, and alkylheterocyclyl is optionally fused to a further (second) ring, and
each Rb is independently hydrogen, —$C_{1-4}$ alkyl, —$C_{3-10}$ cycloalkyl, (5- to 10-membered)-$C_{1-9}$ heterocyclyl; said alkyl, cycloalkyl or heterocyclyl groups optionally being substituted by 1, 2 or 3 fluorine atoms, and solvates and salts thereof.

In another embodiment, Compounds of the Disclosure are compounds of formula (I), and the salts and solvates thereof, wherein one of $A^1$, $A^2$, and $A^3$ is nitrogen.

In another embodiment of this aspect of the disclosure, one of $A^1$ is nitrogen. In another embodiment, one of $A^2$ is nitrogen. In another embodiment, $A^3$ is nitrogen.

In another embodiment, each $A^1$ is CH and each of $A^2$ and $A^3$ is independently selected from CH and $C(R^6)$, provided that only one of $A^2$ and $A^3$ is $C(R^6)$.

In another embodiment, exactly one of $A^2$ and $A^3$ is $C(R^6)$ and no less than one and no more than two of $A^1$, $A^2$, and $A^3$ are nitrogen.

In another embodiment, Compounds of the Disclosure are compounds of formula (I), and the salts and solvates thereof, wherein each $A^1$ and $A^2$ is CH and $A^3$ is $C(R^6)$.

In another embodiment, Compounds of the Disclosure are compounds of formula (I), and the salts and solvates thereof, wherein each $A^1$ and $A^3$ is CH and $A^2$ is $C(R^6)$.

In another embodiment, Compounds of the Disclosure are compounds of formula (I), and the salts and solvates thereof, wherein $A^2$ is $C(R^6)$ and no less than one and no more than two of $A^1$ and $A^3$ are nitrogen.

In another embodiment, Compounds of the Disclosure are compounds of formula (I), and the salts and solvates thereof, wherein $A^3$ is $C(R^6)$ and no less than one and no more than two of $A^1$ and $A^2$ are nitrogen.

In another embodiment, Compounds of the Disclosure are compounds of formula (I) or (IA), wherein two of $A^1$, $A^2$, and $A^3$ are nitrogen.

In one embodiment, $R^3$ is selected from the group consisting of halogen, —CN, and —ORb, wherein Rb is as defined for formula (I). In another embodiment, $R^3$ is selected from the group consisting of —Cl, —CN, and —$OCH_3$.

In another embodiment, Compounds of the Disclosure are compounds represented by formula (IA):

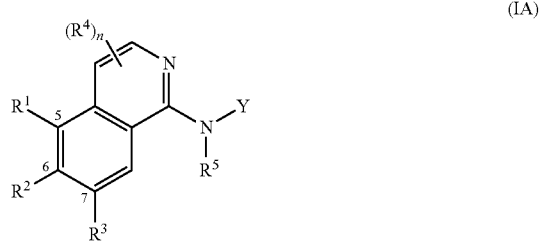

and the salts and solvates thereof, wherein:
$R^1$, $R^2$, $R^3$, $R^4$, and $R^5$, are as defined above for formula (I), with the proviso that at least one $R^1$, $R^2$, and $R^3$ is other than hydrogen;
n is 0 or 1, and
Y is selected from the group consisting of

Y1

Y2

Y3

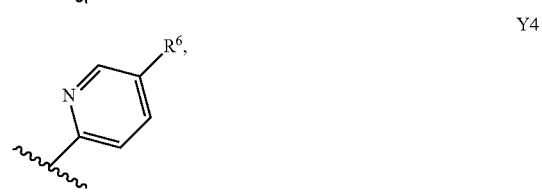

Y4

-continued
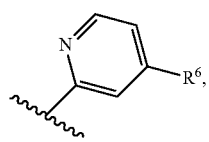 Y5
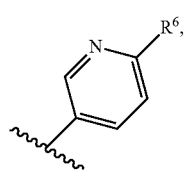 Y6
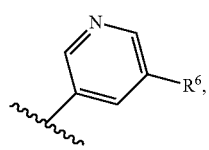 Y7
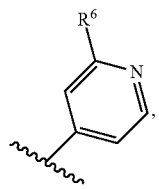 Y8
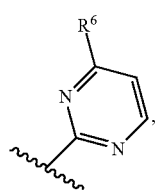 Y9
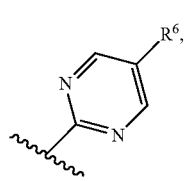 Y10
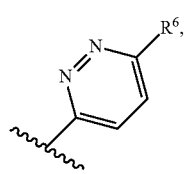 Y11
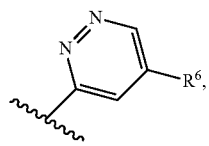 Y12
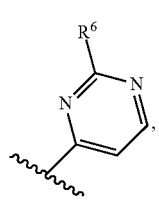 Y13
-continued
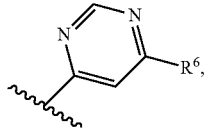 Y14
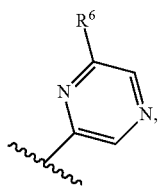 Y15
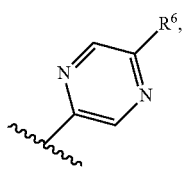 Y16
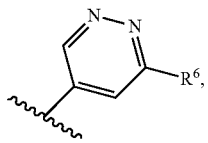 Y17
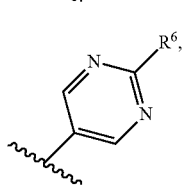 Y18
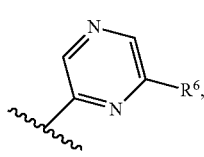 Y19
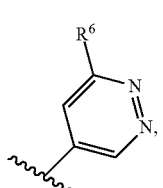 Y20
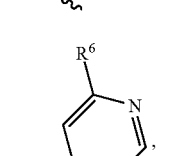 and Y21
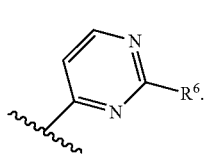 Y22
In another embodiment, Compounds of the Disclosure are compounds of formula (IA), wherein Y is selected from the group consisting of

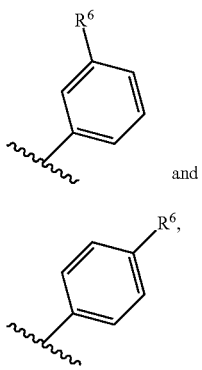
and

Y1

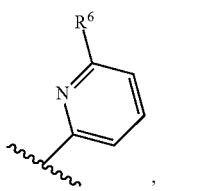

Y2 wherein R⁶ is as defined above for formula (I), and the salts and solvates thereof.

In another embodiment, Compounds of the Disclosure are compounds of formula (IA), wherein Y is selected from the group consisting of

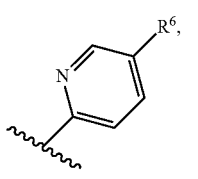

Y3

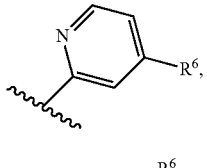

Y4

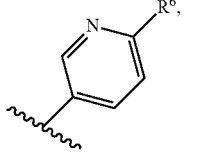

Y5

Y6

Y7

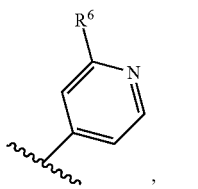

and

Y8 wherein R⁶ is as defined above for formula (I), and the salts and solvates thereof.

In another embodiment, Compounds of the Disclosure are compounds of formula (IA), wherein Y is selected from the group consisting of

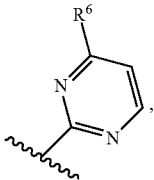

Y9

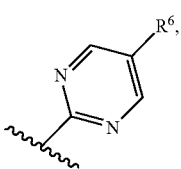

Y10

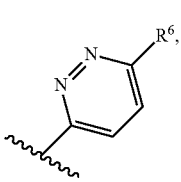

Y11

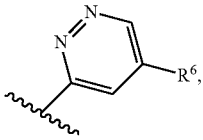

Y12

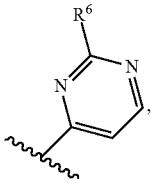

Y13

Y14

Y15

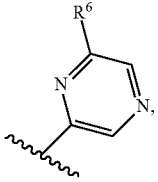

Y16

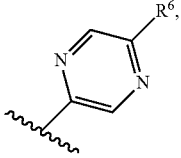

-continued

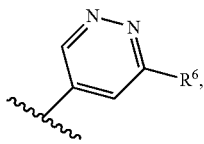
Y17

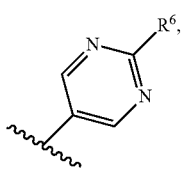
Y18

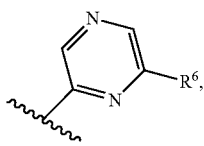
Y19

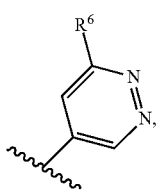
Y20

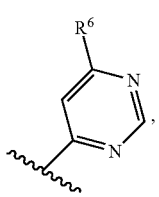
Y21
and

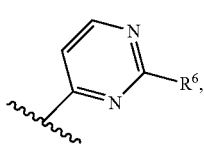
Y22 wherein $R^6$ is as defined above for formula (I), and the salts and solvates thereof.

In another embodiment, Compounds of the Disclosure are compounds of formula (I) or (IA), and the salts and solvates thereof, wherein Y is selected from the group consisting of Y3 and Y8.

In another embodiment, Compounds of the Disclosure are compounds of formula (IA), and the salts and solvates thereof, wherein Y is selected from the group consisting of Y4 and Y6.

In another embodiment, Compounds of the Disclosure are compounds of formula (IA), and the salts and solvates thereof, wherein Y is Y1.

In another embodiment, Compounds of the Disclosure are compounds of formula (IA), and the salts and solvates thereof, wherein Y is Y2.

In another embodiment, Compounds of the Disclosure are compounds of formula (IA), and the salts and solvates thereof, wherein Y is Y3.

In another embodiment, Compounds of the Disclosure are compounds of formula (IA), and the salts and solvates thereof, wherein Y is Y4.

In another embodiment, Compounds of the Disclosure are compounds of formula (IA), and the salts and solvates thereof, wherein Y is Y5.

In another embodiment, Compounds of the Disclosure are compounds of formula (IA), and the salts and solvates thereof, wherein Y is Y6.

In another embodiment, Compounds of the Disclosure are compounds of formula (IA), and the salts and solvates thereof, wherein Y is Y7.

In another embodiment, Compounds of the Disclosure are compounds of formula (IA), and the salts and solvates thereof, wherein Y is Y8.

In another embodiment, Compounds of the Disclosure are compounds of formula (IA), and the salts and solvates thereof, wherein Y is Y9.

In another embodiment, Compounds of the Disclosure are compounds of formula (IA), and the salts and solvates thereof, wherein Y is Y10.

In another embodiment, Compounds of the Disclosure are compounds of formula (IA), and the salts and solvates thereof, wherein Y is Y11.

In another embodiment, Compounds of the Disclosure are compounds of formula (IA), and the salts and solvates thereof, wherein Y is Y12.

In another embodiment, Compounds of the Disclosure are compounds of formula (IA), and the salts and solvates thereof, wherein Y is Y13.

In another embodiment, Compounds of the Disclosure are compounds of formula (IA), and the salts and solvates thereof, wherein Y is Y14.

In another embodiment, Compounds of the Disclosure are compounds of formula (IA), and the salts and solvates thereof, wherein Y is Y15.

In another embodiment, Compounds of the Disclosure are compounds of formula (IA), and the salts and solvates thereof, wherein Y is Y16.

In another embodiment, Compounds of the Disclosure are compounds of formula (IA), and the salts and solvates thereof, wherein Y is Y17.

In another embodiment, Compounds of the Disclosure are compounds of formula (IA), and the salts and solvates thereof, wherein Y is Y18.

In another embodiment, Compounds of the Disclosure are compounds of formula (IA), and the salts and solvates thereof, wherein Y is Y19.

In another embodiment, Compounds of the Disclosure are compounds of formula (IA), and the salts and solvates thereof, wherein Y is Y20.

In another embodiment, Compounds of the Disclosure are compounds of formula (IA), and the salts and solvates thereof, wherein Y is Y21.

In another embodiment, Compounds of the Disclosure are compounds of formula (IA), and the salts and solvates thereof, wherein Y is Y22.

In another embodiment, Compounds of the Disclosure are compounds of any one of formulae (I) and (IA), and the salts and solvates thereof, wherein $R^1$ and $R^2$ are H and $R^3$ is selected from the group consisting of halogen, —CN, and —ORb.

In another embodiment, Compounds of the Disclosure are compounds of any one of formulae (I) and (IA), and the salts and solvates thereof, wherein $R^1$ and $R^2$ are both H and $R^3$ is selected from the group consisting of —Cl, —CN, and —OCH$_3$.

In another embodiment, Compounds of the Disclosure are compounds of any one of formulae (I) and (IA), and the salts and solvates thereof, wherein B is —CO—.

In another embodiment, Compounds of the Disclosure are compounds of any one of formulae (I) and (IA), and the salts and solvates thereof, wherein B is —SO$_2$—.

In another embodiment, Compounds of the Disclosure are compounds of any one of formulae (I) and (IA), and the salts and solvates thereof, wherein n has a value selected from 0, 1, or 2. In another embodiment, n is 1 or 2. In another embodiment, n is 0. In another embodiment, n is 1. In another embodiment, n is 2.

In another embodiment, Compounds of the Disclosure are compounds of any one of formulae (I) and (IA), and the salts and solvates thereof, wherein n is 1 and $R^4$ is selected from the group consisting of chlorine, fluorine, bromine, methyl, ethyl, n-propyl, iso-propyl, n-butyl, tert-butyl, methoxy, ethoxy, tert-butoxy, —CN and hydroxy. In another embodiment, $R^4$ is fluorine.

In another embodiment, Compounds of the Disclosure are compounds of any one of formulae (I) and (IA), and the salts and solvates thereof, wherein $R^5$ is hydrogen. In another embodiment, Compounds of the Disclosure are compounds of any one of formulae (I) and (IA), and the salts and solvates thereof, wherein $R^5$ is —$C_{1-4}$ alkyl. In another embodiment, Compounds of the Disclosure are compounds of any one of formulae (I) and (IA), and the salts and solvates thereof, wherein $R^5$ is methyl or ethyl. In another embodiment, $R^5$ is methyl.

In another embodiment, Compounds of the Disclosure are compounds of any one of formulae (I) and (IA), and the salts and solvates thereof, wherein $R^7$ is —$C_{1-4}$ alkyl, wherein said alkyl is substituted with 1, 2, or 3 groups independently selected from the group consisting of halogen, hydroxy, —CN, —ORb, —SRb, —N(Rb)$_2$, —$C_{1-4}$alkyl optionally substituted with 1, 2, or 3 halogen atoms, optionally substituted —$C_{6-10}$ aryl, optionally substituted (5- to 10-membered)-$C_{1-9}$ heteroaryl, and (5- to 10-membered)-$C_{1-9}$ heterocyclyl; said cycloalkyl, alkylcycloalkyl, aryl, alkylaryl, heteroaryl, alkylheteroaryl, heterocyclyl, and alkylheterocyclyl optionally fused to a further (second) ring.

In another embodiment, Compounds of the Disclosure are compounds of any one of formulae (I) and (IA), and the salts and solvates thereof, wherein $R^7$ is —$C_{1-4}$ alkyl optionally substituted with 1, 2, or 3 substituents each independently selected from the group consisting of halogen, —CN, —SRb, —N(Rb)$_2$, and optionally substituted $C_{6-10}$ aryl, wherein Rb is hydrogen or —$C_{1-4}$ alkyl.

In another embodiment, Compounds of the Disclosure are compounds of any one of formulae (I) and (IA), and the salts and solvates thereof, wherein $R^7$ is selected from the group consisting of —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, (5- to 10-membered)-$C_{1-9}$ heteroaryl, —$C_{1-4}$ alkyl-(5- to 10-membered)-$C_{1-9}$ heteroaryl, (5- to 10-membered)-$C_{1-9}$ heterocyclyl, and —$C_{1-4}$ alkyl-(5- to 10-membered)-$C_{1-9}$ heterocyclyl, wherein said cycloalkyl, alkylcycloalkyl, aryl, alkylaryl, heteroaryl, alkylheteroaryl, heterocyclyl, and alkylheterocyclyl is fused to a further (second) ring.

In another embodiment, Compounds of the Disclosure are compounds of any one of formulae (I) and (IA), and the salts and solvates thereof, wherein $R^7$ is selected from the group consisting of —$C_{1-4}$ alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, (5- to 10-membered)-$C_{1-9}$ heteroaryl, —$C_{1-4}$ alkyl-(5- to 10-membered)-$C_{1-9}$ heteroaryl, (5- to 10-membered)-$C_{1-9}$ heterocyclyl, and —$C_{1-4}$ alkyl-(5- to 10-membered)-$C_{1-9}$ heterocyclyl.

In another embodiment, Compounds of the Disclosure are compounds of any one of formulae (I) and (IA), and the salts and solvates thereof, wherein n is 0 or 1, $R^1$ and $R^2$ are both hydrogen and $R^3$ is selected from the group consisting of halogen, —CN, —ORb, and —$C_{1-4}$ alkyl, wherein said —$C_{1-4}$ alkyl group is optionally substituted by 1, 2, or 3 independently selected halogen atoms, and wherein Rb is as defined above for formula (I). In another embodiment, n is 0. In another embodiment, Rb is hydrogen or —$C_{1-4}$ alkyl optionally substituted by 1, 2, or 3 independently selected halogen atoms.

In another embodiment, Compounds of the Disclosure are compounds of any one of formulae (I) and (IA), and the salts and solvates thereof, wherein n is 0 or 1, $R^1$ and $R^3$ are both hydrogen and $R^2$ is selected from the group consisting of halogen, —CN, —ORb, and —$C_{1-4}$ alkyl, wherein said —$C_{1-4}$ alkyl group is optionally substituted by 1, 2, or 3 independently selected halogen atoms, and wherein Rb is as defined above. In another embodiment, n is 0. In another embodiment, Rb is hydrogen or —$C_{1-4}$ alkyl optionally substituted by 1, 2, or 3 independently selected halogen atoms.

In another embodiment, Compounds of the Disclosure are compounds of any one of formulae (I) and (IA), and the salts and solvates thereof, wherein n is 0 or 1, $R^2$ and $R^3$ are both hydrogen and $R^1$ is selected from the group consisting of halogen, —CN, —ORb, and —$C_{1-4}$ alkyl, wherein said —$C_{1-4}$ alkyl group is optionally substituted by 1, 2, or 3 independently selected halogen atoms, and wherein Rb is as defined above. In another embodiment, n is 0. In another embodiment, Rb is hydrogen or —$C_{1-4}$ alkyl optionally substituted with 1, 2, or 3 independently selected halogen atoms.

In another embodiment, Compounds of the Disclosure are compounds of any one of formulae (I) and (IA), and the salts and solvates thereof, wherein n is 0 or 1, $R^1$ is hydrogen and $R^2$ and $R^3$ are each independently selected from the group consisting of halogen, —CN, —ORb, and —$C_{1-4}$ alkyl, wherein said —$C_{1-4}$ alkyl group is optionally substituted by 1, 2, or 3 independently selected halogen atoms, and wherein Rb is as defined above. In another embodiment, n is 0. In another embodiment, Rb is hydrogen or —$C_{1-4}$ alkyl optionally substituted with 1, 2, or 3 independently selected halogen atoms.

In another embodiment, Compounds of the Disclosure are compounds of any one of formulae (I) and (IA), and the salts and solvates thereof, wherein n is 0 or 1, $R^2$ is hydrogen and $R^1$ and $R^3$ are each independently selected from the group consisting of halogen, —CN, —ORb, and —$C_{1-4}$ alkyl, wherein said —$C_{1-4}$ alkyl group is optionally substituted by 1, 2, or 3 independently selected halogen atoms, and wherein Rb is as defined above. In another embodiment, n is 0. In another embodiment, Rb is hydrogen or —$C_{1-4}$ alkyl optionally substituted with 1, 2, or 3 independently selected halogen atoms.

In another embodiment, Compounds of the Disclosure are compounds of any one of formulae (I) and (IA), and the salts and solvates thereof, wherein n is 0 or 1, $R^3$ is hydrogen and $R^1$ and $R^2$ are each independently selected from the group consisting of halogen, —CN, —ORb, and —$C_{1-4}$ alkyl, wherein said —$C_{1-4}$ alkyl group is optionally substituted by 1, 2, or 3 independently selected halogen atoms, and wherein Rb is as defined above for formula (I). In another embodiment, n is 0. In another embodiment, Rb is hydrogen or —$C_{1-4}$ alkyl optionally substituted with 1, 2, or 3 independently selected halogen atoms.

In another embodiment, Compounds of the Disclosure are compounds of any one of formulae (I) and (IA), and the salts and solvates thereof, wherein n is 0 or 1, $R^1$, $R^2$, and $R^3$ are each independently selected from the group consisting of halogen, —CN, —ORb, and —$C_{1-4}$ alkyl, wherein said —$C_{1-4}$ alkyl group is optionally substituted by 1, 2, or 3 independently selected halogen atoms, and wherein Rb is as defined above. In another embodiment, n is 0.

In another embodiment, Compounds of the Disclosure are compounds of any one of formulae (I) and (IA), and the salts and solvates thereof, wherein $R^1$, $R^2$, and $R^3$, when other than hydrogen, are each independently selected from the group consisting of chlorine, fluorine, —CN, unsubstituted —$C_{1-4}$ alkyl (such as methyl or ethyl), —$C_{1-4}$ alkyl substituted with 1, 2, or 3 fluorine atoms (such as fluoromethyl, difluoromethyl, trifluoromethyl, 1-fluoroethyl, 1,1-difluoroethyl, or 1,1,1-trifluoroethyl), and —ORb, wherein Rb is hydrogen, unsubstituted —$C_{1-4}$ alkyl (such as methyl or ethyl), or —$C_{1-4}$ alkyl substituted with 1, 2, or 3 fluorine atoms (such as fluoromethyl, difluoromethyl, trifluoromethyl, 1-fluoroethyl, 1,1-difluoroethyl, or 1,1,1-trifluoroethyl). In another embodiment, $R^1$, $R^2$, and $R^3$, when other than hydrogen, are each independently selected from the group consisting of chlorine and —ORb, wherein Rb is hydrogen or unsubstituted —$C_{1-4}$ alkyl. In another embodiment, Rb is hydrogen or —$C_{1-4}$ alkyl.

In another embodiment, $R^7$ is selected from the group consisting of:

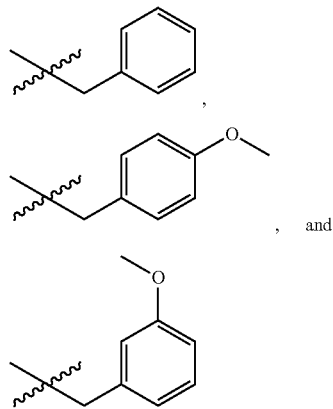

In another embodiment, $R^7$ is selected from the group consisting of:

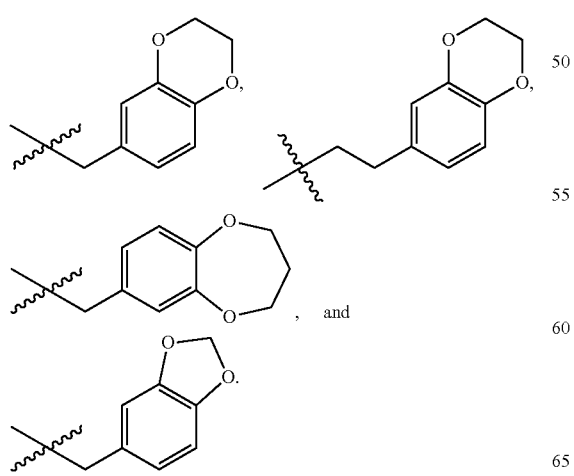

In another embodiment, $R^7$ is selected from the group consisting of:

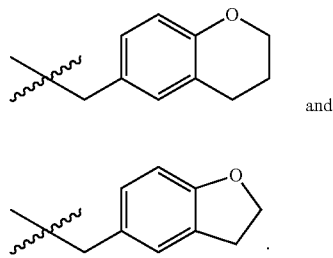

In another embodiment, $R^7$ is selected from the group consisting of:

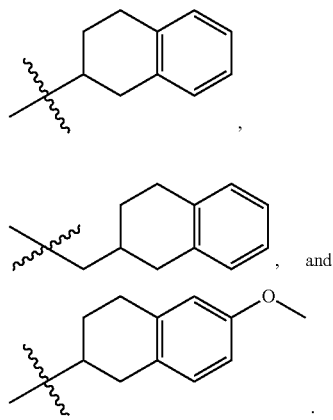

In another embodiment, $R^7$ is:

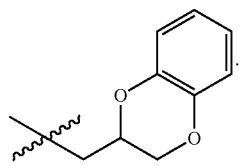 [SMILES: *CC1COc2ccccc2O1]

In another embodiment, $R^7$ is:

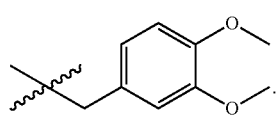 [SMILES: *Cc1ccc(OC)c(OC)c1]

In another embodiment, $R^7$ is selected from the group consisting of:

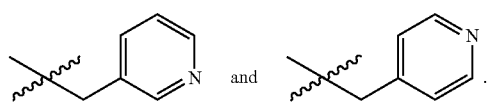 [SMILES: *Cc1cccnc1 ; *Cc1ccncc1]

In another embodiment, R⁷ is selected from the group consisting of:

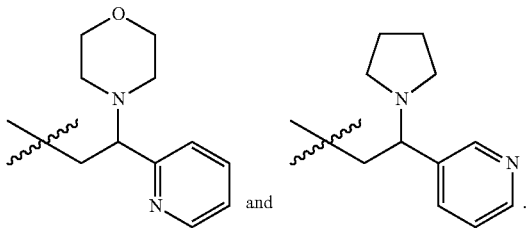 [SMILES: *CC(c1ccccn1)N1CCOCC1 ; *CC(c1cccnc1)N1CCCC1]

and

In another embodiment, R⁷ is selected from the group consisting of:

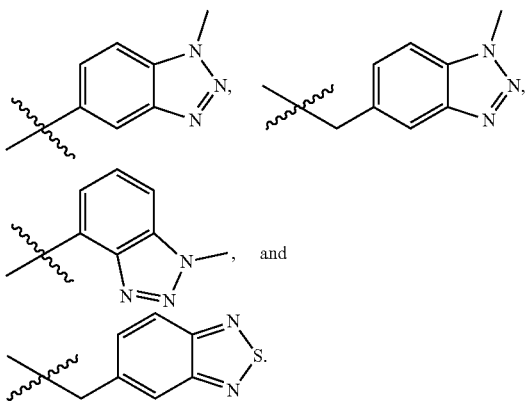

and

In another embodiment, the present disclosure provides a compound selected from the group consisting of:
3-((7-chloroisoquinolin-1-yl)amino)-N-(1-methyl-1H-benzo[d][1,2,3]triazol-5-yl)benzamide;
3-((7-chloroisoquinolin-1-yl)amino)-N-(2-morpholino-2-(pyridin-2-yl)ethyl)benzamide;
3-((7-chloroisoquinolin-1-yl)amino)-N-((2,3-dihydrobenzo[b][1,4]dioxin-6-yl)methyl)benzamide;
N-benzyl-3-((7-chloroisoquinolin-1-yl)amino)benzamide;
4-((7-chloroisoquinolin-1-yl)amino)-N-((2,3-dihydrobenzo[b][1,4]dioxin-6-yl)methyl)benzamide;
4-((7-chloroisoquinolin-1-yl)amino)-N-(2-(pyridin-3-yl)-2-(pyrrolidin-1-yl)ethyl)benzamide;
4-((7-chloroisoquinolin-1-yl)amino)-N-(2-(pyridin-3-yl)-2-(pyrrolidin-1-yl)ethyl)picolinamide;
4-((7-chloroisoquinolin-1-yl)amino)-N-((2,3-dihydrobenzo[b][1,4]dioxin-6-yl)methyl)picolinamide;
N-benzyl-4-((7-chloroisoquinolin-1-yl)amino)picolinamide;
4-((7-chloroisoquinolin-1-yl)amino)-N-(4-methoxybenzyl)picolinamide;
4-((7-chloroisoquinolin-1-yl)amino)-N-(3-methoxybenzyl)picolinamide;
4-((7-chloroisoquinolin-1-yl)amino)-N-(3,4-dimethoxybenzyl)picolinamide;
N-(benzo[c][1,2,5]thiadiazol-5-ylmethyl)-4-((7-chloroisoquinolin-1-yl)amino)picolinamide;
4-((7-chloroisoquinolin-1-yl)amino)-N-(1,2,3,4-tetrahydronaphthalen-2-yl)picolinamide;
4-((7-chloroisoquinolin-1-yl)amino)-N-((3,4-dihydro-2H-benzo[b][1,4]dioxepin-7-yl)methyl)picolinamide;
4-((7-chloroisoquinolin-1-yl)amino)-N-((2,3-dihydrobenzofuran-5-yl)methyl)picolinamide;
N-(benzo[d][1,3]dioxol-5-ylmethyl)-4-((7-chloroisoquinolin-1-yl)amino)picolinamide;
4-((7-chloroisoquinolin-1-yl)amino)-N-(2-(2,3-dihydrobenzo[b][1,4]dioxin-6-yl)ethyl)picolinamide;
4-((7-chloroisoquinolin-1-yl)amino)-N-(chroman-6-ylmethyl)picolinamide;
4-((7-chloroisoquinolin-1-yl)amino)-N-((1,2,3,4-tetrahydronaphthalen-2-yl)methyl)picolinamide;
4-((7-chloroisoquinolin-1-yl)amino)-N-((2,3-dihydrobenzo[b][1,4]dioxin-2-yl)methyl)picolinamide;
4-((7-chloroisoquinolin-1-yl)amino)-N-(pyridin-3-ylmethyl)picolinamide;
4-((7-chloroisoquinolin-1-yl)amino)-N-(pyridin-4-ylmethyl)picolinamide;
4-((7-methoxyisoquinolin-1-yl)amino)-N-(2-(pyridin-3-yl)-2-(pyrrolidin-1-yl)ethyl)picolinamide;
N-((2,3-dihydrobenzo[b][1,4]dioxin-6-yl)methyl)-4-((7-methoxyisoquinolin-1-yl)amino)picolinamide;
N-benzyl-4-((7-methoxyisoquinolin-1-yl)amino)picolinamide;
5-((7-chloroisoquinolin-1-yl)amino)-N-(2-(pyridin-3-yl)-2-(pyrrolidin-1-yl)ethyl)picolinamide;
5-((7-chloroisoquinolin-1-yl)amino)-N-((2,3-dihydrobenzo[b][1,4]dioxin-6-yl)methyl)picolinamide;
N-benzyl-5-((7-chloroisoquinolin-1-yl)amino)picolinamide;
5-((7-chloroisoquinolin-1-yl)amino)-N-(4-methoxybenzyl)picolinamide;
5-((7-chloroisoquinolin-1-yl)amino)-N-(3-methoxybenzyl)picolinamide;
5-((7-chloroisoquinolin-1-yl)amino)-N-(3,4-dimethoxybenzyl)picolinamide;
N-(benzo[c][1,2,5]thiadiazol-5-ylmethyl)-5-((7-chloroisoquinolin-1-yl)amino)picolinamide;
5-((7-chloroisoquinolin-1-yl)amino)-N-(1,2,3,4-tetrahydronaphthalen-2-yl)picolinamide;
5-((7-chloroisoquinolin-1-yl)amino)-N-((3,4-dihydro-2H-benzo[b][1,4]dioxepin-7-yl)methyl)picolinamide;
5-((7-chloroisoquinolin-1-yl)amino)-N-((2,3-dihydrobenzofuran-5-yl)methyl)picolinamide;
N-(benzo[d][1,3]dioxol-5-ylmethyl)-5-((7-chloroisoquinolin-1-yl)amino)picolinamide;
5-((7-chloroisoquinolin-1-yl)amino)-N-(2-(2,3-dihydrobenzo[b][1,4]dioxin-6-yl)ethyl)picolinamide;
5-((7-chloroisoquinolin-1-yl)amino)-N-(chroman-6-ylmethyl)picolinamide;
5-((7-chloroisoquinolin-1-yl)amino)-N-(6-methoxy-1,2,3,4-tetrahydronaphthalen-2-yl)picolinamide;
5-((7-chloroisoquinolin-1-yl)amino)-N-((1,2,3,4-tetrahydronaphthalen-2-yl)methyl)picolinamide;
5-((7-chloroisoquinolin-1-yl)amino)-N-((2,3-dihydrobenzo[b][1,4]dioxin-2-yl)methyl)picolinamide;
5-((7-chloroisoquinolin-1-yl)amino)-N-(pyridin-3-ylmethyl)picolinamide;
5-((7-chloroisoquinolin-1-yl)amino)-N-(pyridin-4-ylmethyl)picolinamide;
5-((7-cethoxyisoquinolin-1-yl)amino)-N-(1,2,3,4-tetrahydronaphthalen-2-yl)picolinamide;
N-(6-methoxy-1,2,3,4-tetrahydronaphthalen-2-yl)-5-((7-methoxyisoquinolin-1-yl)amino)picolinamide;
5-((7-cethoxyisoquinolin-1-yl)amino)-N-((1,2,3,4-tetrahydronaphthalen-2-yl)methyl)picolinamide;
5-((7-cyanoisoquinolin-1-yl)amino)-N-(1,2,3,4-tetrahydronaphthalen-2-yl)picolinamide;

5-((7-cyanoisoquinolin-1-yl)amino)-N-(pyridin-3-ylmethyl)picolinamide;

N-(benzo[c][1,2,5]thiadiazol-5-ylmethyl)-5-((7-cyanoisoquinolin-1-yl)amino)picolinamide;

5-((5-chloroisoquinolin-1-yl)amino)-N-(1,2,3,4-tetrahydronaphthalen-2-yl)picolinamide;

5-((5-chloroisoquinolin-1-yl)amino)-N-((2,3-dihydrobenzofuran-5-yl)methyl)picolinamide;

6-((7-chloroisoquinolin-1-yl)amino)-N-(2-(pyridin-3-yl)-2-(pyrrolidin-1-yl)ethyl)nicotinamide;

6-((7-chloroisoquinolin-1-yl)amino)-N-((2,3-dihydrobenzo[b][1,4]dioxin-6-yl)methyl)nicotinamide;

N-benzyl-6-((7-chloroisoquinolin-1-yl)amino)nicotinamide;

6-((7-chloroisoquinolin-1-yl)amino)-N-(4-methoxybenzyl)nicotinamide;

6-((7-chloroisoquinolin-1-yl)amino)-N-(3-methoxybenzyl)nicotinamide;

6-((7-chloroisoquinolin-1-yl)amino)-N-(3,4-dimethoxybenzyl)nicotinamide;

N-(benzo[c][1,2,5]thiadiazol-5-ylmethyl)-6-((7-chloroisoquinolin-1-yl)amino)nicotinamide;

6-((7-chloroisoquinolin-1-yl)amino)-N-(1,2,3,4-tetrahydronaphthalen-2-yl)nicotinamide;

6-((7-chloroisoquinolin-1-yl)amino)-N-((3,4-dihydro-2H-benzo[b][1,4]dioxepin-7-yl)methyl)nicotinamide;

N-(benzo[d][1,3]dioxol-5-ylmethyl)-6-((7-chloroisoquinolin-1-yl)amino)nicotinamide;

6-((7-chloroisoquinolin-1-yl)amino)-N-(chroman-6-ylmethyl)nicotinamide;

5-((7-methoxyisoquinolin-1-yl)amino)-N-(pyridin-3-ylmethyl)picolinamide;

3-((7-chloroisoquinolin-1-yl)amino)-N-(2-(pyridin-3-yl)-2-(pyrrolidin-1-yl)ethyl)benzenesulfonamide;

3-((7-chloroisoquinolin-1-yl)amino)-N-(2-morpholino-2-(pyridin-2-yl)ethyl)benzenesulfonamide;

3-((7-chloroisoquinolin-1-yl)amino)-N-(1-methyl-1H-benzo[d][1,2,3]triazol-4-yl)benzenesulfonamide;

N-benzyl-3-((7-chloroisoquinolin-1-yl)amino)benzenesulfonamide;

3-((7-chloroisoquinolin-1-yl)amino)-N-((2,3-dihydrobenzo[b][1,4]dioxin-6-yl)methyl)benzenesulfonamide;

3-((7-chloroisoquinolin-1-yl)amino)-N-(1,2,3,4-tetrahydronaphthalen-2-yl)benzenesulfonamide;

3-((7-chloroisoquinolin-1-yl)amino)-N-((1-methyl-1H-benzo[d][1,2,3]triazol-5-yl)methyl)benzenesulfonamide;

4-((7-chloroisoquinolin-1-yl)amino)-N-(2-morpholino-2-(pyridin-2-yl)ethyl)benzenesulfonamide;

4-((7-chloroisoquinolin-1-yl)amino)-N-(1-methyl-1H-benzo[d][1,2,3]triazol-4-yl)benzenesulfonamide;

N-(benzo[c][1,2,5]thiadiazol-5-ylmethyl)-3-((7-chloroisoquinolin-1-yl)amino)benzenesulfonamide;

4-((7-chloroisoquinolin-1-yl)amino)-N-((2,3-dihydrobenzo[b][1,4]dioxin-6-yl)methyl)benzenesulfonamide;

N-(benzo[c][1,2,5]thiadiazol-5-ylmethyl)-4-((7-chloroisoquinolin-1-yl)amino)benzenesulfonamide;

4-((7-chloroisoquinolin-1-yl)amino)-N-(1,2,3,4-tetrahydronaphthalen-2-yl)benzenesulfonamide;

4-((7-chloroisoquinolin-1-yl)amino)-N-((1,2,3,4-tetrahydronaphthalen-2-yl)methyl)benzenesulfonamide;

4-((7-chloroisoquinolin-1-yl)amino)-N-((2,3-dihydrobenzo[b][1,4]dioxin-2-yl)methyl)benzenesulfonamide; and N-benzyl-4-((7-chloroisoquinolin-1-yl)amino)benzenesulfonamide;

and the salts and solvates thereof.

The term "amine protecting group" or "amino protecting group" as used herein refers to a group that blocks (i.e., protects) the amine functionality while reactions are carried out on other functional groups or parts of the molecule. Those skilled in the art will be familiar with the selection, attachment, and cleavage of amine protecting groups and will appreciate that many different protective groups are know in the art, the suitability of one protective group or another being dependent on the particular synthetic scheme planned. Treatises on the subject are available for consultation, such as Wuts, P. G. M. & Greene, T. W., *Greene's Protective Groups in Organic Synthesis,* 4rd Ed. (J. Wiley & Sons, 2007), herein incorporated by reference in its entirety. Suitable amine protecting groups include methyl carbamate, tert-butyloxycarbonyl (tert-butyl carbamate; BOC), 9-fluorenylmethyl carbamate, benzyl carbamate, 2-(trimethylsilyl) ethyl carbamate, trifluoroacetamide, benzylamine, allylamine, tritylamine, trichloroacetyl, trifluoroacetyl, p-toluenesulfonyl, and allyl carbamate. In another embodiment, the protected amino group can be a phthalimide-protected amino group (NPhth).

The compounds of formulae (I) and (IA) can be in the form of solvates or salts, for example wherein the solvating agents and/or the salt's counter-ions are pharmaceutically acceptable species.

As used herein, the terms "halogen" or "halo" refer to —F, —Cl, —Br, or —I.

As used herein, the term "hydroxyl" or "hydroxy" refers to the group —OH,

As used herein, the term "alkyl" refers to a linear or branched hydrocarbon chain radical consisting of carbon and hydrogen atoms, containing no unsaturation, which is attached to the rest of the molecule by a single bond and, unless otherwise specified, an alkyl radical typically has from 1 to 4 carbon atoms (i.e., a $C_{1-4}$ alkyl group). Exemplary alkyl groups can be methyl, ethyl, n-propyl, i-propyl, n-butyl, tert-butyl, i-butyl and sec-butyl. In another embodiment, the alkyl is $C_{1-2}$ alkyl (methyl or ethyl).

As used herein, the term "halo($C_{1-4}$)alkyl" refers to any of the above-mentioned $C_{1-4}$ alkyl groups, substituted by one or more halogen atoms (fluorine, chlorine, bromine or iodine atoms) (e.g., fluoromethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups). In another embodiment, halo($C_{1-4}$) alkyl is monohalo($C_{1-4}$)alkyl. The term "monohalo($C_{1-4}$) alkyl" indicates that the $C_{1-4}$ alkyl group is substituted by exactly one halogen atom. The term "dihalo($C_{1-4}$)alkyl" means that the $C_{1-4}$ alkyl group is substituted by two halogen atoms. The term "trihalo($C_{1-4}$)alkyl" means that the $C_{1-4}$ alkyl group is substituted by three halogen atoms. The halogen atoms can be attached to the same or different carbon atoms. The one or more halogen atoms can be the same or different.

As used herein, the term "$C_{1-4}$ alkoxy" refers to oxygen substituted by one of the $C_{1-4}$ alkyl groups mentioned above (e.g., methoxy, ethoxy, propoxy, iso-propoxy, butoxy, tert-butoxy, iso-butoxy, and sec-butoxy), for example by one of the $C_{1-2}$ alkyl groups.

As used herein, the term "cycloalkyl" embraces saturated carbocyclic radicals and, unless otherwise specified, a cycloalkyl radical typically has from 3 to 6 carbon atoms. Examples include cyclopropyl, cyclobutyl, cyclopentyl, cyclohexyl and cycloheptyl. It is, for example, cyclopropyl, cyclopentyl and cyclohexyl. In another embodiment, the cycloalkyl group is $C_{3-10}$ cycloalkyl.

As used herein, the term "alkylcycloalkyl" when employed in the definition of a substituent refers to a cycloalkyl group which is linked through an alkylene radical with the core structure which it substitutes. As an example, a cyclopentylethyl substituent is a substituent consisting of a cyclopentyl group linked through an ethylene group to the core structure which it substitutes.

As used herein, the terms "heterocyclyl" or "heterocyclic group" embrace typically a monocyclic or polycyclic, non-aromatic, saturated or unsaturated $C_{2-10}$ carbocyclic ring, such as a 5- to 10-membered radical, in which one or more, for example 1, 2, 3 or 4 of the carbon atoms, for example, 1 or 2 of the carbon atoms are replaced by a heteroatom selected from N, O and S. In one embodiment, the heterocyclyl is a $C_{3-7}$ heterocyclyl, i.e., a heterocycle having 3-7 carbon atoms and at least one heteroatom. In another embodiment, a heterocyclyl is a (5- to 10-membered)-$C_{1-9}$ heterocyclyl, i.e., a heterocycle having 5- to 10-members, of which 1-9 members are carbon. In another embodiment, the heteroatom is N. In another embodiment, the heteroatom is O.

In another embodiment, the heterocyclyl radicals are saturated. A heterocyclic radical may be a single ring or two or more fused rings wherein at least one ring contains a heteroatom. When a heterocyclyl radical carries one or more substituents, the substituents may be the same or different.

A said optionally substituted heterocyclyl is typically unsubstituted or substituted with 1, 2 or 3 substituents which may be the same or different. Examples of heterocyclic radicals include piperidyl, pyrrolidyl, pyrrolinyl, piperazinyl, morpholinyl, thiomorpholinyl, pyrazolinyl, pyrazolidinyl, quinuclidinyl, tetrazolyl, cromanyl, isocromanyl, imidazolidinyl, oxiranyl, azaridinyl, 4,5-dihydro-oxazolyl and 3-aza-tetrahydrofuranyl.

As used herein, the term "alkylheterocyclyl" when employed in the definition of a substituent refers to a heterocyclyl group as defined above which is linked through an alkylene radical with the core structure which it substitutes. In one embodiment, the alkylheterocyclyl is a-$C_{1-4}$ alkyl-(5- to 10-membered)-$C_{1-9}$ heterocyclyl.

As used herein, the term "aryl" designates typically a $C_{6-10}$ monocyclic or polycyclic aryl radical such as phenyl and naphthyl. In another embodiment, the aryl is phenyl. A said optionally substituted aryl radical is typically unsubstituted or substituted with 1, 2 or 3 substituents which may be the same or different. The substituents are, for example, selected from halogen atoms, for example, fluorine or chlorine atoms, hydroxy groups, alkoxycarbonyl groups in which the alkyl moiety has from 1 to 4 carbon atoms, hydroxycarbonyl groups, carbamoyl groups, nitro groups, cyano groups, $C_{1-4}$ alkyl groups optionally substituted by one or more halogen atoms, $C_{1-4}$ alkoxy groups, optionally substituted by one or more halogen atoms and $C_{1-4}$ hydroxyalkyl groups. When an aryl radical carries 2 or more substituents, the substituents may be the same or different. Unless otherwise specified, the substituents on an aryl group are typically themselves unsubstituted.

As used herein, the term "alkylaryl" when employed in the definition of a substituent refers to an aryl group as defined above which is linked through an alkylene radical with the core structure which it substitutes.

As used herein, the term "heteroaryl" designates typically a 5- to 10-membered ring system, comprising at least one heteroaromatic ring and containing at least one heteroatom selected from O, S and N, typically 1, 2, 3, or 4 heteroatoms. A heteroaryl group may comprise a single ring or two or more fused rings wherein at least one ring contains a heteroatom. A said optionally substituted heteroaryl group is typically unsubstituted or substituted with 1, 2 or 3 substituents which may be the same or different. The substituents are, for example, selected from halogen atoms, for example, fluorine, chlorine or bromine atoms, alkoxycarbonyl groups in which the alkyl moiety has from 1 to 4 carbon atoms, carbamoyl groups, nitro groups, hydroxy groups, $C_{1-4}$ alkyl groups, optionally substituted by one or more halogen atoms and $C_{1-4}$ alkoxy groups, optionally substituted by one or more halogen atoms. When an heteroaryl radical carries 2 or more substituents, the substituents may be the same or different. Unless otherwise specified, the substituents on a heteroaryl radical are typically themselves unsubstituted.

Examples of heteroaryl groups include pyridyl, pyrazinyl, pyrimidinyl, pyridazinyl, furyl, tetrazolyl, benzofuranyl, oxadiazolyl, oxazolyl, isoxazolyl, benzoxazolyl, imidazolyl, benzimidazolyl, thiazolyl, thiadiazolyl, thienyl, pyrrolyl, pyridinyl, benzothiazolyl, indolyl, indazolyl, purinyl, quinolyl, isoquinolyl, phthalazinyl, naphthyridinyl, quinoxalinyl, quinazolinyl, quinolizinyl, cinnolinyl, triazolyl, indolizinyl, indolinyl, isoindolinyl, isoindolyl, imidazolidinyl, pteridinyl, thianthrenyl, pyrazolyl, 2H-pyrazolo[3,4-d]pyrimidinyl, 1H-pyrazolo[3,4-d]pyrimidinyl, thieno[2,3-d]pyrimidinyl, and the various pyrrolopyridyl radicals.

In another embodiment, the heteroaryl is a (5- to 10-membered)-$C_{1-9}$ heteroaryl. In another embodiment, the heteroaryl is optionally substituted with 1, 2, or 3 groups independently selected from the group consisting of halogen, hydroxy, —CN, —ORb, —SRb, —N(Rb)$_2$, —$C_{1-4}$ alkyl optionally substituted with 1, 2, or 3 halogen atoms, optionally substituted $C_{6-10}$ aryl, optionally substituted (5- to 10-membered)-$C_{1-9}$ heteroaryl, and (5- to 10-membered)-$C_{1-9}$ heterocyclyl; said cycloalkyl, alkylcycloalkyl, aryl, alkylaryl, heteroaryl, alkylheteroaryl, heterocyclyl, and alkylheterocyclyl is optionally fused to a further (second) ring.

The mention of optionally substituted heteroaryl radicals or rests within the present disclosure is intended to cover the N-oxides obtainable from these radicals when they comprise N-atoms.

As used herein, the term "alkylheteroaryl" when employed in the definition of a substituent refers to an heteroaryl group as defined above which is linked through an alkylene radical with the core structure which it substitutes. In another embodiment, the alkylheteroaryl is a —$C_{1-4}$ alkyl-(5- to 10-membered)-$C_{1-9}$ heteroaryl.

The term "pharmaceutically acceptable" refers to compositions and molecular entities that are physiologically tolerable and do not typically produce an allergic reaction or a similar unfavorable reaction, such as gastric disorders, dizziness and suchlike, when administered to a human or animal. For example, the term "pharmaceutically acceptable" means it is approved by a regulatory agency of a state or federal government or is included in the U.S. Pharmacopoeia or other generally recognized pharmacopoeia for use in animals, and more particularly in humans.

The term "treatment" or "treating" refers to administering a therapy in an amount, manner or mode effective to improve a condition, symptom, or parameter associated with a condition or to prevent progression of a condition, to either a statistically significant degree or to a degree detectable to one skilled in the art. An effective amount, manner, or mode can vary depending on the subject and may be tailored to the patient.

The term "about", as used herein in connection with a measured quantity, refers to the normal variations in that measured quantity, as expected by the skilled artisan making the measurement and exercising a level of care commensurate with the objective of measurement and precision of the measuring equipment. Typically, the term "about" includes the recited number ±10%. Thus, "about 10" means 9 to 11.

As used herein, the term "optionally substituted" refers to a group that may be unsubstituted or substituted.

The term "solvate" means any form of the active compound of the disclosure which has another molecule (for example a polar solvent such as water or ethanol, a cyclodextrin or a dendrimer) attached to it through noncovalent bonds. Methods of solvation are known within the art.

The disclosure also provides salts of the Compounds of the Disclosure. Non-limiting examples are sulphates; hydrohalide salts; phosphates; lower alkane sulphonates; arylsulphonates; salts of $C_{1-20}$ aliphatic mono-, di- or tribasic acids which may contain one or more double bonds, an aryl nucleus or other functional groups such as hydroxy, amino, or keto; salts of aromatic acids in which the aromatic nuclei may or may not be substituted with groups such as hydroxyl, lower alkoxyl, amino, mono- or di- lower alkylamino sulphonamido. Also included within the scope of the disclosure are quaternary salts of the tertiary nitrogen atom with lower alkyl halides or sulphates, and oxygenated derivatives of the tertiary nitrogen atom, such as the N-oxides. In preparing dosage formulations, those skilled in the art will select the pharmaceutically acceptable salts.

Solvates and salts can be prepared by methods known in the state of the art. Note that the non-pharmaceutically acceptable solvates also fall within the scope of the disclosure because they can be useful in preparing pharmaceutically acceptable salts and solvates.

The Compounds of the Disclosure also seek to include compounds that differ only in the presence of one or more isotopically enriched atoms. For example, compounds having the present structures except for the replacement of a hydrogen by a deuterium or tritium, or the replacement of a carbon by a carbon enriched in $^{11}C$, $^{13}C$ or $^{14}C$ or the replacement of a nitrogen by a $^{15}N$ enriched nitrogen are within the scope of this disclosure.

Some of the compounds disclosed herein may contain one or more asymmetric centers and may thus give rise to enantiomers, diastereomers, and other stereoisomeric forms, such as epimers. The present disclosure is meant to encompass the uses of all such possible forms, as well as their racemic and resolved forms and mixtures thereof. The individual enantiomers may be separated according to methods known to those of ordinary skill in the art in view of the present disclosure. When the compounds described herein contain olefinic double bonds or other centers of geometric asymmetry, and unless specified otherwise, it is intended that they include both E and Z geometric isomers. All tautomers are intended to be encompassed by the present disclosure as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The term "epimer" refers to diastereomers that have opposite configuration at only one of two or more tetrahedral streogenic centers present in the respective molecular entities.

The term "stereogenic center" is an atom, bearing groups such that an interchanging of any two groups leads to a stereoisomer.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "resolution" refers to the separation or concentration or depletion of one of the two enantiomeric forms of a molecule.

The terms "a" and "an" refer to one or more.

As used herein, the term "enzyme replacement therapy," or "ERT" refers to administering an exogenously-produced natural or recombinant enzyme or analog thereof to a patient in need thereof. In the case of a lyosomal storage disease, for example, the patient accumulates harmful levels of a substrate (i.e., material stored) in lysosomes due to a deficiency or defect in an enzyme responsible for metabolizing the substrate, or due to a deficiency in an enzymatic activator required for proper enzymatic function. Enzyme replacement therapy is provided to the patient to reduce the levels of (i.e., debulk) accumulated substrate in affected tissues. Enzyme replacement therapies for treating lysosomal storage diseases are known in the art. In accordance with a combination therapy of the disclosure, a lysosomal enzyme, e.g., β-galactosidase, can be used for enzyme replacement therapy to reduce the levels of corresponding substrate, e.g., GM1-ganglioside, glycoprotein, keratan sulfate, in a patient having GM1 gangliosidosis or Morquio B syndrome.

As used herein, an "effective amount" of an enzyme," when administered to a subject in a combination therapy of the disclosure, is an amount sufficient to improve the clinical course of a lysosomal storage disease, where clinical improvement is measured by any of the variety of defined parameters well known to the skilled artisan.

As used herein the term "small molecule chaperone" refers to a compound, other than a Compound of the Disclosure, that is capable of binding allosterically or competitively to a mutated enzyme, e.g., β-galactosidase, thereby stabilizing the enzyme against degradation. In some embodiments, the small molecule chaperone facilitates proper folding and transport of an enzyme to its site of action. Small molecule chaperones for the treatment of lysosomal storage diseases are known in the art. See, e.g., US 2016/0207933 A1 and WO 2011/049737 A1.

Synthesis of Compounds of the Disclosure

Another aspect of the disclosure refers to procedures to obtain Compounds of the Disclosure. The following methods describe the procedures for obtaining Compounds of the Disclosure, or solvates or salts thereof.

Various synthetic routes for synthesizing compounds of formula (I) are summarized in the schemes below.

Scheme 1 illustrates the different synthetic paths to obtain compounds of formula (I) wherein one of $A^2$ is C(CO-NHR$^7$). These compounds have formula (Ia).

Scheme 2 illustrates the different synthetic paths to obtain compounds of formula (I) wherein $A^3$ is C(CONHR$^7$). These compounds have formula (Ib).

Schemes 3 and 5 illustrates the different synthetic paths to obtain compounds of formula (I) wherein one of the $A^2$ is C(SO$_2$NHR$^7$). These compounds have formula (Ic).

Schemes 4 and 6 illustrates the different synthetic paths to obtain compounds of formula (I) wherein $A^3$ is C(SO$_2$NHR$^7$). These compounds have formula (Id).

Schemes 1 and 2 are virtually identical with the exception of the position of the carboxylic acid/acid chloride/amide/ester on the six-member ring (III, IV, V, VIII, IX, and X) and the isoquinoline (Ia, Ib, VIa, VIb, VIIa, and VIIb). Therefore, the different reactions A to H and their conditions will be described together for the two Schemes.

Schemes 3 and 5 and Schemes 4 and 6 are virtually identical with the exception of the position of the sulfonyl group on the six-member ring (IV, VIII, IX, XII, XIII, XIV, XV, and XVII) and the isoquinoline (Ia, Ib, VI, and XVI). Therefore, the different reactions I to Q and their conditions will be described together for the two couples of schemes.

Scheme 1.
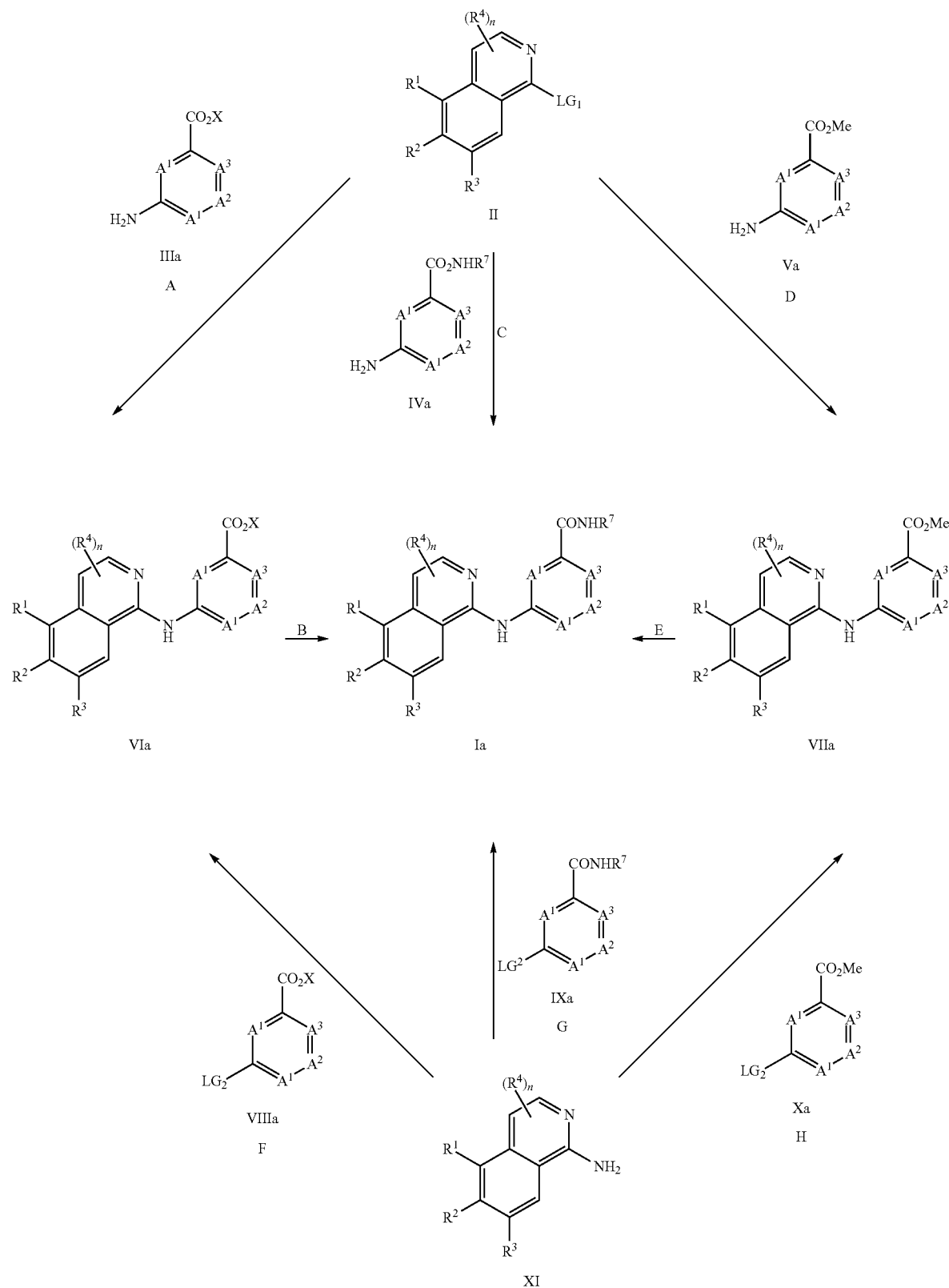
Wherein X is H or halogen

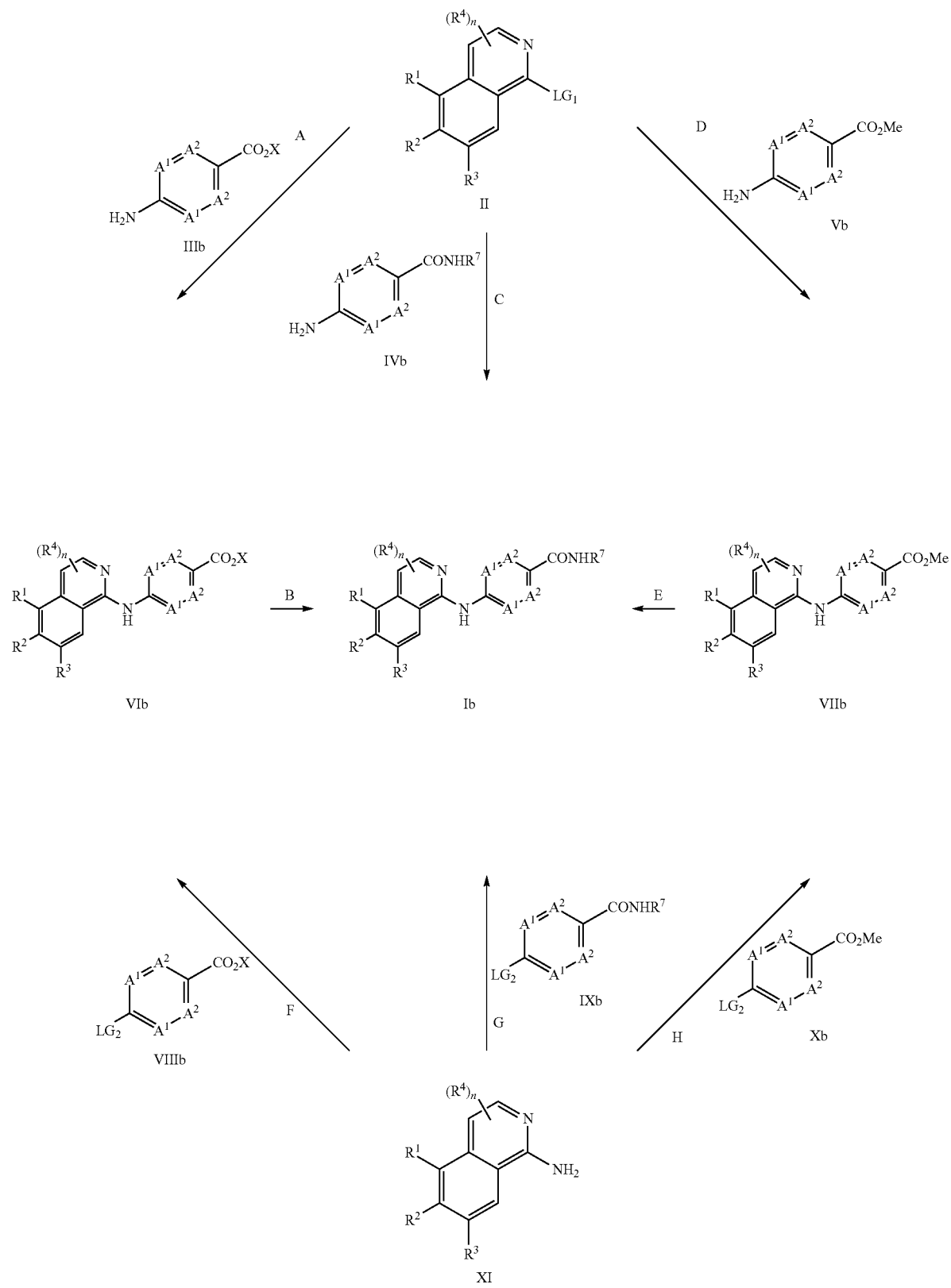
Scheme 2.
Wherein X is H or halogen

Scheme 3.
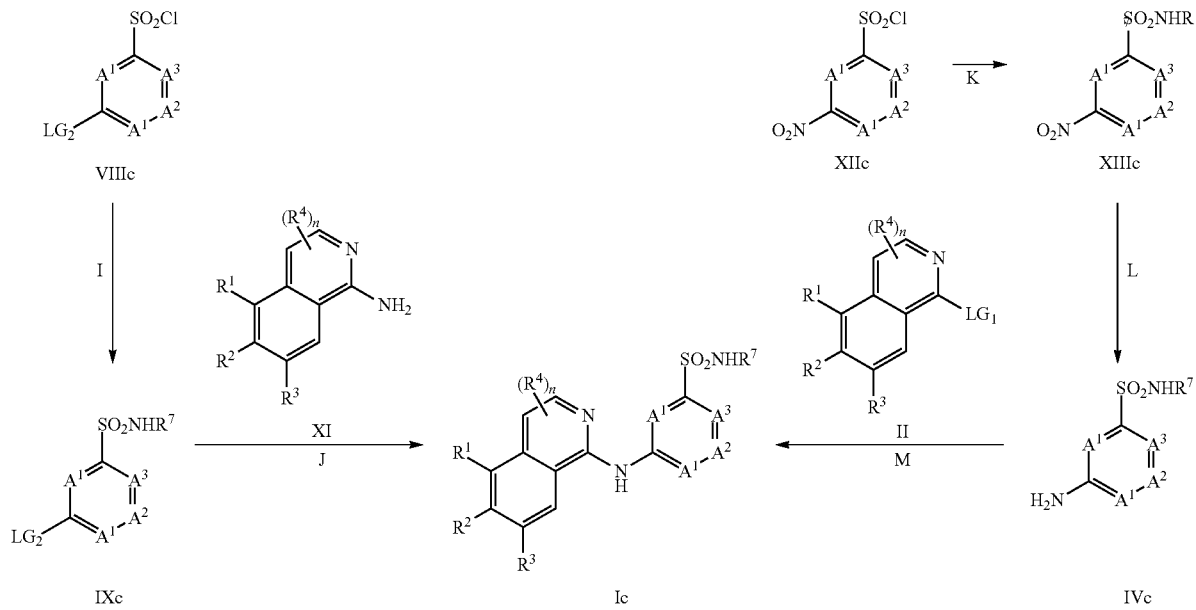
Scheme 4.
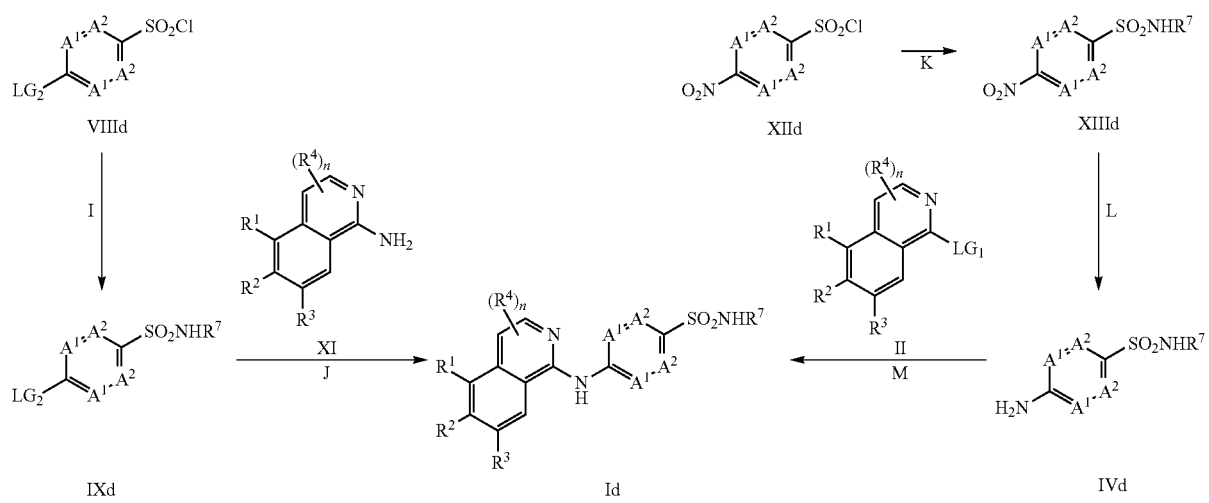

Scheme 5.
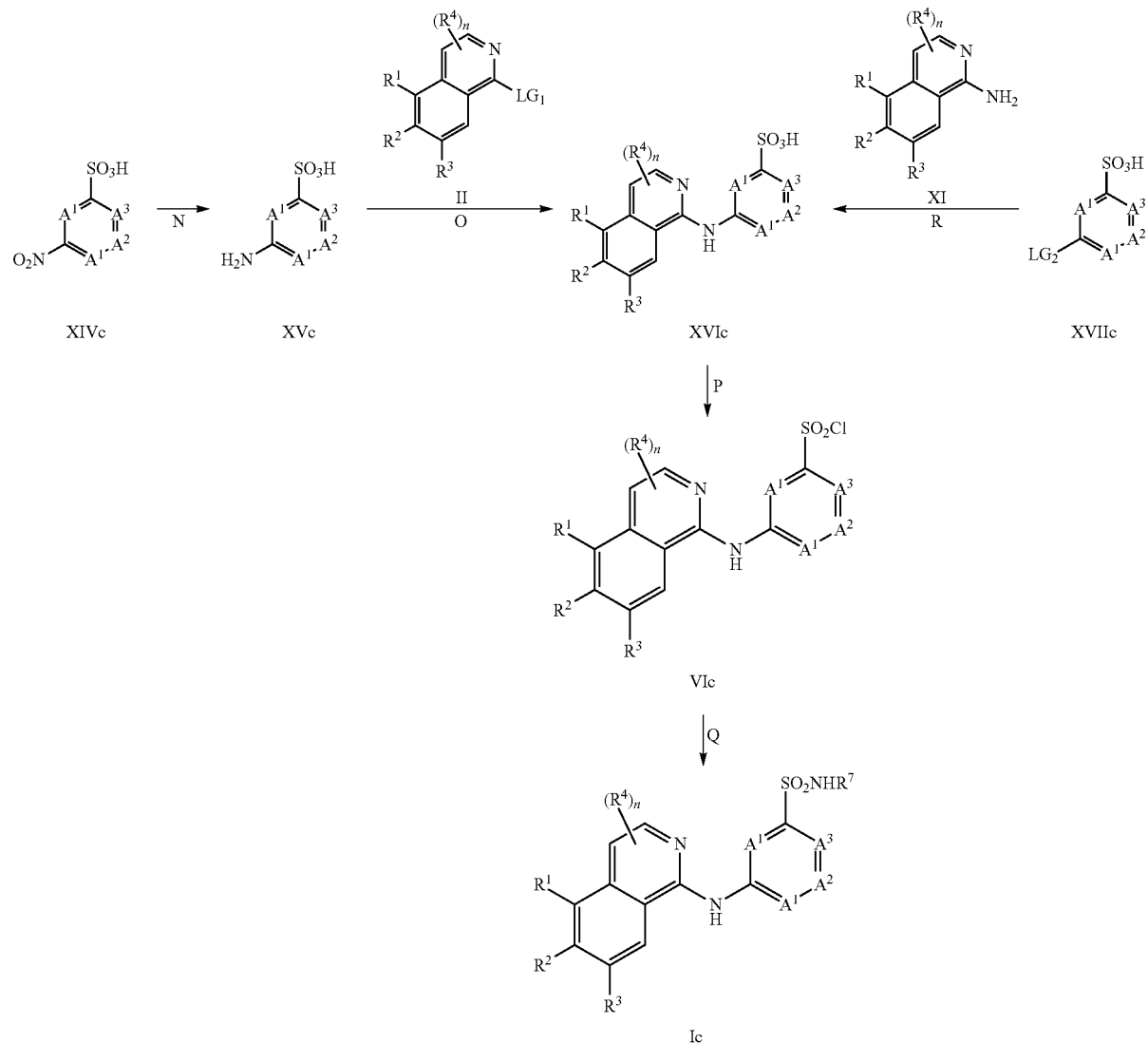

Scheme 6.
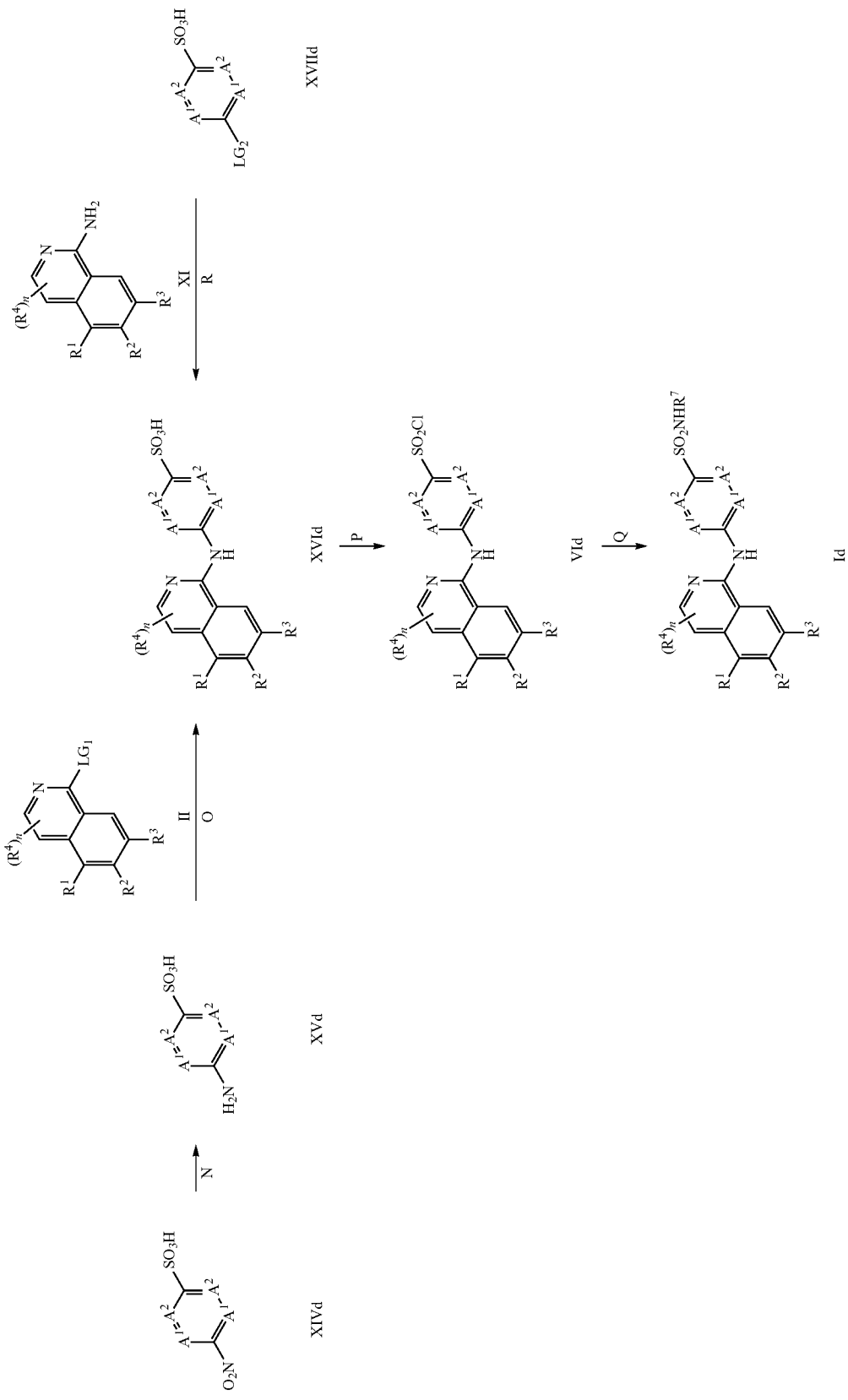

Method 1
Step 1

In a first method according to the disclosure, a compound of formula (II) wherein $R^1$, $R^2$, $R^3$, $R^4$, and n are as defined above for formula (I) and $LG_1$ is a leaving group is reacted with a compound of formula (III), wherein $A^1$, $A^2$, and $A^3$ are as defined above for formula (I), to yield a compound of formula (VI) as illustrated in reaction A of the scheme above (Scheme 1 and 2).

Reaction A is used to prepare compounds of formula (VIa) or (VIb) by reaction of a compound of formula (IIIa) or (IIIb) with a compound of formula (II) wherein $LG_1$ represents a leaving group such as iodo, bromo, chloro or a sulphonate group (e.g. —OS(O)$_2$CF$_3$, —OS(O)$_2$CH$_3$, or —OS(O)$_2$PhMe). Said reaction can be performed under standard conditions in the presence of a suitable base, such as pyridine, triethylamine, dimethylaminopyridine, diisopropylamine, potassium tert-butoxide, sodium hydroxide, or mixtures thereof), and an appropriate solvent, such as pyridine, dichloromethane, chloroform, tetrahydrofuran, dimethylformamide, dimethylsulfoxide, water, or mixtures thereof and, for example, at around room temperature or above, or under microwave irradiation reaction conditions.

The reaction can also be carried out in the presence of an appropriate metal catalyst (or a salt or complex thereof), such as Cu, Cu(OAc)$_2$, CuI (or CuI/diamine complex) copper tris(triphenyl-phosphine)bromide, Pd(OAc)$_2$, tris(dibenzylideneacetone) dipalladium(0) (Pd$_2$(dba)$_3$), Palladium(π-cinnamyl) chloride dimer, Pd[P(p-tol)$_3$]$_2$, Pd[P(o-tol)$_3$]$_2$, ZnCl$_2$, NiCl$_2$, or Ni(COD)$_2$, and also optionally in the presence of an additive, such as Ph$_3$P, 2,2'-bis(diphenylphosphino)-1,1'-binaphthyl, XantPhos, Josiphos, MorDalphos, NaI, or an appropriate crown ether, such as 18-crown-6-benzene, in the presence of an appropriate base, such as sodium hydride, triethylamine, pyridine, N,N'-dimethylethylenediamine, sodium carbonate, potassium carbonate, potassium phosphate, cesium carbonate, lithium bis(trimethylsilyl)amide, sodium tert-butoxide or potassium tert-butoxide (or a mixture thereof, optionally in the presence of 4 Å molecular sieves), in a suitable solvent (e.g. dichloromethane, dioxane, toluene, ethanol, isopropanol, dimethylformamide, ethylene glycol, ethylene glycol dimethyl ether, water, dimethylsulfoxide, acetonitrile, dimethylacetamide, N-methylpyrrolidinone, tetrahydrofuran or a mixture thereof) or absence of solvent.

The reaction can be carried out with protecting groups present and those protecting groups may be removed after the reaction. Suitable protecting groups are known to the person skilled in the art (see T. W. Greene, "Protective Groups in Organic Synthesis," 3rd Edition, New York, 1999).

Step 2

The carboxylic acid or acid chloride of the compound of formula (VIa) or (VIb) is subsequently converted to a substituted amide group to yield the compound of formula (Ia) or (Ib) according to the disclosure as illustrated in reaction B of the schemes above (Scheme 1 and 2). Reaction B is carried out under standard amide coupling conditions, for example in the presence of a suitable coupling agent (e.g. 1,1'-carbonyldiimidazole, N,N'-cyclohexylcarbodiimide, 1-(3-dimethylaminopropyl)-3-ethylcarbodiimide (or hydrochloride thereof), N,N'-disuccinimidyl carbonate, benzotriazol-1-yloxytris(dimethylamino)phosphonium hexafluorophosphate, 2-(1H-benzotriazol-1-yl)-1,1,3,3-tetramethyl uronium hexafluorophosphate (i.e. O-(1H-benzotriazol-1-yl)-N,N,N',N'-tetramethyluronium hexafluorophosphate), benzotriazol-1-yloxytris-pyrrolidinophosphonium hexafluorophosphate, bromo-tris-pyrrolidinophosphonium hexafluorophosphate, 2-(1H-benzotriazol-1-yl)-1,1,3,3-tetramethyluronium tetra-fluorocarbonate, 1-cyclohexylcarbodiimide-3-propyloxymethyl polystyrene, O-(7-azabenzotriazol-1-yl)-N,N,N',N'-tetramethyluronium hexafluorophosphate, O-benzotriazol-1-yl-N,N,N',N'-tetramethyluronium hexfluoroborate), optionally in the presence of a suitable base (e.g. sodium hydride, sodium bicarbonate, potassium carbonate, pyridine, triethylamine, dimethylaminopyridine, diisopropylamine, sodium hydroxide, potassium tert-butoxide, and/or lithium diisopropylamide (or variants thereof) and an appropriate solvent (e.g. tetrahydrofurane, pyridine, toluene, dichloromethane, chloroform, acetonitrile, dimethylformamide, trifluoromethylbenzene, dioxane, or triethylamine). Such reactions can be performed in the presence of a further additive, such as 1-hydroxybenzotriazole hydrate.

The reaction mixture is stirred at low temperature or room temperature, or heated until the starting materials have been consumed. The reaction can be carried out with protecting groups present and those protecting groups may be removed after the reaction. Suitable protecting groups are known to the person skilled in the art (see T. W. Greene, "Protective Groups in Organic Synthesis," 3rd Edition, New York, 1999).

Method 2

In a second method, according to the disclosure, a compound of formula (II) wherein $R^1$, $R^2$, $R^3$, $R^4$, and n are as defined above for formula (I) and $LG_1$ is a leaving group, is reacted with a compound of formula (IVa) or (IVb), wherein $A^1$, $A^2$, and $A^3$ are as defined above for formula (I), to yield a compound of formula (Ia) or (Ib) respectively according to the disclosure as illustrated in reaction C of the scheme above (Scheme 1 and 2).

Reaction C is carried out under standard amine arylation conditions, such as those explained for step 1 of a method 1 described above (Scheme 1 and 2).

Method 3
Step 1

In a third method, according to the disclosure, a compound of formula (II) wherein, $R^1$, $R^2$, $R^3$, $R^4$, and n are as defined above for formula (I) and $LG_1$ is a leaving group, is reacted with a compound of formula (Va) or (Vb), wherein $A^1$, $A^2$, and $A^3$ are as defined above for formula (I), to yield a compound of formula (VIIa) or (VIIb) respectively according to the disclosure as illustrated in reaction D of the scheme above (Scheme 1 and 2).

Reaction D is carried out under standard amine arylation conditions such as those explained for step 1 of method 1 described above (Scheme 1 and 2).

Step 2

The ester of the compound of formula (VIIa) or (VIIb) is subsequently converted to a substituted amide group to yield the compound of formula (Ia) or (Ib) according to the disclosure as illustrated in reaction E of the schemes above (Scheme 1 and 2). Reaction E is carried out under standard amidation conditions, for example in the presence of a suitable metal or base catalyst (e.g. trimethylaluminium, antimony(III) ethoxide, indium(III) iodide, titanium(IV) isopropoxide, zirconium(IV) tert-butoxide, hafnium(IV) tert-butoxide, zinc dust, sodium methoxide, potassium methoxide, 1,8-Diazabicyclo[5.4.0]undec-7-ene, 1,3-bis(2,4,6-tri methylphenyl)-imidazolium, (PNN)Ru(II), Di-µ-chloro-bis[chloro-(pentamethylcyclopentadienyl)-iridium(III)], lanthanum(III) trifluoromethane-sulfonate, magnesium nitride), optionally in the presence of a suitable additive (e.g. 1-hydroxy-7-azabenzotriazole, 1-hydroxybenzotriazole, hydroxyproline, 4-trifluoromethylphenol) and an appropriate solvent (e.g. methanol, tetrahydrofuran, acetonitrile, 2-methyltetrahydrofuran, toluene, benzene, dichloromethane, water, chloroform dimethylformamide, or mixtures thereof) or absence of solvent. Such reactions may be performed in the presence of a further base such as potassium tert-butoxide or sodium acetate.

This reaction can be carried out under microwave irradiation reaction conditions.

Alternatively, the ester group can be transformed to the carboxylic acid group under standard condition (e.g. sodium hydroxide, lithium hydroxide, or chloridric acid), which carboxylic acid group is then converted under standard amidation conditions such as those explained for step 2 of method 1 described above (Scheme 1 and 2).

The reaction mixture is stirred at low temperature or room temperature, or heated until the starting materials have been consumed. The reaction can be carried out with protecting groups present and those protecting groups can be removed after reaction. Suitable protecting groups are known to the person skilled in the art (see T. W. Greene, "Protective Groups in Organic Synthesis," $3^{rd}$ Edition, New York, 1999).

Method 4

In another method, according to the disclosure, a compound of formula (XI) wherein $R^1$, $R^2$, $R^3$, $R^4$, and n are as defined above for formula (I) is reacted with a compound of formula (VIIIa) or VIIIb), wherein $A^1$, $A^2$, and $A^3$ are as defined above and $LG_2$ is a leaving group, to yield a compound of formula (VIa) or (VIb) as illustrated in reaction F of the scheme above (Scheme 1 and 2).

Reaction F is carried out under standard amine arylation conditions such as those explained for step 1 of method 1 described above (Scheme 1 and 2).

Method 5

In another method, according to the disclosure, a compound of formula (XI) wherein $R^1$, $R^2$, $R^3$, $R^4$, and n are as defined above for formula (I), is reacted with a compound of formula (IXa) or (IXb), wherein $A^1$, $A^2$, and $A^3$ are as defined above for formula (I) and $LG_2$ is a leaving group, to yield a compound of formula (Ia) or (Ib) respectively according to the disclosure as illustrated in reaction G of the scheme above (Scheme 1 and 2).

Reaction G is carried out under standard amine arylation conditions such as those explained for step 1 of method 1 described above (Scheme 1 and 2).

Method 6

In another method, according to the disclosure, a compound of formula (XI) wherein, $R^1$, $R^2$, $R^3$, $R^4$, and n are as defined above for formula (I), is reacted with a compound of formula (Xa) or (Xb), wherein $A^1$, $A^2$, and $A^3$ are as defined above and $LG_2$ is a leaving group, to yield a compound of formula (VIIa) or (VIIb) respectively according to the disclosure as illustrated in reaction H of the scheme above (Scheme 1 and 2).

Reaction H is carried out under standard amine arylation conditions such as those explained for step 1 of method 1 described above (Scheme 1 and 2).

Method 7

Step 1

In another method, according to the disclosure, the sulfonyl chloride of compound of formula (VIIIc) or (VIIId), wherein, $R^1$, $R^2$, $R^3$, $R^4$, and n are as defined above for formula (I), is converted to a substituted sulfonamide group to yield the compound of formula (IXc) or (IXd) according to the disclosure as illustrated in reaction I of the schemes above (Scheme 3 and 4).

Reaction I is carried out under standard coupling conditions in a suitable solvent and in the presence of a suitable base as those explained for step 2 of method 1 described above (Scheme 1 and 2).

Step 2

The compound of formula (IXc) or (IXd) is reacted with a compound of formula (XI) to yield a compound of formula (Ic) or (Id) respectively according to the disclosure as illustrated in reaction J of the scheme above (Scheme 3 and 4).

Reaction J is carried out under standard amine arylation conditions such as those explained for step 1 of a method 1 described above (Scheme 1 and 2).

Method 8

Step 1

In another method, according to the disclosure, the sulfonyl chloride of compound of formula (XIIc) or (XIId), wherein, $R^1$, $R^2$, $R^3$, $R^4$, and n are as defined above for formula (I), is converted to a substituted sulfonamide group to yield the compound of formula (XIIIc) or (XIIId) according to the disclosure as illustrated in reaction K of the schemes above (Scheme 3 and 4).

Reaction K is carried out under standard coupling conditions in a suitable solvent and in the presence of a suitable base as those explained for step 2 of method 1 described above (Scheme 1 and 2).

Step 2

The nitro group of the compound of formula (XIIIc) or (XIIId) is subsequently reduced to a primary amine group to yield the compound of formula (IVc) or (IVd) according to the disclosure as illustrated in reaction L of the scheme above (Scheme 3 and 4). Reaction L is carried out with a suitable reducing agent, such as Fe, $SnCl_2$, Raney Nickel, palladium, and $H_2/PtO_2$. The reaction can be carried out in the presence of an acid, such as acetic acid, chloridric acid, or sulfuric acid, and in a suitable solvent, such as ethyl acetate, water, methanol, ethanol, and/or tetrahydrofuran. Other reducing agents or acids can be employed, as are known by the person skilled in the art. The reaction mixture is stirred at room temperature, or heated until the starting materials have been consumed. The reaction can be carried out with protecting groups present and those protecting groups may be removed after the reaction. Suitable protecting groups are known to the person skilled in the art (see T. W. Greene, "Protective Groups in Organic Synthesis," 3rd Edition, New York, 1999).

Step 3

The compound of formula (IVc) or (IVd) is reacted with a compound of formula (II) to yield a compound of formula (Ic) or (Id) respectively according to the disclosure as illustrated in reaction M of the scheme above (Scheme 3 and 4).

Reaction M is carried out under standard amine arylation conditions, such as those explained for step 1 of a method 1 described above (Scheme 1 and 2).

Method 9

Step 1

In another method, according to the disclosure, the nitro group of compound of formula (XIVa) or (XIVb) wherein, $R^1$, $R^2$, $R^3$, $R^4$, and n are as defined above for formula (I), is reduced to an amine group to yield the compound of formula (XVc) or (XVd) according to the disclosure as illustrated in reaction N of the schemes above (Scheme 5 and 6).

Reaction N is carried out under standard reducing conditions in a suitable solvent and in the presence of a suitable reducing agent as those explained for step 2 of method 8 described above (Scheme 3 and 4).

Step 2

The compound of formula (XVc) or (XVd) is reacted with a compound of formula (II) to yield a compound of formula (XVIc) or (XVId) respectively according to the disclosure as illustrated in reaction O of the scheme above (Scheme 5 and 6).

Reaction O is carried out under standard amine arylation conditions such as those explained for step 1 of a method 1 described above (Scheme 1 and 2).

Step 3

The sulfonic acid group of the compound of formula (XVIc) or (XVId) is subsequently transformed to a sulfonyl chloride group to yield the compound of formula (VIc) or (VId) according to the disclosure as illustrated in reaction P of the scheme above (Scheme 5 and 6). Reaction P is carried out with a suitable chlorinated agent, such as $POCl_5$, $POCl_3$, $SOCl_2$, $ClSO_3H$, oxalyl dichloride, cyanuric trichloride, or N-chlorosuccinimide. The reaction can be carried out in the presence of an additive, such as 18-crown-6, or suitable base, such as sodium hydroxide or pyridine. The reaction can be carried out in a suitable solvent, such as dichloromethane, dimethylformamide, acetone, and/or carbon tetrachloride (or mixture thereof). Other chlorinated agents, bases, or additives may be employed, as is known by the person skilled in the art. The reaction mixture is stirred at room temperature, or heated until the starting materials have been consumed. The reaction can be carried out with protecting groups present and those protecting groups can be removed after the reaction. Suitable protecting groups are known to the person skilled in the art (see T. W. Greene, "Protective Groups in Organic Synthesis," 3rd Edition, New York, 1999).

Step 4

The sulfonyl chloride group of compound of formula (VIc) or (VId) is transformed to a substituted sulfonamide to yield compound of formula (Ic) or (Id) respectively according to the disclosure as illustrated in reaction Q of the scheme above (Scheme 5 and 6).

Reaction Q is carried out under standard coupling conditions in a suitable solvent and in the presence of a suitable base as those explained for step 2 of method 1 described above (Scheme 1 and 2).

Method 10

In another method, according to the disclosure, the compound of formula (XVIIc) or (XVIId) is reacted with a compound of formula (XI) to yield a compound of formula (XVIc) or (XVId) respectively according to the disclosure as illustrated in reaction R of the scheme above (Scheme 5 and 6).

Reaction R is used to prepare compounds of formula (XVIc) or (XVId) by reaction of a compound of formula (XVIIc) or (XVIId) with a compound of formula (XI) wherein $LG_2$ represents a leaving group, such as iodo, bromo, chloro or a sulphonate group (e.g., —$OS(O)_2CF_3$, —$OS(O)_2CH_3$, or —$OS(O)_2PhMe$). Said reaction can be performed under standard conditions in the presence of a suitable base, such as sodium hydroxide, disodium carbonate or sodium bicarbonate. The reaction can be carried out in the presence of a catalyst or additive, such as copper iodide, magnesium oxide, thiourea, or hydrazine. The reaction can be carried out in a suitable solvent, such as water, ethanol, methanol, or a mixture thereof. Other bases, catalysts, or additives can be employed, as is known by the person skilled in the art. The reaction mixture is stirred at low temperature, room temperature, or heated until the starting materials have been consumed. The reaction can be carried out with protecting groups present and those protecting groups can be removed after the reaction. Suitable protecting groups are known to the person skilled in the art (see T. W. Greene, "Protective Groups in Organic Synthesis," 3rd Edition, New York, 1999).

Use of the Compounds of the Disclosure

Compounds of the Disclosure have the ability to bind allosterically to mutated β-galactosidase enzyme and, thereby, stabilizing the enzyme against denaturation. Therefore Compounds of the Disclosure can be used/administered to treat and/or prevent conditions associated with the alteration of the activity of β-galactosidase, specifically galactosidase β-1 or GLB1, including GM1 gangliosidoses and Morquio syndrome, type B, in a patient suffering from said condition.

Accordingly, the present disclosure is directed to a method of treating or preventing a condition associated with the alteration of the activity of GLB1 in a patient, comprising administering to the patient in need thereof an effective amount of a compound of any one of formulae (I) or (IA), or a pharmaceutically acceptable salt or solvate thereof.

The present disclosure is also directed to a method of treating GM1 ganglisidosis or Morquio B syndrome in a patient, comprising administering to the patient in need thereof an effective amount of a compound of any one of formulae (I) or (IA), or a pharmaceutically acceptable salt or solvate thereof. In one embodiment, the method of treating GM1 ganglisidosis or Morquio B syndrome in a patient further comprises administering to the patient an effective amount of an enzyme for enzyme replacement therapy. In another embodiment, the enzyme is β-galactosidase or an analog thereof. In another embodiment, the method further comprises administering to the patient a small molecule chaperone. In one embodiment, the small molecule chaperone binds competitively to an enzyme. In another embodiment, the small molecule chaperone is selected from the group consisting of iminoalditols, iminosugars, aminosugars, thiophenylglycosides, glycosidase, sulfatase, glycosyl transferase, phosphatase, and peptidase inhibitors. In another embodiment, suitable small molecule chaperones are selected from the group consisting of 1-deoxygalactonojirimycin (DGJ), N-nonyldeoxynojirimycin (NN-DNJ), N-butyldeoxygalactonojirimycin (NB-DGJ), galactose, fluorous iminoalditol, and epi-isofagomine.

The present disclosure is also directed to a method of increasing β-galactosidase activity in a patient in need thereof, comprising administering to the patient an effective amount of a compound of any one of defined formulae (I) or (IA), or a pharmaceutically acceptable salt or solvate thereof.

The present disclosure is also directed to the use of a compound represented by any of defined formulae (I) or (IA), or a pharmaceutically acceptable salt or solvate thereof, in the manufacture of a medicament for treating and/or preventing a condition associated with the alteration of the activity of β-galactosidase, specifically galactosidase β-1 or GLB1, including GM1 gangliosidoses and Morquio syndrome, type B, in a patient suffering from said condition.

The present disclosure is also directed to a compound of any one of formulae (I) or (IA), or a pharmaceutically acceptable salt or solvate thereof, for use in treating GM1 ganglisidosis or Morquio B syndrome in a patient. In one embodiment, the compound of any one of formulae (I) or (IA), or a pharmaceutically acceptable salt or solvate thereof, is administered to the patient in combination with an effective amount of an enzyme for enzyme replacement therapy. In another embodiment, the enzyme is β-galactosidase or an analog thereof. In another embodiment the compound of any one of formulae (I) or (IA), or a pharmaceutically acceptable salt or solvate thereof, is administered to the patient in combination with a small molecule chaperone. In one embodiment, the small molecule chaperone binds competitively to an enzyme. In another embodiment, the small molecule chaperone is selected from the group consisting of iminoalditols, iminosugars, aminosugars, thiophenylglycosides, glycosidase, sulfatase, glycosyl transferase, phosphatase, and peptidase inhibitors. In another embodiment, suitable small molecule chaperones are selected from the group consisting of 1-deoxygalactonojirimycin (DGJ), N-nonyldeoxynojirimycin (NN-DNJ), N-butyldeoxygalactonojirimycin (NB-DGJ), galactose, fluorous iminoalditol, and epi-isofagomine.

Figure 1B:
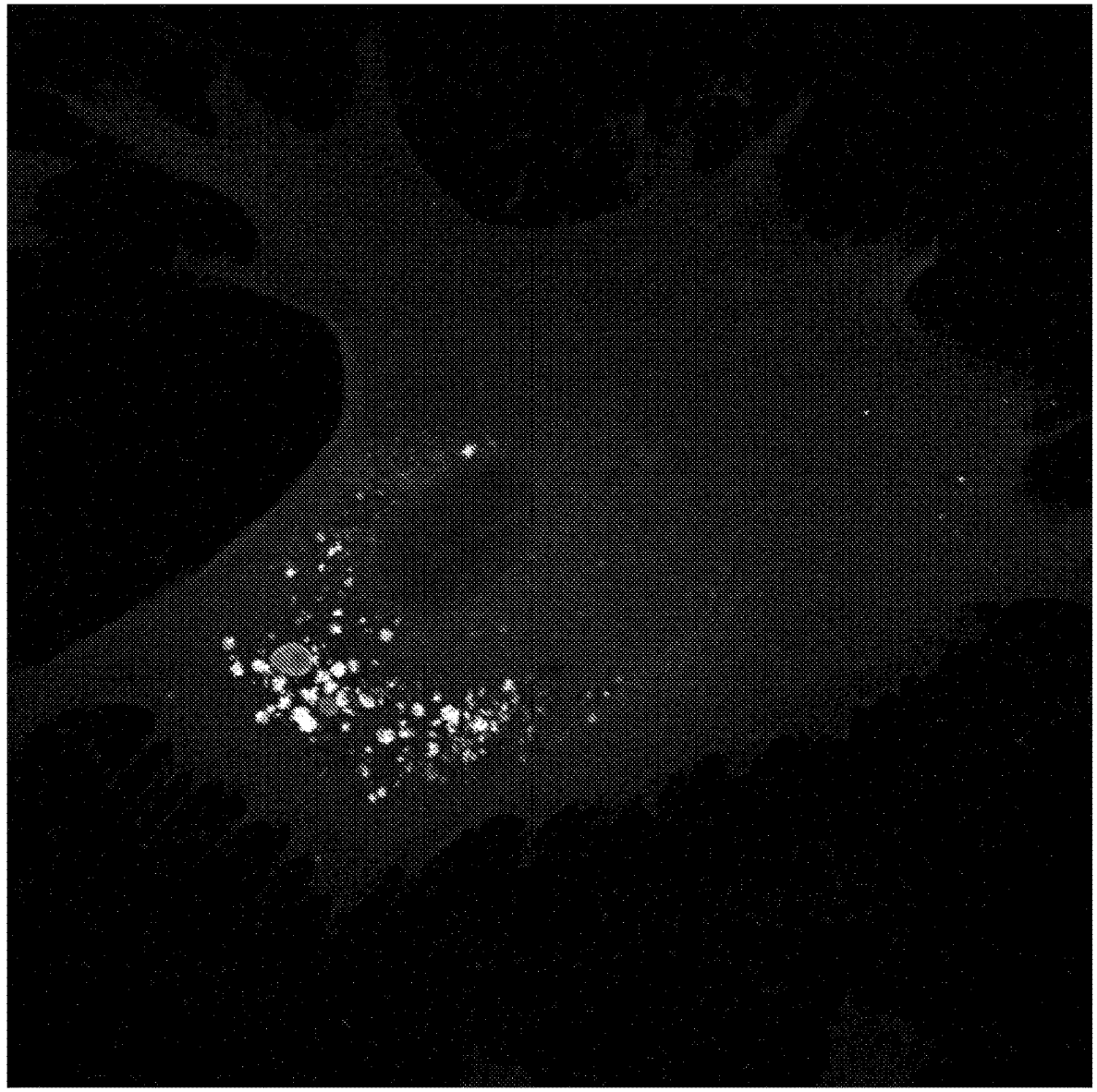
Figure 2A:
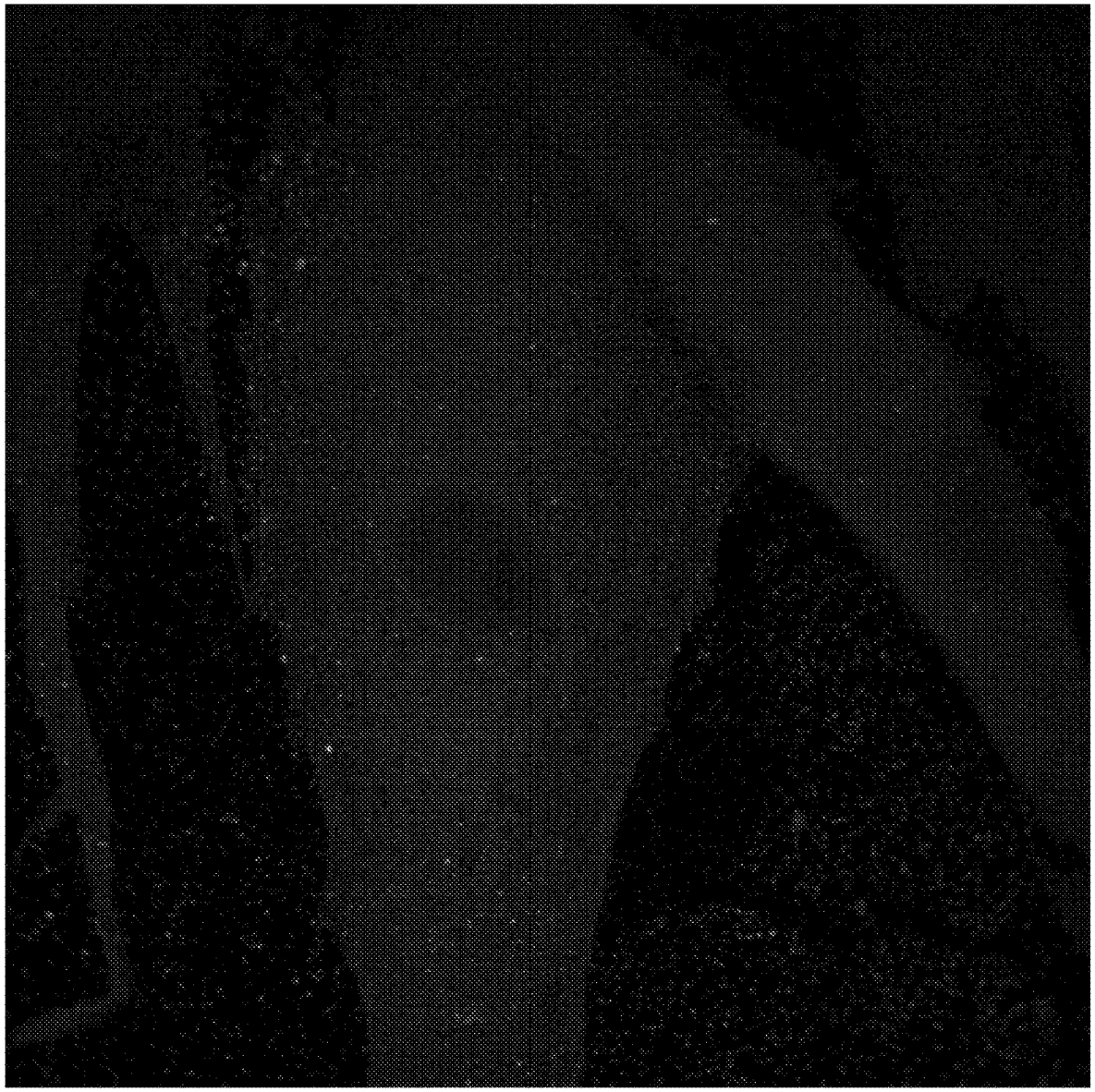
FIGS. 2A and 2B show reduction of GM1 ganglioside accumulation in GM11473 cells treated with a Compound of the Disclosure at 50 µM.
Figure 2B:
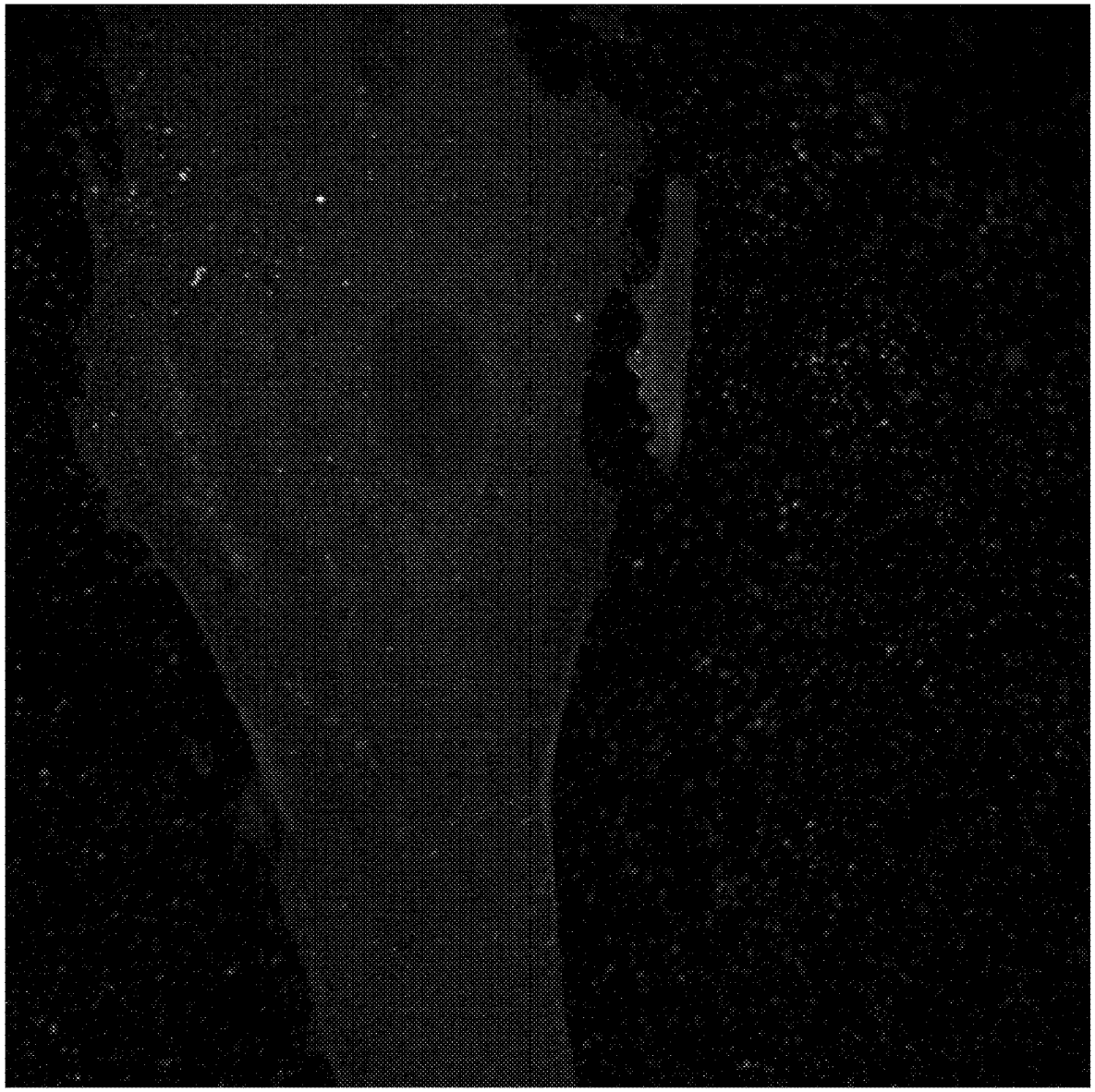

As shown in FIGS. 1A, 1B, 2A, and 2B, GM1 ganglioside content was reduced in GM11473 fibroblasts after treatment with a Compound of the Disclosure (as it is shown in FIGS. 2A and 2B) compared with cells cultured in the absence of a Compound of the Disclosure (as it is shown in FIGS. 1A and 1B). FIGS. 1A and 1B show accumulation of of GM1 ganglioside in GM11473 untreated cells in two separate fluorescence images for the same sample set (white color shows accumulation of GM1 ganglioside). FIGS. 2A and 2B show a reduction of GM1 ganglioside accumulation in GM11473 cells treated with a Compound of the Disclosure at 50 µM in two separate fluorescence images for the same sample set (white color shows accumulation of GM1 ganglioside). Accordingly, Compounds of the Disclosure show efficacy in the treatment and/or prevention of conditions associated with the alteration of the activity of β-galactosidase, specifically galactosidase β-1 or GLB1, because they reduce the accumulation of GM1 ganglioside.

Pharmaceutical Compositions

Due to their activity, the Compounds of the Disclosure can be used in human medicine. As described above, the Compounds of the Disclosure are useful for treating or preventing a condition associated with the alteration of the activity of β-galactosidase. The Compounds of the Disclosure can be administered to any patient suffering said condition. The term "patient" as used herein refers to any human that may experience the beneficial effects of a Compound of the Disclosure.

When administered to a patient, a Compound of the Disclosure can be administered as a component of a composition that comprises a pharmaceutically acceptable excipient or carrier.

The Compound of the Disclosure can be administered in combination with at least one other therapeutic agent. In one embodiment, the therapeutic agent comprises an enzyme for enzyme replacement therapy. In another embodiment, the therapeutic agent comprises a small molecule chaperone. Administration of the Compound of the Disclosure with at least one other therapeutic agent can be sequential or concurrent. In one embodiment, the Compound of the Invention and the at least one other therapeutic agent are administered in separate dosage forms. In another embodiment, the Compound of the Invention and the at least one other therapeutic agent are administered concurrently in the same dosage form.

The term "excipient" refers to a vehicle, diluent, or adjuvant that is administered with the active ingredient. Such pharmaceutical excipients can be sterile liquids, such as water and oils, including those of petroleum, animal, vegetable, or synthetic origin, such as peanut oil, soybean oil, mineral oil, sesame oil, and similar. Water or saline aqueous solutions and aqueous dextrose and glycerol solutions, for example, for injectable solutions, may be used as vehicles. Suitable pharmaceutical vehicles are described in "Remington's Pharmaceutical Sciences" by E. W. Martin, 21$^{st}$ Edition, 2005; or "Handbook of Pharmaceutical Excipients," Rowe C. R.; Paul J. S.; Marian E. Q., sixth Edition, incorporated herein by reference.

Examples of pharmaceutical compositions include any solid composition (tablets, pills, capsules, granules, etc.) or liquid compositions (solutions, suspensions, or emulsions) for oral, topical, or parenteral administration.

In another embodiment, the pharmaceutical compositions are in an oral delivery form. Pharmaceutical forms suitable for oral administration can be tablets and capsules, and can contain conventional excipients known in the art, such as binders, for example syrup, gum Arabic, gelatin, sorbitol, tragacanth, or polyvinylpyrrolidone; fillers, for example lactose, sugar, cornstarch, calcium phosphate, sorbitol, or glycine; lubricants for the preparation of tablets, for example magnesium stearate; disintegrants, for example starch, polyvinylpyrrolidone, sodium starch glycolate, or microcrystalline cellulose; or pharmaceutically acceptable wetting agents, such as sodium lauryl sulphate.

Solid oral compositions can be prepared by conventional methods of blending, filling, or preparation of tablets. Repeated blending operations can be used to distribute the active ingredient in all the compositions that use large amounts of fillers. Such operations are conventional in the art. The tablets can be prepared, for example, by dry or wet granulation and optionally can be coated by well known methods in normal pharmaceutical practice, in particular using enteric coating.

Pharmaceutical compositions can also be adapted for parenteral administration, such as sterile solutions, suspensions, or lyophilized products in the appropriate unit dosage form. Suitable excipients, such as fillers, buffering agents, or surfactants can be used.

The mentioned formulations can be prepared using standard methods, such as those described or referred to in the Spanish and U.S. Pharmacopoeias and similar reference texts.

In general, the effective amount of a Compound of the Disclosure to be administered depends on the relative efficacy of the compound chosen, the severity of the condition or disorder being treated, and the patient's weight. The active compound can be administered one or more times a day, for example 1, 2, 3, or 4 times daily, with typical total daily doses in the range from about 0.01 mg/kg of body weight/day to about 1000 mg/kg of body weight/day. In another embodiment, the effective dosage amount of a Compound of the Disclosure is about 500 mg/kg of body weight/day or less. In another embodiment, the effective dosage amount of a Compound of the Disclosure is about 100 mg/kg of body weight/day or less. In another embodiment, the effective dosage amount ranges from about 0.01 mg/kg of body weight/day to about 100 mg/kg of body weight/day of a Compound of the Disclosure; in another embodiment, from about 0.02 mg/kg of body weight/day to about 50 mg/kg of body weight/day of a Compound of the Disclosure; and in another embodiment, from about 0.025 mg/kg of body weight/day to about 20 mg/kg of body weight/day of a Compound of the Disclosure.

A composition of the disclosure can be prepared by a method comprising admixing a Compound of the Disclosure with a pharmaceutically acceptable excipient or carrier. Admixing can be accomplished using methods known for admixing a compound and a pharmaceutically acceptable excipient or carrier. In another embodiment, the Compound of the Disclosure is present in the composition in an effective amount.

The following examples are illustrative, but not limiting, of the compounds, compositions and methods of the present disclosure. Suitable modifications and adaptations of the variety of conditions and parameters normally encountered in clinical therapy and which are obvious to those skilled in the art in view of this disclosure are within the spirit and scope of the disclosure.

General Experimental Conditions

The compound IUPAC names given herein were generated with ChemBioDraw Ultra 12.0. or 12.0.2.

Hereinafter, the term "h" means hours, "eq" means equivalents, "min" means minutes, "$Pd_2(dba)_3$" means tris(dibenzylideneacetone)-dipalladium(0), "XantPhos" means 4,5-Bis(diphenylphosphino)-9,9-dimethylxanthene, "$SnCl_2$" means tin(II) chloride, "HATU" means 1-[Bis(dimethylamino)methylene]-1H-1,2,3-triazolo[4,5-b]pyridinium 3-oxid hexafluorophosphate, "TBTU" O-(Benzotriazol-1-yl)-N,N,N',N'-tetramethyluronium tetrafluoroborate, "TLC" means thin layer chromatography, "HPLC" means high-performance liquid chromatography, and "LC-MS" means liquid chromatography-mass spectrometry.

NMR spectra were recorded in a Varian Mercury 400 MHz spectrometer (at room temperature).

The HPLC measurements were performed using a HPLC Waters Alliance HT comprising a pump (Edwards RV12) with degasser, an autosampler, a diode array detector, and a column as specified in the respective methods below. Flow from the column was split to a MS spectrometer. The MS detector was configured with an eletrospray ionization source (micromass ZQ4000), Nitrogen was used as the nebulizer gas. Data acquisition was performed with MassLynx software.

LC-MS analysis of the compounds was conducted as per one of the following methods.

Method A. Column: Agilent Zorbax 3.5 μm, SB—C8 (4.6× 75 mm); wavelength: 210/254 nm; flow: 1 mL/min; run time: 7 min; Time & mobile phase-gradient (time in min/B): 0/5, 3.5/90, 5/90, 5.5/5, 7/5 [B: acetonitrile; A: formic acid (0.1% in water)]; MASS: Agilent-single quad-multimode-APCI-ESI.

Method B. Column: Agilent Zorbax 3.5 μm, SB—C8 (4.6× 75 mm); wavelength: 210/254 nm; flow: 1 mL/min; run time: 7 min; Time & mobile phase-gradient (time in min/B): 0/30, 3.5/95, 5/95, 5.5/30, 7/30 [B: acetonitrile; A: formic acid (0.1% in water)]; MASS: Agilent-single quad-multimode-APCI-ESI.

Method C. Column: Agilent Zorbax 3.5 μm, SB—C8 (4.6× 75 mm); wavelength: 210/254 nm; flow: 1 mL/min; run time: 7.0 min; Time & mobile phase-gradient (time in min/B): 0/30, 3.5/95, 5/95, 5.5/30, 7/30 [B: acetonitrile; A: 10 mM ammonium acetate]; MASS: Agilent-single quad-multimode-APCI-ESI.

Method D. Column: Agilent Eclipse XDB C-18 Column (4.6×100 mm) 3.5 micron; wavelength: 210/254 nm; flow: 1 mL/min; run time: 8 min; Time & mobile phase-gradient (time in min/B): 0/10, 2/10, 3/90, 6/90, 6.5/10, 8/10 [B: acetonitrile; A: formic acid (0.1% in water)]; LC/MS/MS module Applied Biosystems-API-2000 with Agilent LC.

Method E. Column: Waters Symmetry C-18 Column (4.6× 75 mm) 3.5 micron, flow 1 mL/min, run time: 5 min, Time & mobile phase-isocratic (time in min/B): 0/80, 5/80 [B: acetonitrile, A: formic acid (0.1% in water)]; LC/MS/MS Module Applied Biosystem-API 3200 with Shimadzu LC.

Method F. Direct mass: Time & mobile phase-isocratic (time in min/B) using union: 0/80, 1/80 [B: acetonitrile, A: formic acid (0.1% in water)]; LC/MS/MS module Applied Biosystems-API-2000 with Agilent LC.

Method G. Column: Waters Symmetry C-18 Column (4.6× 75 mm) 3.5 micron, flow 1 mL/min, run time: 5 min, Time & mobile phase-isocratic (time in min/B): 0/80, 5/80 [B: acetonitrile, A: formic acid (0.1% in water)]; LC/MS/MS Module Applied Biosystem-API 3200 with Shimadzu LC.

MW calculated is an isotopic average and the "found mass" is referring to the most abundant isotope detected in the LC-MS.

General Procedure I

Following procedure D, as those described in Schemes 1 or 2, compounds of formulae (VIIa) or (VIIb) can be prepared in the conditions described below:

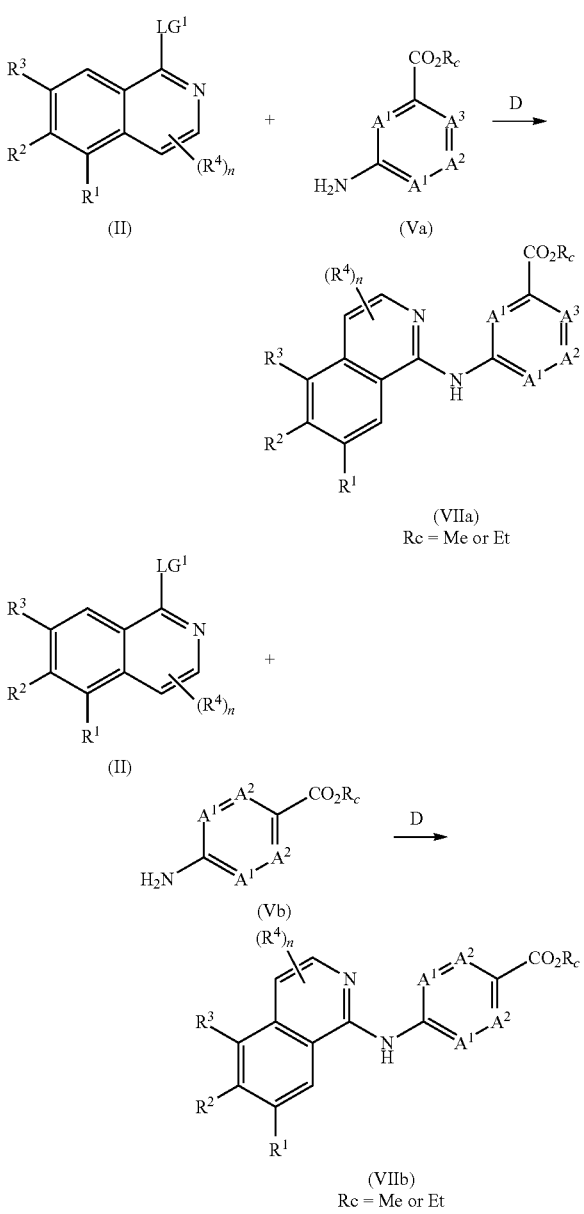

A mixture of the appropriate chloride (II) (ex: 1,7-dichloroisoquinoline) (1 eq), the appropriate amine (Va) or (Vb) (ex: methyl 5-aminopicolinate) (1-1.5 eq), Pd$_2$(dba)$_3$ (0.05-0.1 eq), XantPhos (0.2 eq), and cesium carbonate (2 eq) in 1,4-dioxane (5.3 mL/mmol) (pre-degasified) was heated at 130-140° C. for 2-5 h under nitrogen atmosphere. The mixture was cooled to room temperature and filtered through a celite pad. The filtrate was concentrated under vacuum to minimum volume and was diluted with water (50 mL), and extracted in ethyl acetate. The combined organic phase was further washed with water followed by brine solution, dried over anhydrous sodium sulphate, and concentrated. The product was taken to the next step without any further purification. Alternatively, the residue was purified by flash column chromatography (dichloromethane/methanol or hexanes/ethyl acetate) to obtain the desired product (VIIa) or (VIIb) (ex: methyl 5-((7-chloroisoquinolin-1-yl)amino)picolinate).

Intermediate 1

Methyl
5-((7-chloroisoquinolin-1-yl)amino)picolinate

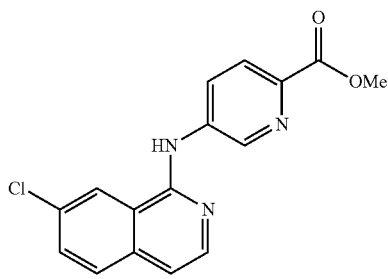 [SMILES: COC(=O)c1ccc(Nc2nccc3ccc(Cl)cc23)cn1]

Yield: 76%.
ES-MS [M+H]$^+$: 314.0; $t_R$=3.64 min (Method B).

Intermediate 2

Ethyl
5-((7-methoxyisoquinolin-1-yl)amino)picolinate

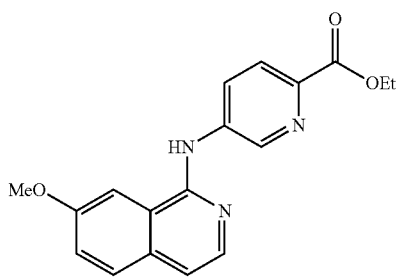 [SMILES: CCOC(=O)c1ccc(Nc2nccc3ccc(OC)cc23)cn1]

Crude Yield: 95%.
ES-MS [M+H]$^+$: 310.0; $t_R$=3.63 min (Method A).

Intermediate 3

Methyl
6-((7-chloroisoquinolin-1-yl)amino)nicotinate

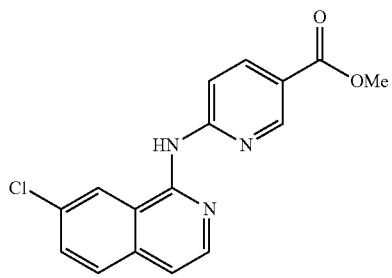 [SMILES: COC(=O)c1ccc(Nc2nccc3ccc(Cl)cc23)nc1]

Yield: 95%.
ES-MS [M+H]$^+$: 314.0; $t_R$=2.32 min (Method B).

Intermediate 4

Methyl
4-((7-chloroisoquinolin-1-yl)amino)picolinate

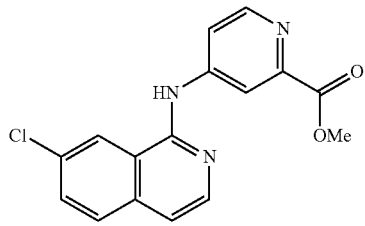 [SMILES: COC(=O)c1cc(Nc2nccc3ccc(Cl)cc23)ccn1]

Yield: 57.8%.
ES-MS [M+H]$^+$: 314.0; $t_R$=3.74 min (Method A).

Intermediate 5

Methyl
4-((7-methoxyisoquinolin-1-yl)amino)picolinate

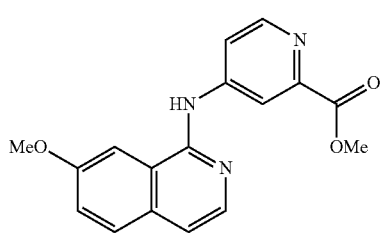 [SMILES: COC(=O)c1cc(Nc2nccc3ccc(OC)cc23)ccn1]

Yield: 25%.
ES-MS [M+H]$^+$: 310.1; $t_R$=1.99 min (Method B).

Intermediate 6

Methyl 5-((7-cyanoisoquinolin-1-yl)amino)picolinate

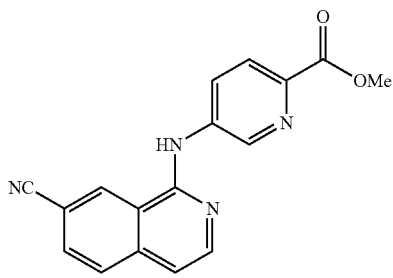 [SMILES: COC(=O)c1ccc(Nc2nccc3ccc(C#N)cc23)cn1]

Yield: 53%.
ES-MS [M+H]$^+$: 305.1; $t_R$=4.06 min (Method A).

Intermediate 7

Methyl 5-((5-chloroisoquinolin-1-yl)amino)picolinate

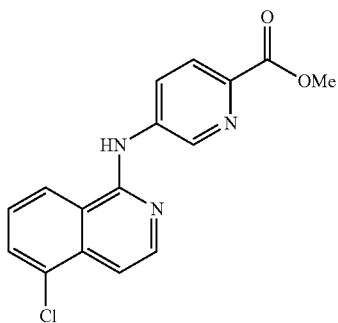 [SMILES: COC(=O)c1ccc(Nc2nccc3c(Cl)cccc23)cn1]

Yield: 29%.
ES-MS [M+H]$^+$: 314.1; $t_R$=4.36 min (Method A).

Intermediate 8

Methyl 4-((7-chloroisoquinolin-1-yl)amino)benzoate

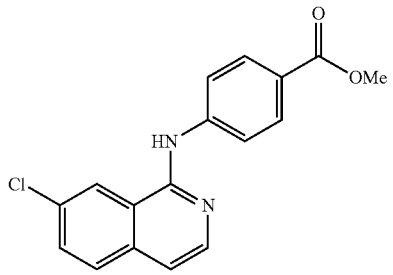 [SMILES: COC(=O)c1ccc(Nc2nccc3ccc(Cl)cc23)cc1]

Yield: 56%.
ES-MS [M+1]$^+$: 313.0; $t_R$=4.87 min (Method A).

Intermediate 9

Ethyl 3-((7-chloroisoquinolin-1-yl)amino)benzoate

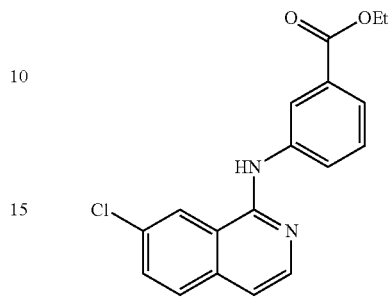

Yield: 65%.
ES-MS [M+1]$^+$: 327.0; $t_R$=4.0 min (Method B).

General Procedure II:

Following procedure E as those described in Schemes 1 or 2 compounds of formulae (VIa) or (VIb) can be prepared in the conditions described below:

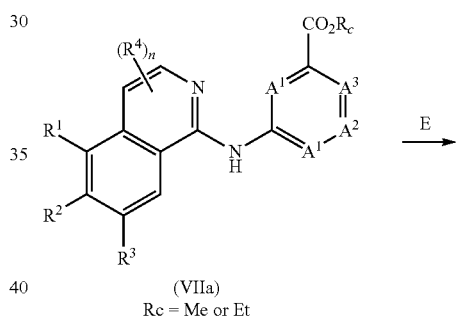

(VIIa)
Rc = Me or Et

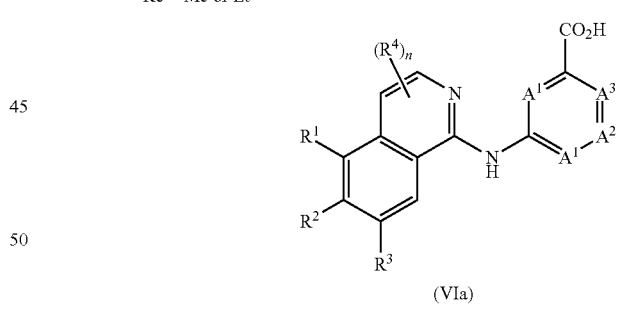

(VIa)

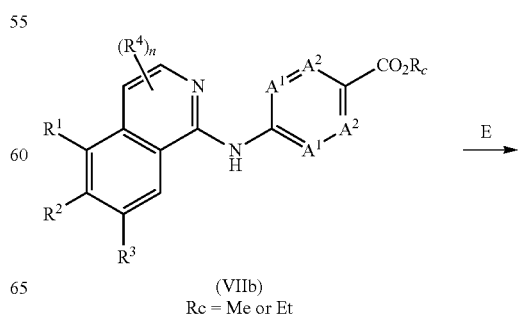

(VIIb)
Rc = Me or Et

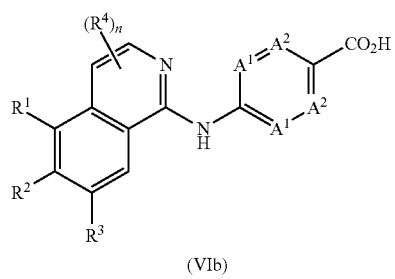

(VIb)

A solution of lithium hydroxide (3-5 eq) in water (10%) (3-5 eq of sodium hydroxide can be used) was added to a solution of the appropriate ester (VIIa) or (VIIb) (ex: Ethyl 3-((7-chloroisoquinolin-1-yl)amino)benzoate) (1 eq) in methanol. The reaction mixture was stirred at room temperature for 2-10 h (in some cases it was necessary to heat at 90° C.). After consumption of starting materials, the reaction mixture was filtered and the methanol was evaporated under vacuum. The aqueous solution was acidified with 1 N hydrochloric acid or glacial acetic acid (pH ~5-6) and the resulting suspension was filtered; washed with water and vacuum dried to afford the desired carboxylic acid product (VIa) or (VIb) (ex: 3-(7-chloro-isoquinolin-1-ylamino)-benzoic acid). The neutralized mixture could also be extracted with tetrahydrofuran (×2) and washed with water.

Intermediate 10

3-(7-Chloro-isoquinolin-1-ylamino)-benzoic acid

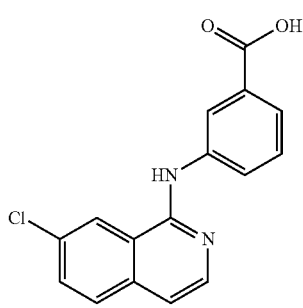 [SMILES: O=C(O)c1cccc(Nc2nccc3ccc(Cl)cc23)c1]

Yield: 93%.

ES-MS [M−1]⁻: 297.3; $t_R$=0.88 min (Method E).

¹H NMR (400 MHz, DMSO-d₆) δ: 12.90 (brs, 1H), 9.41 (s, 1H), 8.75 (s, 1H), 8.45 (t, J=2.0 Hz, 1H), 8.24 (dd, J=8.4, 2.0 Hz, 1H), 8.06 (d, J=5.6 Hz, 1H), 7.90 (d, J=8.4 Hz, 1H), 7.76 (dd, J=8.8, 1.6 Hz, 1H), 7.58 (d, J=7.6 Hz, 1H), 7.45 (dd, J=8.0, 7.6 Hz, 1H), 7.26 (d, J=6.0 Hz, 1H).

Intermediate 11

4-((7-Chloroisoquinolin-1-yl)amino)benzoic acid

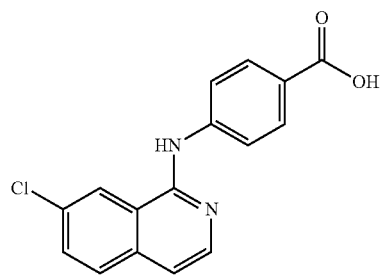 [SMILES: O=C(O)c1ccc(Nc2nccc3ccc(Cl)cc23)cc1]

Longer reaction time was needed: refluxed for 24 h.

Yield: 16%.

ES-MS [M+1]⁺: 299.0; $t_R$=3.77 min (Method B).

Intermediate 12

5-((5-Chloroisoquinolin-1-yl)amino)picolinic acid

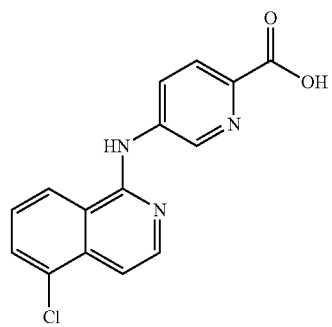 [SMILES: O=C(O)c1ccc(Nc2nccc3c(Cl)cccc23)cn1]

Yield: 79%.

ES-MS [M−H]⁻: 298.0; $t_R$=3.6 min (Method B).

Intermediate 13

5-((7-Chloroisoquinolin-1-yl)amino)picolinic acid

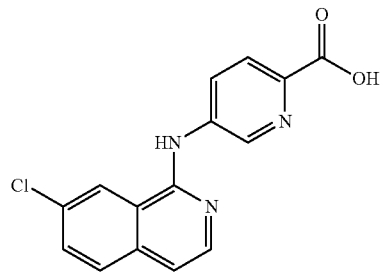 [SMILES: O=C(O)c1ccc(Nc2nccc3ccc(Cl)cc23)cn1]

Yield: 49%.

ES-MS [M+H]⁺: 300.0; $t_R$=2.56 min (Method B).

Intermediate 14

6((7-Chloroisoquinolin-1-yl)amino)nicotinic acid

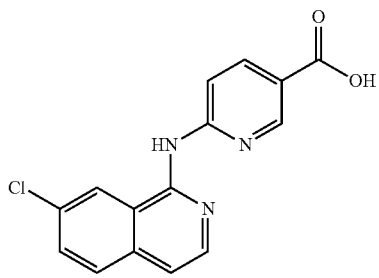 [SMILES: O=C(O)c1ccc(Nc2nccc3ccc(Cl)cc23)nc1]

Yield: 49%.
ES-MS [M+H]$^+$: 300.0; $t_R$=1.64 min (Method B).

Intermediate 15

5-((7-Methoxyisoquinolin-1-yl)amino)picolinic acid

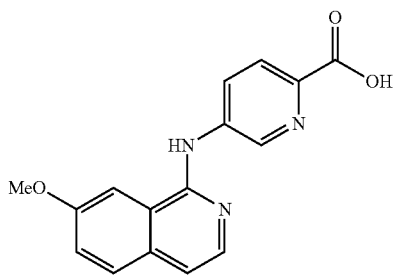 [SMILES: COc1ccc2ccnc(Nc3ccc(C(=O)O)nc3)c2c1]

Yield: 72% over 2 steps.
ES-MS [M+H]$^+$: 296.0; $t_R$=3.12 min (Method A).

Intermediate 16

5-((7-Cyanoisoquinolin-1-yl)amino)picolinic acid

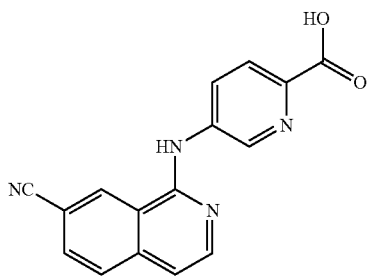 [SMILES: N#Cc1ccc2ccnc(Nc3ccc(C(=O)O)nc3)c2c1]

Yield: 78%.
ES-MS [M−H]$^-$: 289.0; $t_R$=3.34 min (Method A).

Intermediate 17

4-((7-Chloroisoquinolin-1-yl)amino)picolinic acid

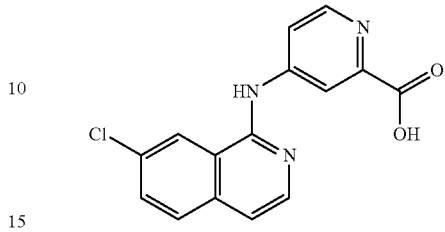

Yield: 88%.
ES-MS [M+H]$^+$: 300.0; $t_R$=1.95 min (Method B).

Intermediate 18

4-((7-Methoxyisoquinolin-1-yl)amino)picolinic acid

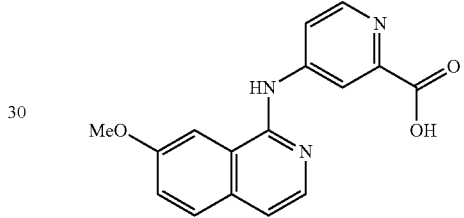

Yield: 90%.
ES-MS [M+H]$^+$: 296.1; $t_R$=1.65 min (Method B).

General Procedure III:

Following procedure B as those described in Schemes 1 or 2 compounds of formulae (Ia) or (Ib) can be prepared in the conditions described below:

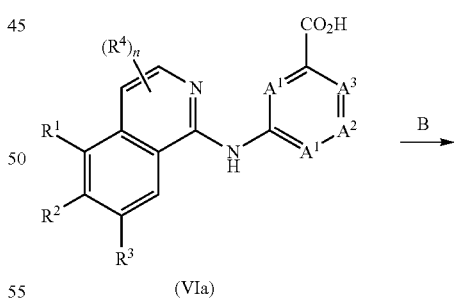

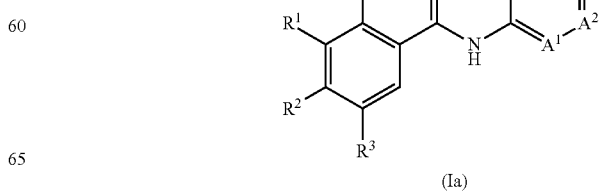

-continued

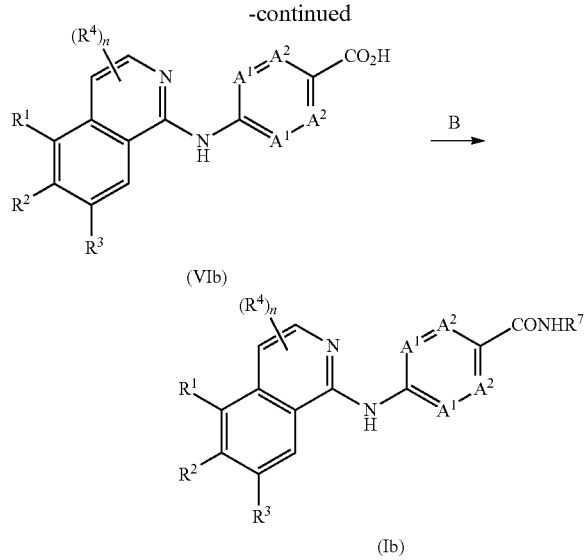

A solution of the appropriate acid chloride [prepared by stirring the corresponding acid (VIa) or (VIb) (ex: 3-(7-chloro-isoquinolin-1-ylamino)-benzoic acid) (1 eq) and oxalyl chloride (3 eq) in dichloromethane with catalytic amount of dimethylformamideat room temperature for 2 h] in acetonitrile was added drop wise to a cooled solution of the appropriate amine (1-methyl-1H-benzo[d][1,2,3]triazol-5-amine) (4 eq) and pyridine (3 eq) in acetonitrile (10 mL/mmol). The mixture was stirred at 0-5° C. for 1.5-2 h. After consumption of the starting materials, the reaction mixture was concentrated to remove the acetonitrile and then diluted with water and extracted in ethyl acetate (2×). The combined organic extract was washed with brine solution followed by water and the resulting organic layer was dried over anhydrous sodium sulphate and concentrated. The crude was purified by flash column chromatography (ethyl acetate/hexanes) to afford desired amide compound (Ia) or (Ib) (ex: 3-((7-chloroisoquinolin-1-yl)amino)-N-(1-methyl-1H-benzo[d][1,2,3]triazol-5-yl)benzamide (Example 1)).

EXAMPLE 1

3-((7-Chloroisoquinolin-1-yl)amino)-N-(1-methyl-1H-benzo[d][1,2,3]triazol-5-yl)benzamide

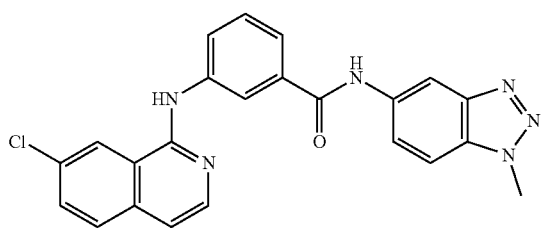 [SMILES: Cn1nnc2cc(NC(=O)c3cccc(Nc4nccc5ccc(Cl)cc45)c3)ccc21]

Yield: 9%.
ES-MS [M+H]$^+$: 429.5; $t_R$=0.86 min (Method E).
$^1$H NMR (400 MHz, DMSO-d$_6$) δ: 10.47 (s, 1H), 9.50 (s, 1H), 8.77 (s, 1H), 8.48 (s, 1H), 8.25 (d, J=8.0 Hz, 1H), 8.06 (d, J=6.0 Hz, 1H), 7.96-7.90 (m, 2H), 7.78-7.72 (m, 2H), 7.64-7.51 (m, 3H), 7.28 (d, J=5.6 Hz, 1H), 4.34 (s, 3H).

EXAMPLE 2

3-((7-Chloroisoquinolin-1-yl)amino)-N-(2-morpholino-2-(pyridin-2-yl)ethyl)benzamide

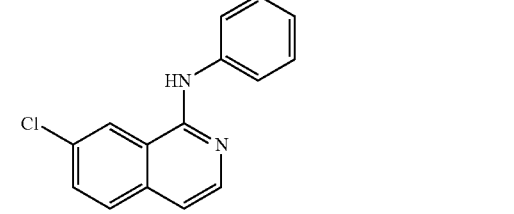

Purified by flash column chromatography (methanol/dichloromethane), Yield: 22%.
ES-MS [M+H]$^+$: 488.3; $t_R$=1.11 min (Method E).
$^1$H NMR (400 MHz, DMSO-d$_6$) δ: 9.37 (s, 1H), 8.73 (s, 1H), 8.58 (d, J=4.4 Hz, 1H), 8.24 (s, 2H), 8.04 (m, 2H), 7.89 (d, J=8.8 Hz, 1H), 7.77 (m, 2H), 7.37 (m, 3H), 7.30 (m, 1H), 7.24 (d, J=5.6 Hz, 1H), 3.95 (m, 2H), 3.69 (m, 1H), 3.53 (m, 4H), 2.55 (m, 4H).

EXAMPLE 3

3-((7-Chloroisoquinolin-1-yl)amino)-N-((2,3-dihydrobenzo[b][1,4]dioxin-6-yl)methyl)benzamide Purified by flash column chromatography (ethyl acetate/hexanes), Yield: 38%.
ES-MS [M+H]$^+$: 446.3; $t_R$=0.90 min (Method E).
$^1$H NMR (400 MHz, DMSO-d$_6$) δ: 9.39 (s, 1H), 8.92 (t, J=5.6 Hz, 1H), 8.74 (s, 1H), 8.27 (s, 1H), 8.13 (d, J=8.0 Hz, 1H), 8.04 (d, J=5.6 Hz, 1H), 7.89 (d, J=8.8 Hz, 1H), 7.75 (dd, J=8.8, 2.0 Hz, 1H), 7.50 (d, J=7.6 Hz, 1H), 7.41 (dd, J=8.0, 7.6 Hz, 1H), 7.24 (d, J=5.6 Hz, 1H), 6.80 (m, 3H), 4.36 (s, 2H), 4.21 (s, 4H).

EXAMPLE 4

N-benzyl-3-((7-chloroisoquinolin-1-yl)amino)benzamide

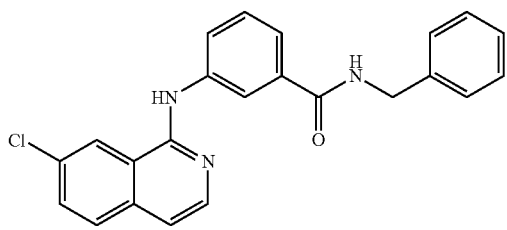 [SMILES: O=C(NCc1ccccc1)c1cccc(Nc2nccc3ccc(Cl)cc23)c1]

Purified by flash column chromatography (ethyl acetate/hexanes), Yield: 20%.

ES-MS [M+H]$^+$: 388.3; $t_R$=0.91 min (Method E).

$^1$H NMR (400 MHz, DMSO-d$_6$) δ: 9.39 (s, 1H), 9.01 (t, J=5.6 Hz, 1H), 8.74 (s, 1H), 8.29 (s, 1H), 8.13 (d, J=8.4 Hz, 1H), 8.04 (d, J=5.6 Hz, 1H), 7.89 (d, J=8.4 Hz, 1H), 7.75 (dd, J=8.8, 1.6 Hz, 1H), 7.53 (d, J=8.0 Hz, 1H), 7.42 (t, J=8.0 Hz, 1H), 7.33 (m, 4H), 7.24 (d, J=5.6 Hz, 2H), 4.49 (s, 2H).

General Procedure IV:

Following procedure B as those described in Schemes 1 or 2 compounds of formulae (Ia) or (Ib) can be prepared in the conditions described below:

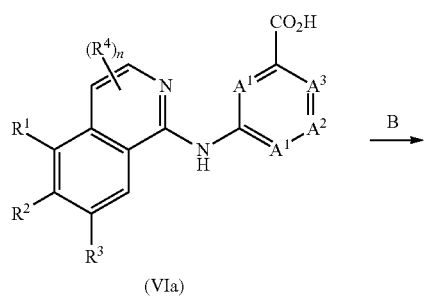

(VIa)

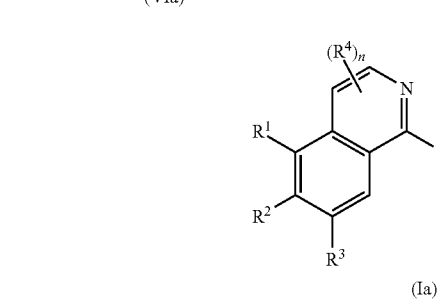

(Ia)

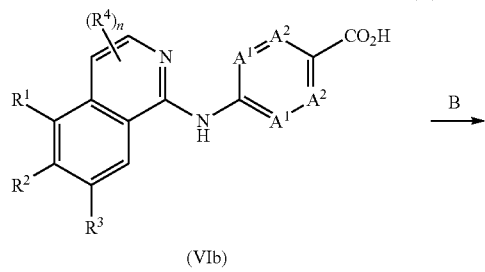

(VIb)

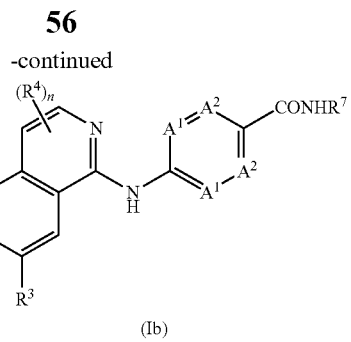

(Ib)

The appropriate amine (ex: 1-(2,3-dihydro-1,4-benzodioxin-6-yl)methanamine) (1 eq) was added to a mixture of 1-ethyl-3-(3-dimethylaminopropyl)carbodiimide chloridric salt (3 eq), diisopropylethylamine (5 eq) and the appropriate acid (VIa) or (VIb) (ex: 4-((7-chloroisoquinolin-1-yl)amino) benzoic acid) (1 eq) in dimethylformamide and the mixture was heated under microwave conditions (600 W) for 10 min. After consumption of starting materials, the reaction mixture was diluted with water and extracted in ethyl acetate (2×). The combined organic extract was washed with brine solution followed by water and the resulting organic layer was dried over anhydrous sodium sulphate and concentrated. The crude was purified by flash column chromatography (dichloromethane/methanol) to afford desired amide compounds (VIIa) or (VIIb) (ex: 4-((7-chloroisoquinolin-1-yl) amino)-N-((2,3-dihydrobenzo[b][1,4]dioxin-6-yl)methyl) benzamide (Example 5).

EXAMPLE 5

4-((7-Chloroisoquinolin-1-yl)amino)-N-((2,3-dihydrobenzo[b][1,4]dioxin-6-yl)methyl)benzamide

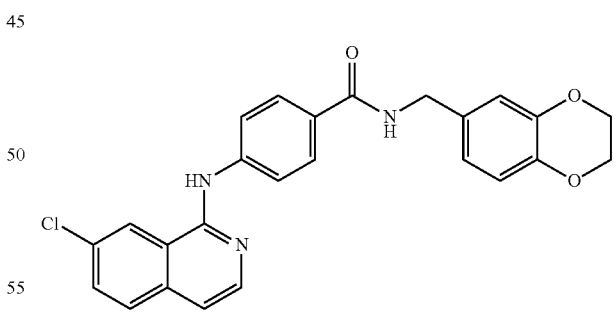

Yield: 10%.

ES-MS [M+H]$^+$: 446.1; $t_R$=3.84 min (Method A).

$^1$H NMR (400 MHz, DMSO-d$_6$) δ: 9.45 (s, 1H), 8.81 (t, J=5.6 Hz, 1H), 8.73 (s, 1H), 8.09 (d, J=5.6 Hz, 1H), 7.98 (d, J=8.4 Hz, 2H), 7.91 (d, J=8.8 Hz, 1H), 7.87 (d, J=8.8 Hz, 2H), 7.77 (dd, J=8.8, 1.6 Hz, 1H), 7.29 (d, J=5.6 Hz, 1H), 6.79 (m, 3H), 4.35 (d, J=5.6 Hz, 2H), 4.21 (s, 4H).

EXAMPLE 6

4-((7-Chloroisoquinolin-1-yl)amino)-N-(2-(pyridin-3-yl)-2-(pyrrolidin-1-yl)ethyl)benzamide

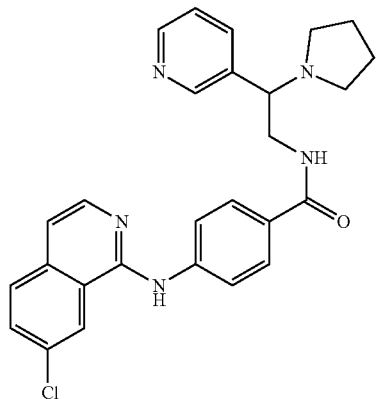 [SMILES: O=C(NCC(c1cccnc1)N1CCCC1)c1ccc(Nc2nccc3ccc(Cl)cc23)cc1]

Yield: 21%.

ES-MS [M+H]$^+$: 472.1; $t_R$=3.56 min (Method B).

$^1$H NMR (400 MHz, CDCl$_3$) δ: 8.62 (br s, 1H), 8.56 (d, J=3.6 Hz, 1H), 8.13 (d, J=6.0 Hz, 1H), 7.96 (br s, 1H), 7.78 (d, J=7.6 Hz, 1H), 7.74-7.68 (m, 6H), 7.61 (dd, J=8.4, 2.0 Hz, 1H), 7.31 (dd, J=7.6, 4.8 Hz, 1H), 7.23 (br s, 1H), 7.18 (d, J=5.6 Hz, 1H), 4.12-4.09 (m, 1H), 3.74-3.64 (m, 2H), 2.65 (br s, 4H), 1.84 (s, 4H).

General Procedure V:

Following procedure B as those described in Schemes 1 or 2 compounds of formulae (Ia) or (Ib) can be prepared in the conditions described below:

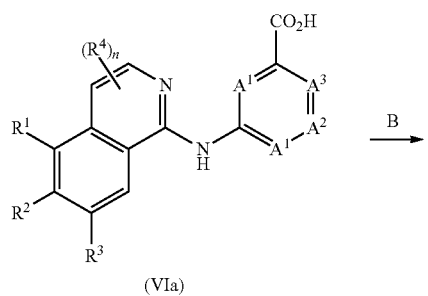

(VIa)

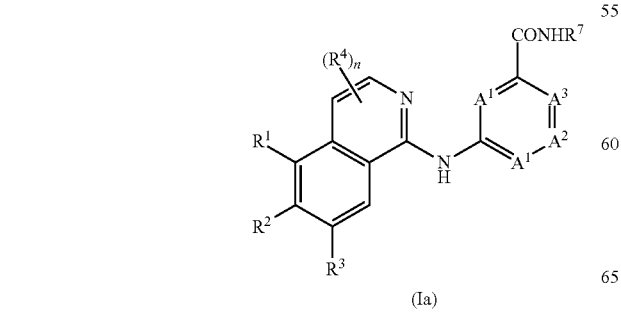

(Ia)

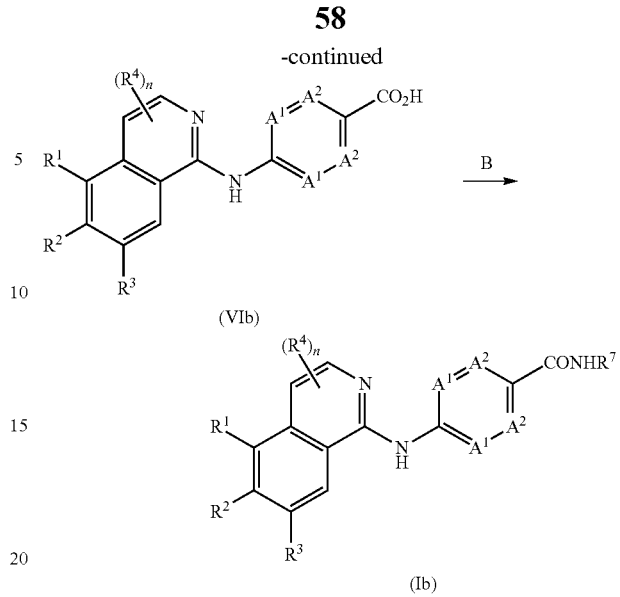

(VIb)

(Ib)

Diisopropylethylamine (4-6 eq) was added to a solution of the appropriate acid (VIa) or (VIb) (ex: 4-((7-chloroisoquinolin-1-yl)amino)picolinic acid) (1 eq), the appropriate amine (ex: 2-(pyridin-3-yl)-2-(pyrrolidin-1-yl)ethan-1-amine) (1 eq) and HATU (2-3 eq) (other coupling agents can be used as TBTU) in dimethylformamide (10 mL/mmol) at room temperature and the mixture was stirred at the same temperature for 2-10 h. After consumption of starting materials, the reaction mixture was quenched into iced-water and the solid precipitated was filtered, washed with cold water (5 mL), and dried under vacuum. The resulting residue was purified by flash column chromatography (dichloromethane/methanol or ethyl acetate/hexanes) to afford desired amide compounds (Ia) or (Ib) (ex: 4-((7-chloroisoquinolin-1-yl)amino)-N-(2-(pyridin-3-yl)-2-(pyrrolidin-1-yl)ethyl)picolinamide (Example 7)).

EXAMPLE 7

4-((7-Chloroisoquinolin-1-yl)amino)-N-(2-(pyridin-3-yl)-2-(pyrrolidin-1-yl)ethyl)picolinamide

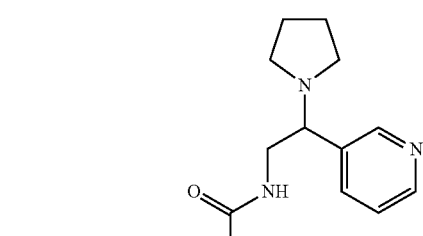

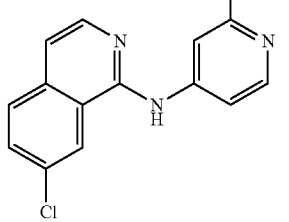

Yield: 12%.

ES-MS [M+H]$^+$: 473.1; $t_R$=3.41 min (Method A).

¹H NMR (400 MHz, CDCl₃) δ: 8.54 (s, 1H), 8.50 (d, J=4.8 Hz, 1H), 8.38 (d, J=6.0 Hz, 1H), 8.22 (m, 3H), 8.07 (s, 1H), 7.81 (brs, 1H), 7.76 (d, J=8.8 Hz, 1H), 7.68 (d, J=7.2 Hz, 1H), 7.63 (dd, J=8.8, 1.6 Hz, 1H), 7.27 (d, J=5.6 Hz, 1H), 7.23 (m, 1H), 4.02 (m, 1H), 3.60 (m, 1H), 3.46 (m, 1H), 2.49 (m, 4H), 1.76 (brs, 4H).

EXAMPLE 8

4-((7-Chloroisoquinolin-1-yl)amino)-N-((2,3-dihydrobenzo[b][1,4]dioxin-6-yl)methyl)picolinamide

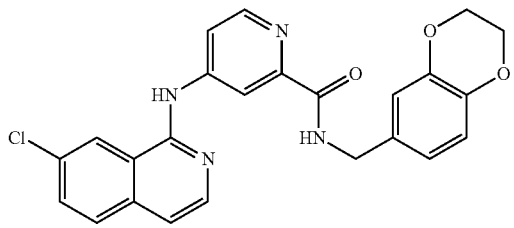 [SMILES: O=C(NCc1ccc2c(c1)OCCO2)c1cc(Nc2nccc3ccc(Cl)cc23)ccn1]

Yield: 44%.

ES-MS [M+H]⁺: 447.0; t_R=4.85 min (Method A).

¹H NMR (400 MHz, DMSO-d₆) δ: 9.69 (s, 1H), 9.09 (m, 2H), 8.73 (s, 1H), 8.58 (dd, J=8.4, 2.4 Hz, 1H), 8.12 (d, J=6.0 Hz, 1H), 8.02 (d, J=8.8 Hz, 1H), 7.96 (d, J=8.8 Hz, 1H), 7.80 (dd, J=9.2, 2.0 Hz, 1H), 7.37 (d, J=6.0 Hz, 1H), 6.84 (s, 1H), 6.79 (s, 2H), 4.36 (s, 2H), 4.21 (s, 4H).

EXAMPLE 9

N-benzyl-4-((7-chloroisoquinolin-1-yl)amino)picolinamide

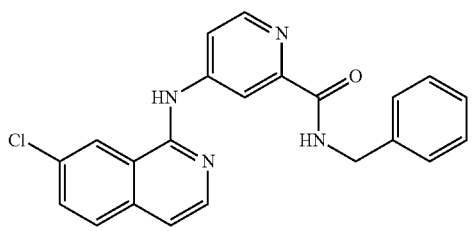 [SMILES: O=C(NCc1ccccc1)c1cc(Nc2nccc3ccc(Cl)cc23)ccn1]

Yield: 31%.

ES-MS [M+H]⁺: 389.1; t_R=4.77 min (Method A).

¹H NMR (400 MHz, DMSO-d₆) δ: 9.86 (s, 1H), 9.28 (brs, 1H), 8.78 (s, 1H), 8.54 (s, 1H), 8.47 (d, J=5.6 Hz, 1H), 8.29 (d, J=4.8 Hz, 1H), 8.20 (d, J=5.2 Hz, 1H), 7.98 (d, J=8.4 Hz, 1H), 7.81 (d, J=8.8 Hz, 1H), 7.44 (d, J=5.6 Hz, 1H), 7.33 (m, 4H), 7.24 (brs, 1H), 4.51 (d, J=5.6 Hz, 2H).

EXAMPLE 10

4-((7-Chloroisoquinolin-1-yl)amino)-N-(4-methoxybenzyl)picolinamide

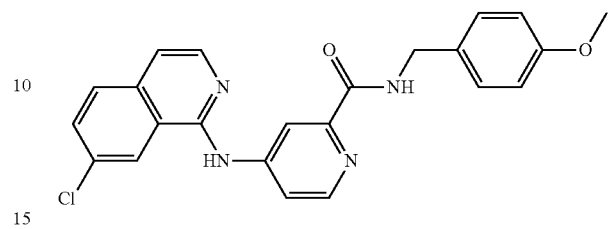

Yield: 58%.

ES-MS [M+H]⁺: 419.0; t_R=3.98 min (Method A).

¹H NMR (400 MHz, DMSO-d₆) δ: 9.86 (s, 1H), 9.19 (t, J=6.0 Hz, 1H), 8.78 (s, 1H), 8.53 (d, J=2.0 Hz, 1H), 8.46 (d, J=5.6 Hz, 1H), 8.27 (dd, J=5.6, 2.4 Hz, 1H), 8.20 (d, J=6.0 Hz, 1H), 7.98 (d, J=8.8 Hz, 1H), 7.82 (dd, J=8.8, 2.0 Hz, 1H), 7.44 (d, J=6.0 Hz, 1H), 7.27 (d, J=8.8 Hz, 2H), 6.88 (d, J=8.8 Hz, 2H), 4.43 (d, J=6.0 Hz, 2H), 3.72 (s, 3H).

EXAMPLE 11

4-((7-Chloroisoquinolin-1-yl)amino)-N-(3-methoxybenzyl)picolinamide

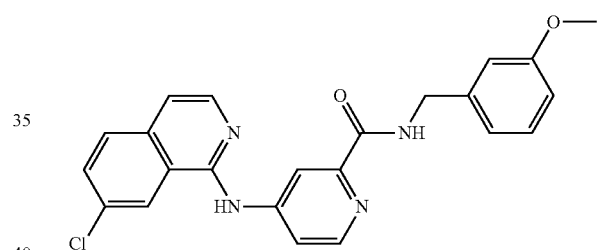

Yield: 36%.

ES-MS [M+H]⁺: 419.1; t_R=4.63 min (Method A).

¹H NMR (400 MHz, DMSO-d₆) δ: 9.85 (s, 1H), 9.26 (t, J=6.4 Hz, 1H), 8.78 (s, 1H), 8.54 (d, J=2.0 Hz, 1H), 8.47 (d, J=5.6 Hz, 1H), 8.29 (dd, J=5.6, 2.4 Hz, 1H), 8.24 (d, J=5.6 Hz, 1H), 7.98 (d, J=8.8 Hz, 1H), 7.82 (dd, J=8.8, 2.0 Hz, 1H), 7.44 (d, J=5.2 Hz, 1H), 7.24 (t, J=8.0 Hz, 1H), 6.91 (d, J=8.0 Hz, 2H), 6.81 (d, J=8.0 Hz, 1H), 4.48 (d, J=6.8 Hz, 2H), 3.73 (s, 3H).

EXAMPLE 12

4-((7-Chloroisoquinolin-1-yl)amino)-N-(3,4-dimethoxybenzyl)picolinamide

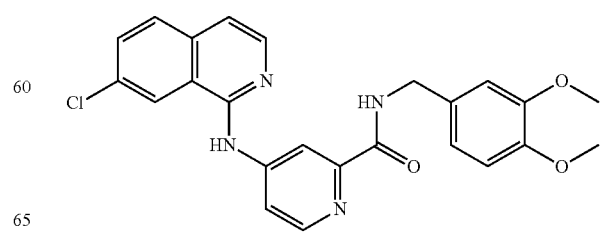

Yield: 14%.

ES-MS [M+H]+: 449.1; $t_R$=4.4 min (Method A).

1H NMR (400 MHz, DMSO-d6) δ: 9.85 (s, 1H), 9.15 (t, J=6.0 Hz, 1H), 8.77 (s, 1H), 8.53 (d, J=2.0 Hz, 1H), 8.46 (d, J=5.2 Hz, 1H), 8.28 (dd, J=5.6, 2.0 Hz, 1H), 8.20 (d, J=5.6 Hz, 1H), 7.98 (d, J=8.8 Hz, 1H), 7.81 (d, J=6.8 Hz, 1H), 7.44 (d, J=5.6 Hz, 1H), 7.00 (s, 1H), 6.90-6.85 (m, 2H), 4.43 (d, J=6.0 Hz, 2H), 3.72 (d, J=6.4 Hz, 6H).

EXAMPLE 13

N-(benzo[c][1,2,5]thiadiazol-5-ylmethyl)-4-((7-chloroisoquinolin-1-yl)amino)picolinamide

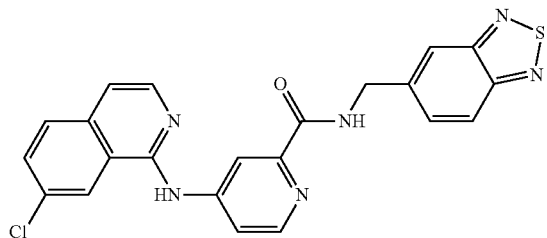 [SMILES: O=C(NCc1ccc2nsnc2c1)c1cc(Nc2nccc3ccc(Cl)cc23)ccn1]

Yield: 17%.

ES-MS [M+H]+: 447.0; $t_R$=3.98 min (Method B).

1H NMR (400 MHz, DMSO-d6) δ: 9.86 (s, 1H), 9.26 (t, J=6.4 Hz, 1H), 8.78 (s, 1H), 8.56 (d, J=2.0 Hz, 1H), 8.50 (d, J=6.0 Hz, 1H), 8.30 (dd, J=5.6, 2.4 Hz, 1H), 8.20 (d, J=6.0 Hz, 1H), 8.07 (d, J=9.2 Hz, 1H), 7.98 (d, J=9.2 Hz, 1H), 7.93 (s, 1H), 7.82 (dd, J=8.8, 1.6 Hz, 1H), 7.44 (d, J=5.6 Hz, 1H), 4.71 (d, J=6.4 Hz, 2H).

EXAMPLE 14

4-((7-Chloroisoquinolin-1-yl)amino)-N-(1,2,3,4-tetrahydronaphthalen-2-yl)picolinamide

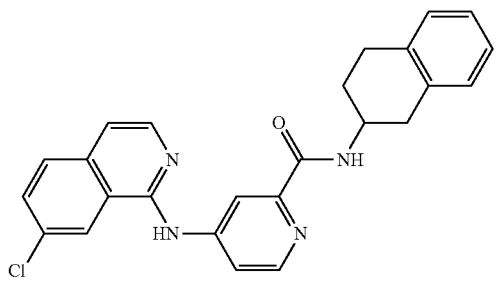 [SMILES: O=C(NC1CCc2ccccc2C1)c1cc(Nc2nccc3ccc(Cl)cc23)ccn1]

Yield: 21%.

ES-MS [M+H]+: 429.0 $t_R$=4.53 min (Method B).

1H NMR (400 MHz, DMSO-d6) δ: 9.88 (s, 1H), 8.79 (s, 1H), 8.65 (d, J=8.2 Hz, 1H), 8.54 (d, J=2.0 Hz, 1H), 8.46 (d, J=5.6 Hz, 1H), 8.30 (dd, J=5.6, 2.0 Hz, 1H), 8.20 (d, J=6.0 Hz, 1H), 7.98 (d, J=8.8 Hz, 1H), 7.82 (dd, J=8.8, 1.6 Hz, 1H), 7.45 (d, J=5.6 Hz, 1H), 7.11 (br s, 3H), 4.25 (m, 1H), 2.96 (m, 4H), 2.01 (m, 1H), 1.92 (m, 1H).

EXAMPLE 15

4-((7-Chloroisoquinolin-1-yl)amino)-N-((3,4-dihydro-2H-benzo[b][1,4]dioxepin-7-yl)methyl)picolinamide

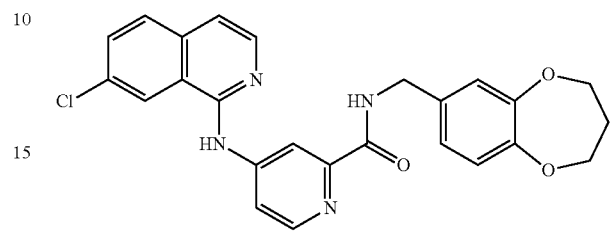

TBTU was used instead of HATU. Purified by flash column chromatography, followed by preparative TLC.

Yield: 17%.

ES-MS [M+H]+: 461.1; $t_R$=4.65 min (Method A);

1H NMR (400 MHz, DMSO-d6) δ: 9.83 (s, 1H), 9.19 (t, J=6.4 Hz, 1H), 8.77 (s, 1H), 8.53 (d, J=1.6 Hz, 1H), 8.46 (d, J=5.6 Hz, 1H), 8.27 (dd, J=5.6, 2.4 Hz, 1H), 8.20 (d, J=5.6 Hz, 1H), 7.97 (d, J=6.0 Hz, 1H), 7.80 (dd, J=8.8, 2.0 Hz, 1H), 7.40 (d, J=5.6 Hz, 1H), 6.94 (s, 1H), 6.90 (d, J=1.2 Hz, 2H), 4.40 (d, J=6.8 Hz, 2H), 4.08 (q, J=5.6 Hz, 4H), 2.10-2.05 (m, 2H).

EXAMPLE 16

4-((7-Chloroisoquinolin-1-yl)amino)-N-((2,3-dihydrobenzofuran-5-yl)methyl)picolinamide

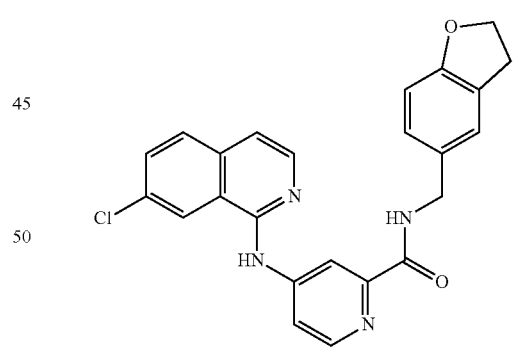

N,N-Diisopropylethylamine was not used and dimethyl sulfoxide was used instead of dimethyl formamide Yield: 3%.

ES-MS [M+H]+: 430.8; $t_R$=4.62 min (Method A).

1H NMR (400 MHz, DMSO-d6) δ: 9.83 (s, 1H), 9.11 (t, J=6.4 Hz, 1H), 8.77 (s, 1H), 8.53 (d, J=2.0 Hz, 1H), 8.45 (d, J=5.6 Hz, 1H), 8.26 (dd, J=5.6, 2.4 Hz, 1H), 8.20 (d, J=5.6 Hz, 1H), 7.97 (d, J=6.0 Hz, 1H), 7.80 (dd, J=8.8, 2.0 Hz, 1H), 7.40 (d, J=5.6 Hz, 1H), 7.22 (s, 1H), 7.07 (d, J=8.8 Hz, 2H), 4.41 (d, J=6.4 Hz, 2H), 3.14 (t, J=8.0 Hz, 2H).

EXAMPLE 17

N-(benzo[d][1,3]dioxol-5-ylmethyl)-4-((7-chloroiso-quinolin-1-yl)amino)picolinamide

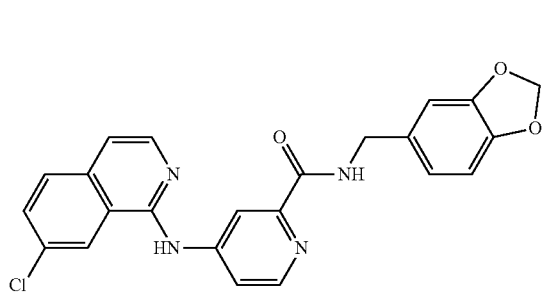 [SMILES: O=C(NCc1ccc2c(c1)OCO2)c1cc(Nc2nccc3ccc(Cl)cc23)ccn1]

Yield: 37%.

ES-MS [M+H]⁺: 433.0; $t_R$=4.59 min (Method A).

¹H NMR (400 MHz, DMSO-d₆) δ: 9.85 (s, 1H), 9.22 (t, J=6.4 Hz, 1H), 8.78 (s, 1H), 8.53 (d, J=2.0 Hz, 1H), 8.46 (d, J=5.6 Hz, 1H), 8.27 (dd, J=5.6, 2.0 Hz, 1H), 8.21 (d, J=5.6 Hz, 1H), 7.98 (d, J=8.8 Hz, 1H), 7.82 (dd, J=8.8, 1.6 Hz, 1H), 7.44 (d, J=6.0 Hz, 1H), 6.93 (d, J=1.2 Hz, 1H), 6.86-6.81 (m, 2H), 5.97 (s, 2H), 4.4 (d, J=6.0 Hz, 2H).

EXAMPLE 18

4-((7-Chloroisoquinolin-1-yl)amino)-N-(2-(2,3-dihydrobenzo[b][1,4]dioxin-6-yl)ethyl)picolinamide

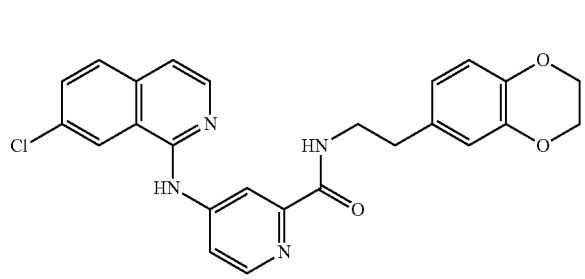 [SMILES: O=C(NCCc1ccc2c(c1)OCCO2)c1cc(Nc2nccc3ccc(Cl)cc23)ccn1]

Yield: 12%.

ES-MS [M+H]⁺: 460.8; $t_R$: 4.65 min (Method A).

¹H NMR (400 MHz, DMSO-d₆) δ: 9.83 (s, 1H), 8.78 (s, 1H), 8.71 (t, J=6.0 Hz, 1H), 8.50 (d, J=2.0 Hz, 1H), 8.44 (d, J=5.6 Hz, 1H), 8.27 (dd, J=5.6, 2.0 Hz, 1H), 8.20 (d, J=5.6 Hz, 1H), 7.98 (d, J=8.8 Hz, 1H), 7.44 (d, J=5.6 Hz, 1H), 6.73 (m, 3H), 4.20 (s, 4H), 3.53 (m, 2H), 2.77 (m, 2H).

EXAMPLE 19

4-((7-Chloroisoquinolin-1-yl)amino)-N-(chroman-6-ylmethyl)picolinamide

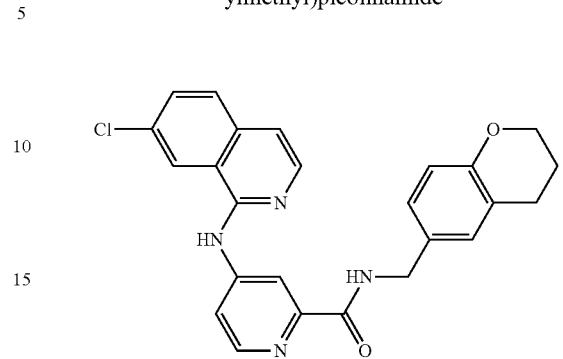

TBTU was used instead of HATU.

Yield: 23%.

ES-MS [M+H]⁺: 445.1; $t_R$=4.8 min (Method A).

¹H NMR (400 MHz, DMSO-d₆) δ: 9.86 (s, 1H), 9.12 (t, J=6.0 Hz, 1H), 8.79 (s, 1H), 8.55 (d, J=1.6 Hz, 1H), 8.47 (d, J=5.6 Hz, 1H), 8.28 (dd, J=5.6, 2.0 Hz, 1H), 8.22 (d, J=5.6 Hz, 1H), 7.99 (d, J=8.8 Hz, 1H), 7.83 (dd, J=8.4, 2.0 Hz, 1H), 7.46 (d, J=5.6 Hz, 1H), 7.05 (m, 2H), 6.68 (d, J=8.4 Hz, 1H), 4.39 (d, J=10.0 Hz, 2H), 4.11 (t, J=4.8 Hz, 2H), 2.72 (m, 2H), 1.90 (m, 2H).

EXAMPLE 20

4-((7-Chloroisoquinolin-1-yl)amino)-N-((1,2,3,4-tetrahydronaphthalen-2-yl)methyl)picolinamide

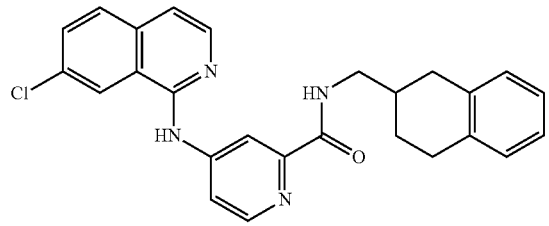 [SMILES: O=C(NCC1CCc2ccccc2C1)c1cc(Nc2nccc3ccc(Cl)cc23)ccn1]

Yield: 17%.

ES-MS [M+H]⁺: 444.9; $t_R$: 5.16 min (Method A).

¹H NMR (400 MHz, DMSO-d₆) δ: 9.84 (s, 1H), 8.84 (m, 1H), 8.78 (s, 1H), 8.53 (d, J=2.4 Hz, 1H), 8.48 (d, J=5.6 Hz, 1H), 8.29 (dd, J=5.6, 2.0 Hz, 1H), 8.20 (d, J=5.6 Hz, 1H), 7.98 (d, J=8.8 Hz, 1H), 7.81 (dd, J=8.8, 2.0 Hz, 1H), 7.44 (d, J=6.0 Hz, 1H), 7.06 (s, 4H), 3.35 (m, 2H, merged with H-O-D peak), 2.78 (m, 3H), 2.50 (m, 1H; merged with residual DMSO peak), 2.06 (m, 1H), 1.93 (m, 1H), 1.39 (m, 1H).

EXAMPLE 21

4-((7-Chloroisoquinolin-1-yl)amino)-N-((2,3-dihydrobenzo[b][1,4]dioxin-2-yl)methyl)picolinamide

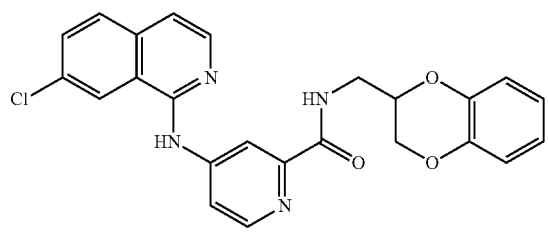 [SMILES: O=C(NCC1COc2ccccc2O1)c1cc(Nc2nccc3ccc(Cl)cc23)ccn1]

Yield: 68%.

ES-MS [M+H]⁺: 446.8; $t_R$: 4.80 min (Method A).

¹H NMR (400 MHz, DMSO-d₆) δ: 9.85 (s, 1H), 8.96 (m, 1H), 8.78 (s, 1H), 8.54 (d, J=2.0 Hz, 1H), 8.48 (d, J=5.6 Hz, 1H), 8.30 (d, J=5.6 Hz, 1H), 8.20 (d, J=6.0 Hz, 1H), 7.98 (d, J=9.2 Hz, 1H), 7.81 (d, J=10.8 Hz, 1H), 7.44 (d, J=5.2 Hz, 1H), 6.87 (m, 4H), 4.37 (m, 2H), 3.98 (dd, J=7.6, 6.8 Hz, 1H), 3.65 (m, 2H).

EXAMPLE 22

4-((7-Chloroisoquinolin-1-yl)amino)-N-(pyridin-3-ylmethyl)picolinamide

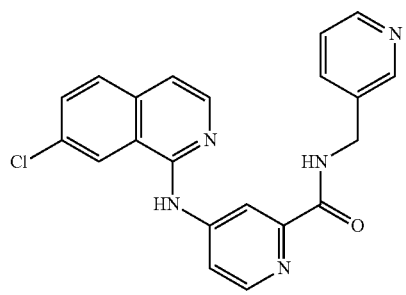 [SMILES: O=C(NCc1cccnc1)c1cc(Nc2nccc3ccc(Cl)cc23)ccn1]

Yield: 15%.

ES-MS [M+H]⁺: 390.0; $t_R$=3.5 min (Method A).

¹H NMR (400 MHz, DMSO-d₆) δ: 9.84 (s, 1H), 9.39 (t, J=6.4 Hz, 1H), 8.77 (s, 1H), 8.56 (d, J=11.6 Hz, 2H), 8.48-8.45 (m, 2H), 8.27 (dd, J=5.6, 2.0 Hz, 1H), 8.20 (d, J=5.6 Hz, 1H), 7.97 (d, J=8.4 Hz, 1H), 7.8 (dd, J=8.8, 2.0 Hz, 1H), 7.74 (d, J=8.0 Hz, 1H), 7.40 (d, J=5.6 Hz, 1H), 7.36-7.33 (m, 1H), 4.53 (d, J=6.4 Hz, 2H).

EXAMPLE 23

4-((7-Chloroisoquinolin-1-yl)amino)-N-(pyridin-4-ylmethyl)picolinamide

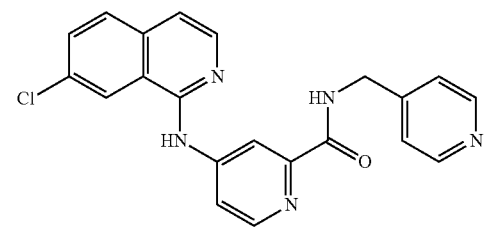 [SMILES: O=C(NCc1ccncc1)c1cc(Nc2nccc3ccc(Cl)cc23)ccn1]

Yield: 16%.

ES-MS [M+H]⁺: 390.1; $t_R$: 3.40 min (Method A).

¹H NMR (400 MHz, DMSO-d₆) δ: 9.85 (s, 1H), 9.42 (dd, J=7.2, 6.0 Hz, 1H), 8.77 (s, 1H), 8.54 (d, J=2.0 Hz, 1H), 8.50 (m, 3H), 8.30 (dd, J=5.2, 2.0 Hz, 1H), 8.20 (d, J=5.6 Hz, 1H), 7.98 (d, J=8.8 Hz, 1H), 7.81 (dd, J=8.8, 2.0 Hz, 1H), 7.44 (d, J=5.2 Hz, 1H), 7.31 (d, J=6.0 Hz, 2H), 4.53 (d, J=6.4 Hz, 2H).

EXAMPLE 24

4-((7-Methoxyisoquinolin-1-yl)amino)-N-(2-(pyridin-3-yl)-2-(pyrrolidin-1-yl)ethyl)picolinamide

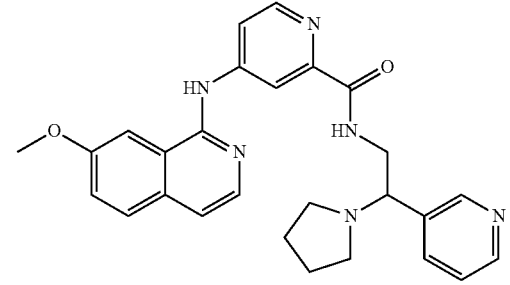 [SMILES: COc1ccc2ccnc(Nc3ccnc(C(=O)NCC(c4cccnc4)N4CCCC4)c3)c2c1]

Yield: 12%.

ES-MS [M+H]⁺: 473.1; $t_R$=3.41 min (Method A).

¹H NMR (400 MHz, CDCl₃) δ: 8.54 (s, 1H), 8.50 (d, J=4.8 Hz, 1H), 8.38 (d, J=6.0 Hz, 1H), 8.22 (m, 3H), 8.07 (s, 1H), 7.81 (brs, 1H), 7.76 (d, J=8.8 Hz, 1H), 7.68 (d, J=7.2 Hz, 1H), 7.63 (dd, J=8.8, 1.6 Hz, 1H), 7.27 (d, J=5.6 Hz, 1H), 7.23 (m, 1H), 4.02 (m, 1H), 3.60 (m, 1H), 3.46 (m, 1H), 2.49 (m, 4H), 1.76 (brs, 4H).

EXAMPLE 25

N-((2,3-dihydrobenzo[b][1,4]dioxin-6-yl)methyl)-4-((7-methoxyisoquinolin-1-yl)amino)picolinamide

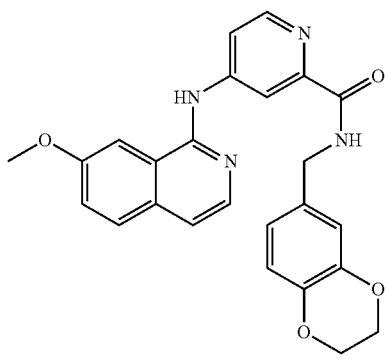 [SMILES: COc1ccc2ccnc(Nc3ccnc(C(=O)NCc4ccc5c(c4)OCCO5)c3)c2c1]

Yield: 19%.

ES-MS [M+H]$^+$: 443.1; $t_R$=3.25 min (Method B).

$^1$H NMR (400 MHz, DMSO-d$_6$) δ: 9.65 (s, 1H), 9.17 (t, J=6.0 Hz, 1H), 8.46-8.43 (m, 2H), 8.27 (d, J=5.6 Hz, 1H), 8.05 (d, J=5.6 Hz, 1H), 7.90 (s, 1H), 7.86 (d, J=8.8 Hz, 1H), 7.43 (dd, J=8.8, 2.0 Hz, 1H), 7.37 (d, J=5.6 Hz, 1H), 6.83 (s, 1H), 6.79 (s, 2H), 4.38 (d, J=6.0 Hz, 2H), 4.20 (s, 4H), 3.98 (s, 3H).

EXAMPLE 26

N-benzyl-4-((7-methoxyisoquinolin-1-yl)amino)picolinamide

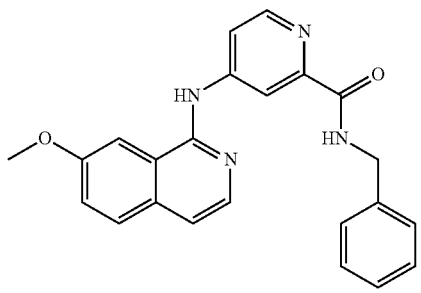 [SMILES: COc1ccc2ccnc(Nc3ccnc(C(=O)NCc4ccccc4)c3)c2c1]

Yield: 68%.

ES-MS [M+H]$^+$: 385.1; $t_R$=3.34 min (Method B).

$^1$H NMR (400 MHz, DMSO-d$_6$) δ: 9.65 (s, 1H), 9.28 (s, 1H), 8.47 (d, J=2.4 Hz, 1H), 8.45 (d, J=6.0 Hz, 1H), 8.29 (dd, J=6.0, 2.0 Hz, 1H), 8.05 (d, J=6 Hz, 1H), 7.91 (s, 1H), 7.86 (d, J=8.8 Hz, 1H), 7.44 (dd, J=8.4, 2.0 Hz, 1H), 7.35 (m, 5H), 7.24 (m, 1H), 4.52 (d, J=6.4 Hz, 2H), 3.98 (s, 3H).

EXAMPLE 27

4-((7-Chloroisoquinolin-1-yl)amino)-N-(2-(pyridin-3-yl)-2-(pyrrolidin-1-yl)ethyl)picolinamide

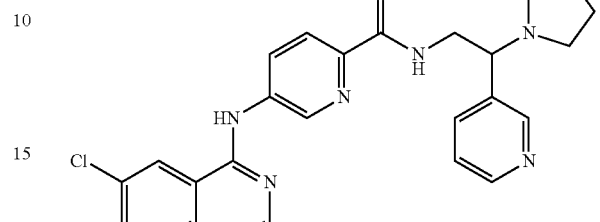

Purified by Preparative HPLC (Method E).

Yield: 28%.

ES-MS [M+H]$^+$: 473.2; $t_R$=3.43 min (Method A).

$^1$H NMR (400 MHz, DMSO-d$_6$) δ: 9.66 (s, 1H), 9.05 (d, J=2.0 Hz, 1H), 8.70 (s, 1H), 8.44 (m, 4H), 8.11 (d, J=6.0 Hz, 1H), 7.94 (dd, J=9.6, 9.2 Hz, 2H), 7.81 (d, J=8.4 Hz, 1H), 7.72 (d, J=8.0 Hz, 1H), 7.37 (d, J=5.6 Hz, 1H), 7.33 (m, 1H), 3.84 (t, J=6.4 Hz, 1H), 3.62 (s, 2H), 2.39 (m, 4H), 1.68 (s, 4H).

EXAMPLE 28

5-((7-Chloroisoquinolin-1-yl)amino)-N-((2,3-dihydrobenzo[b][1,4]dioxin-6-yl)methyl)picolinamide

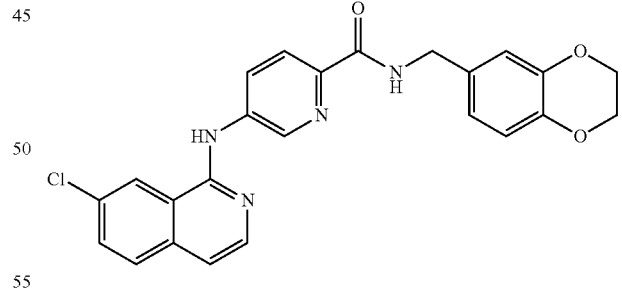

Yield: 44%.

ES-MS [M+H]$^+$: 447.0; $t_R$=4.85 min (Method A).

$^1$H NMR (400 MHz, DMSO-d$_6$) δ: 9.69 (s, 1H), 9.09 (m, 2H), 8.73 (s, 1H), 8.58 (dd, J=8.4, 2.4 Hz, 1H), 8.12 (d, J=6.0 Hz, 1H), 8.02 (d, J=8.8 Hz, 1H), 7.96 (d, J=8.8 Hz, 1H), 7.80 (dd, J=9.2, 2.0 Hz, 1H), 7.37 (d, J=6.0 Hz, 1H), 6.84 (s, 1H), 6.79 (s, 2H), 4.36 (s, 2H), 4.21 (s, 4H).

EXAMPLE 29

N-benzyl-5-((7-chloroisoquinolin-1-yl)amino)picolinamide

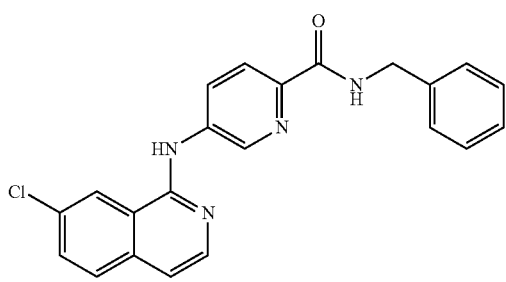 [SMILES: O=C(NCc1ccccc1)c1ccc(Nc2nccc3ccc(Cl)cc23)cn1]

Yield: 27%.

ES-MS [M+H]$^+$: 389.1; $t_R$=4.35 min (Method B).

$^1$H NMR (400 MHz, DMSO-d$_6$) δ: 9.69 (s, 1H), 9.19 (t, J=6.4 Hz, 1H), 9.09 (d, J=2.4 Hz, 1H), 8.73 (s, 1H), 8.58 (dd, J=8.4, 2.4 Hz, 1H), 8.12 (d, J=5.6 Hz, 1H), 8.04 (d, J=8.4 Hz, 1H), 7.96 (d, J=8.8 Hz, 1H), 7.80 (dd, J=8.8, 1.6 Hz, 1H), 7.39-7.30 (m, 5H), 7.24 (t, J=6.4 Hz, 1H), 4.50 (d, J=6.4 Hz, 2H).

EXAMPLE 30

5-((7-Chloroisoquinolin-1-yl)amino)-N-(4-methoxybenzyl)picolinamide

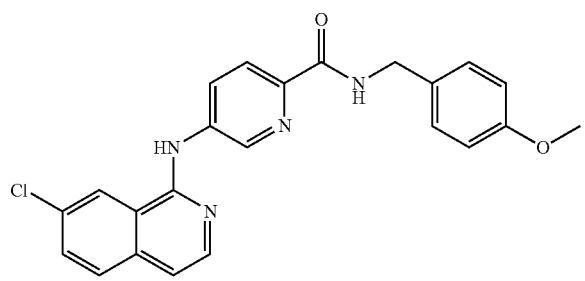 [SMILES: COc1ccc(CNC(=O)c2ccc(Nc3nccc4ccc(Cl)cc34)cn2)cc1]

3.0 eq. of amine was used instead of 1.0 eq. mentioned in general procedure. Yield: 37%.

ES-MS [M+H]$^+$: 419.0; $t_R$=4.11 min (Method B).

$^1$H NMR (400 MHz, DMSO-d$_6$) δ: 9.69 (s, 1H), 9.09-9.07 (m, 2H), 8.72 (s, 1H), 8.58 (dd, J=8.4, 2.4 Hz, 1H), 8.12 (d, J=6.0 Hz, 1H), 8.03 (d, J=8.8 Hz, 1H), 7.96 (d, J=8.8 Hz, 1H), 7.80 (dd, J=8.4, 2.0 Hz, 1H), 7.37 (d, J=5.6 Hz, 1H), 7.28 (d, J=8.8 Hz, 2H), 6.88 (d, J=9.2 Hz, 2H), 4.42 (d, J=6.4 Hz, 2H), 3.72 (s, 3H).

EXAMPLE 31

5-((7-Chloroisoquinolin-1-yl)amino)-N-(3-methoxybenzyl)picolinamide

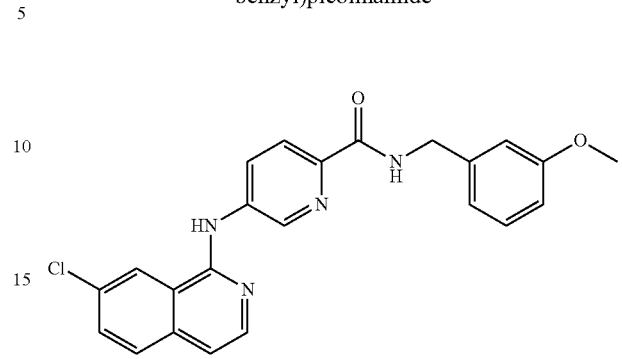

Yield: 28%.

ES-MS [M+H]$^+$: 419.1; $t_R$=4.14 min (Method B).

$^1$H NMR (400 MHz, DMSO-d$_6$) δ: 9.70 (s, 1H), 9.16 (t, J=6.4 Hz, 1H), 9.10 (d, J=2.4 Hz, 1H), 8.73 (s, 1H), 8.58 (dd, J=2.6, 8.4 Hz, 1H), 8.12 (d, J=6.0 Hz, 1H), 8.03 (d, J=8.8 Hz, 1H), 7.96 (d, J=8.8 Hz, 1H), 7.80 (dd, J=8.8, 2.0 Hz, 1H), 7.37 (d, J=5.6 Hz, 1H), 7.23 (dd, J=8.4, 8.0 Hz, 1H), 6.91 (m, 2H), 7.80 (dd, J=8.8, 2.0 Hz, 1H), 4.46 (d, J=6.4 Hz, 2H), 3.73 (s, 3H).

EXAMPLE 32

5-((7-Chloroisoquinolin-1-yl)amino)-N-(3,4-dimethoxybenzyl)picolinamide

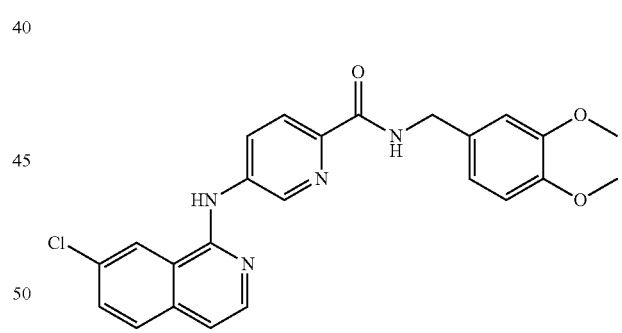

3 eq. of amine was used instead of 1 eq. mentioned in general procedure.

Yield: 10%.

ES-MS [M+H]$^+$: 449.1; $t_R$=4.54 min (Method A).

$^1$H NMR (400 MHz, DMSO-d$_6$) δ: 9.67 (s, 1H), 9.08 (d, J=2.4 Hz, 1H), 9.02 (t, J=6.0 Hz, 1H), 8.72 (s, 1H), 8.56 (dd, J=8.8, 2.4 Hz, 1H), 8.12 (d, J=5.6 Hz, 1H), 8.03 (d, J=8.8 Hz, 1H), 7.95 (d, J=8.8 Hz, 1H), 7.79 (dd, J=8.8, 2.0 Hz, 1H), 7.37 (d, J=5.2 Hz, 1H), 6.99 (s, 1H), 6.91-6.85 (m, 2H), 4.42 (d, J=6.0 Hz, 2H), 3.74 (s, 3H), 3.72 (s, 3H).

EXAMPLE 33

N-(benzo[c][1,2,5]thiadiazol-5-ylmethyl)-5-((7-chloroisoquinolin-1-yl)amino)picolinamide

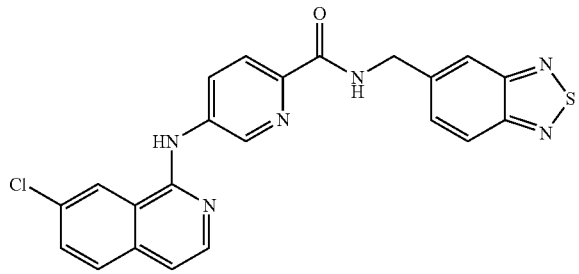 [SMILES: O=C(NCc1ccc2nsnc2c1)c1ccc(Nc2nccc3ccc(Cl)cc23)cn1]

3 eq. of amine was used instead of 1 eq. mentioned in general procedure. Purified by Preparative HPLC (Method D).

Yield: 7%.

ES-MS [M+H]$^+$: 447.0; $t_R$=4.14 min (Method B).

$^1$H NMR (400 MHz, DMSO-d$_6$) δ: 9.70 (s, 1H), 9.41 (t, J=6.4 Hz, 1H), 9.12 (d, J=2.0 Hz, 1H), 8.73 (s, 1H), 8.59 (dd, J=8.8, 2.8 Hz, 1H), 8.13 (d, J=5.6 Hz, 1H), 8.06 (m, 2H), 7.95 (m, 2H), 7.78 (m, 2H), 7.37 (d, J=5.6 Hz, 1H), 4.70 (d, J=7.2 Hz, 2H).

EXAMPLE 34

5-((7-Chloroisoquinolin-1-yl)amino)-N-(1,2,3,4-tetrahydronaphthalen-2-yl)picolinamide

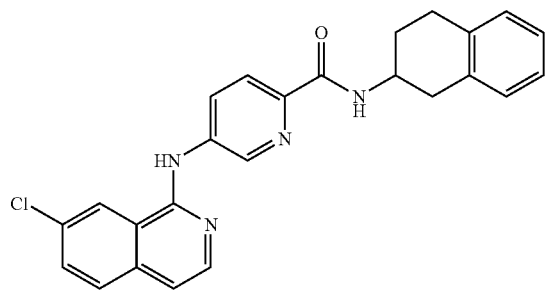 [SMILES: O=C(NC1CCc2ccccc2C1)c1ccc(Nc2nccc3ccc(Cl)cc23)cn1]

Yield: 21%.

ES-MS [M+H]$^+$: 429.0 $t_R$=4.53 min (Method B).

$^1$H NMR (400 MHz, DMSO-d$_6$) δ: 9.88 (s, 1H), 8.79 (s, 1H), 8.65 (d, J=8.2 Hz, 1H), 8.54 (d, J=2.0 Hz, 1H), 8.46 (d, J=5.6 Hz, 1H), 8.30 (dd, J=5.6, 2.0 Hz, 1H), 8.2 (d, J=6.0 Hz, 1H), 7.98 (d, J=8.8 Hz, 1H), 7.82 (dd, J=8.8, 1.6 Hz, 1H), 7.45 (d, J=5.6 Hz, 1H), 7.11 (br s, 3H), 4.25 (m, 1H), 2.96 (m, 4H), 2.01 (m, 1H), 1.92 (m, 1H).

EXAMPLE 35

5-((7-Chloroisoquinolin-1-yl)amino)-N-((3,4-dihydro-2H-benzo[b][1,4]dioxepin-7-yl)methyl)picolinamide

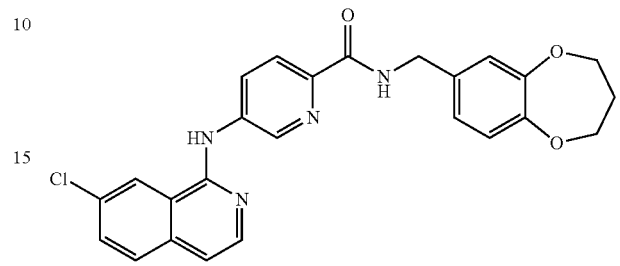

3 eq. of amine was used instead of 1 eq. mentioned in general procedure. Purified by Preparative TLC (5% methanol in dichloromethane).

Yield: 14%.

ES-MS [M+H]$^+$: 461.0; $t_R$=4.80 min (Method A);

$^1$H NMR (400 MHz, DMSO-d$_6$) δ: 9.68 (s, 1H), 9.09 (m, 2H), 8.72 (s, 1H), 8.57 (dd, J=8.8, 2.4 Hz, 1H), 8.12 (d, J=5.6 Hz, 1H), 8.02 (d, J=8.8 Hz, 1H), 7.95 (d, J=8.8 Hz, 1H), 7.80 (dd, J=8.8, 2.0 Hz, 1H), 7.37 (d, J=6.0 Hz, 1H), 6.91 (m, 3H), 4.39 (d, J=6.0 Hz, 2H), 4.08 (m, 4H), 2.08 (m, 2H).

EXAMPLE 36

5-((7-Chloroisoquinolin-1-yl)amino)-N-((2,3-dihydrobenzofuran-5-yl)methyl)picolinamide

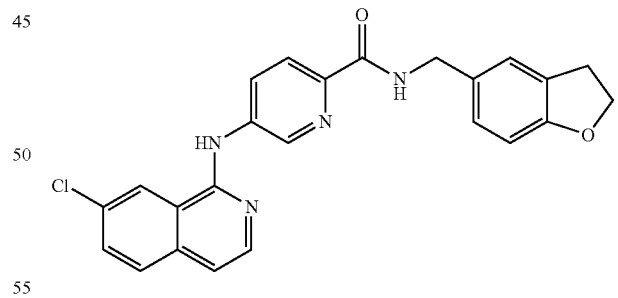

Yield: 5%.

ES-MS [M+H]$^+$: 431.0; $t_R$: 4.75 min (Method A).

$^1$H NMR (400 MHz, DMSO-d$_6$) δ: 9.67 (s, 1H), 9.07 (d, J=2.4 Hz, 1H), 9.01 (dd, J=6.4, 6.0 Hz, 1H), 8.72 (s, 1H), 8.56 (dd, J=8.8, 2.8 Hz, 1H), 8.12 (d, J=5.6 Hz, 1H), 8.02 (d, J=8.8 Hz, 1H), 7.95 (d, J=8.8 Hz, 1H), 7.79 (dd, J=8.8, 2.0 Hz, 1H), 7.36 (d, J=5.6 Hz, 1H), 7.22 (s, 1H), 7.07 (d, J=7.6 Hz, 1H), 6.69 (d, J=8.4 Hz, 1H), 4.49 (t, J=8.8 Hz, 2H), 4.40 (d, J=6.4 Hz, 2H), 3.14 (t, J=8.4 Hz, 2H).

EXAMPLE 37

N-(benzo[d][1,3]dioxol-5-ylmethyl)-5-((7-chloroisoquinolin-1-yl)amino)picolinamide

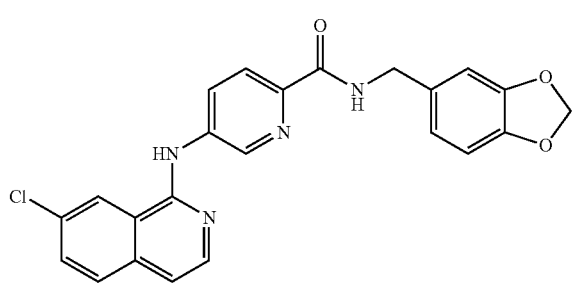 [SMILES: O=C(NCc1ccc2c(c1)OCO2)c1ccc(Nc2nccc3ccc(Cl)cc23)cn1]

Yield: 13%.

ES-MS [M+H]$^+$: 433.0; $t_R$=4.70 min (Method A).

$^1$H NMR (400 MHz, DMSO-d$_6$) δ: 9.69 (s, 1H), 9.12 (t, J=6.0 Hz, 1H), 9.08 (d, J=2.4 Hz, 1H), 8.72 (s, 1H), 8.58 (dd, J=8.4, 2.4 Hz, 1H), 8.12 (d, J=6.0 Hz, 1H), 8.02 (d, J=8.4 Hz, 1H), 7.96 (d, J=8.4 Hz, 1H), 7.80 (dd, J=8.8, 2.0 Hz, 1H), 7.37 (d, J=5.6 Hz, 1H), 6.93 (s, 1H), 6.86-6.80 (m, 2H), 5.97 (s, 2H), 4.39 (d, J=6.4 Hz, 2H).

EXAMPLE 38

5-((7-Chloroisoquinolin-1-yl)amino)-N-(2-(2,3-dihydrobenzo[b][1,4]dioxin-6-yl)ethyl)picolinamide

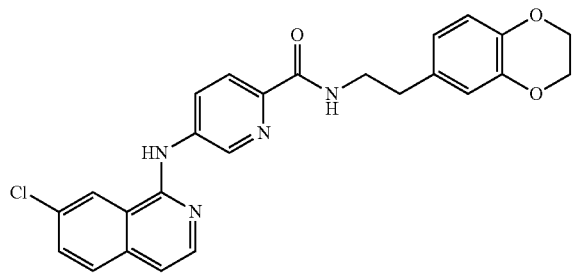 [SMILES: O=C(NCCc1ccc2c(c1)OCCO2)c1ccc(Nc2nccc3ccc(Cl)cc23)cn1]

Yield: 8%.

ES-MS [M+H]$^+$: 461.1; $t_R$: 4.78 min (Method A).

$^1$H NMR (400 MHz, DMSO-d$_6$) δ: 9.66 (s, 1H), 9.07 (d, J=2.4 Hz, 1H), 8.72 (s, 1H), 8.61 (t, J=6.4 Hz, 1H), 8.54 (dd, J=8.8, 2.4 Hz, 1H), 8.12 (d, J=5.6 Hz, 1H), 8.0 (d, J=8.4 Hz, 1H), 7.95 (d, J=8.4 Hz, 1H), 7.80 (dd, J=8.8, 2.0 Hz, 1H), 7.36 (d, J=5.6 Hz, 1H), 6.73 (m, 3H), 4.20 (s, 4H), 3.48 (m, 2H), 2.75 (dd, J=8.0, 7.2 Hz, 2H).

EXAMPLE 39

5-((7-Chloroisoquinolin-1-yl)amino)-N-(chroman-6-ylmethyl)picolinamide

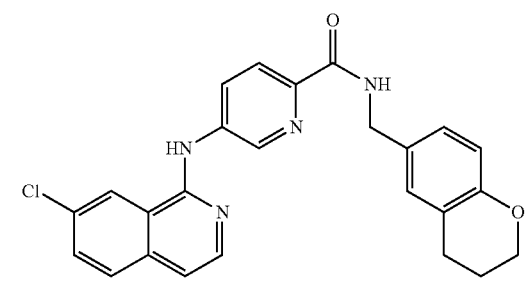 [SMILES: O=C(NCc1ccc2c(c1)CCCO2)c1ccc(Nc2nccc3ccc(Cl)cc23)cn1]

Yield: 13%.

ES-MS [M+H]$^+$: 445.1; $t_R$=4.90 min (Method A).

$^1$H NMR (400 MHz, DMSO-d$_6$) δ: 9.65 (s, 1H), 9.05 (d, J=2.8 Hz, 1H), 8.97 (m, 1H), 8.54 (dd, J=8.4, 2.4 Hz, 1H), 8.10 (d, J=5.6 Hz, 1H), 7.99 (d, J=8.4 Hz, 1H), 7.93 (d, J=8.8 Hz, 1H), 7.77 (dd, J=8.8, 2.0 Hz, 1H), 7.34 (d, J=5.6 Hz, 1H), 7.01 (m, 2H), 6.64 (d, J=8.0 Hz, 1H), 4.35 (d, J=6.0 Hz, 2H), 4.07 (t, J=5.2 Hz, 2H), 2.67 (m, 2H), 1.87 (m, 2H).

EXAMPLE 40

5-((7-Chloroisoquinolin-1-yl)amino)-N-(6-methoxy-1,2,3,4-tetrahydronaphthalen-2-yl)picolinamide

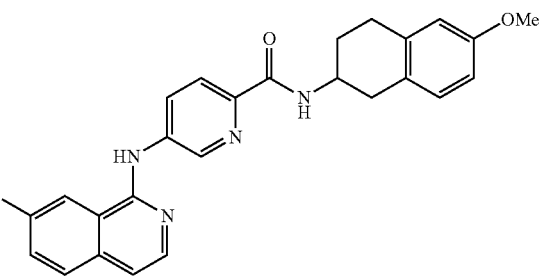

Yield: 17%.

ES-MS [M+H]$^+$: 459.0; $t_R$: 5.06 min (Method A).

$^1$H NMR (400 MHz, DMSO-d$_6$) δ: 9.69 (s, 1H), 9.09 (d, J=2.4 Hz, 1H), 8.72 (s, 1H), 8.56 (dd, J=8.8, 2.4 Hz, 1H), 8.47 (d, J=8.0 Hz, 1H), 8.12 (d, J=5.6 Hz, 1H), 8.04 (d, J=8.8 Hz, 1H), 7.95 (d, J=8.8 Hz, 1H), 7.80 (dd, J=8.8, 2.0 Hz, 1H), 7.37 (d, J=5.6 Hz, 1H), 7.01 (d, J=8.4 Hz, 1H), 6.71 (m, 2H), 4.19 (m, 1H), 3.72 (s, 3H), 2.89 (m, 4H), 1.98 (m, 1H), 1.89 (m, 1H).

EXAMPLE 41

5-((7-Chloroisoquinolin-1-yl)amino)-N-((1,2,3,4-tetrahydronaphthalen-2-yl)methyl)picolinamide

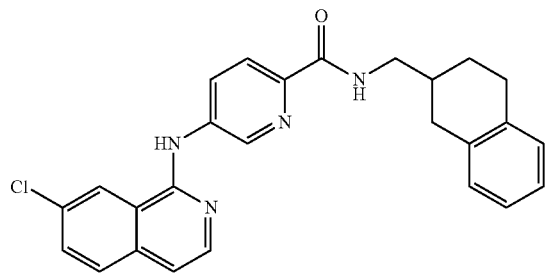 [SMILES: O=C(NCC1CCc2ccccc2C1)c1ccc(Nc2nccc3ccc(Cl)cc23)cn1]

Yield: 10%.

ES-MS [M+H]$^+$: 442.7; $t_R$=5.18 min (Method A).

$^1$H NMR (400 MHz, DMSO-d$_6$) δ: 9.67 (s, 1H), 9.10 (d, J=2.4 Hz, 1H), 8.74 (m, 1H), 8.56 (dd, J=8.4, 2.4 Hz, 1H), 8.12 (d, J=5.6 Hz, 1H), 8.03 (d, J=8.4 Hz, 1H), 7.95 (d, J=8.8 Hz, 1H), 7.80 (dd, J=8.8, 2.0 Hz, 1H), 7.36 (d, J=6.0 Hz, 1H), 7.06 (s, 4H), 3.30 (m, 2H, merged with H-O-D), 2.78 (m, 2H), 2.49 (m, 2H, merged with residual DMSO peak), 2.06 (m, 1H), 1.91 (m, 1H), 1.40 (m, 1H).

EXAMPLE 42

5-((7-Chloroisoquinolin-1-yl)amino)-N-((2,3-dihydrobenzo[b][1,4]dioxin-2-yl)methyl)picolinamide

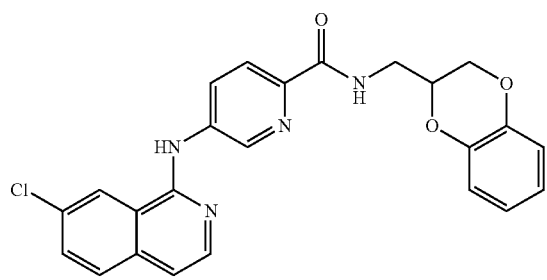 [SMILES: O=C(NCC1COc2ccccc2O1)c1ccc(Nc2nccc3ccc(Cl)cc23)cn1]

Yield: 6%.

ES-MS [M+H]$^+$: 448.7; $t_R$: 4.87 min (Method A).

$^1$H NMR (400 MHz, DMSO-d$_6$) δ: 9.70 (s, 1H), 9.11 (s, 1H), 8.85 (m, 1H), 8.73 (s, 1H), 8.58 (d, J=8.8 Hz, 1H), 8.13 (d, J=5.6 Hz, 1H), 8.03 (d, J=8.4 Hz, 1H), 7.96 (d, J=8.8 Hz, 1H), 7.80 (d, J=8.8 Hz, 1H), 7.38 (d, J=5.6 Hz, 1H), 6.86 (m, 4H), 4.37 (m, 2H), 3.98 (m, 1H), 3.62 (m, 2H).

EXAMPLE 43

5-((7-Chloroisoquinolin-1-yl)amino)-N-(pyridin-3-ylmethyl)picolinamide

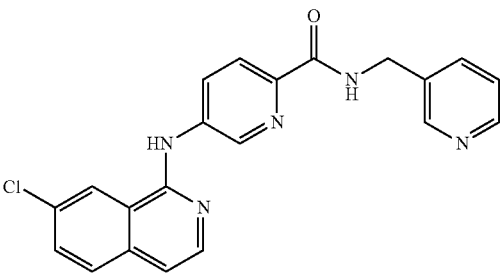 [SMILES: O=C(NCc1cccnc1)c1ccc(Nc2nccc3ccc(Cl)cc23)cn1]

Yield: 11%.

ES-MS [M−H]$^-$: 388.1; $t_R$=4.14 min (Method A).

$^1$H NMR (400 MHz, DMSO-d$_6$) δ: 9.68 (s, 1H), 9.29 (t, J=6.4 Hz, 1H), 9.09 (d, J=2.4 Hz, 1H), 8.72 (s, 1H), 8.58 (m, 2H), 8.45 (dd, J=5.2, 2.0 Hz, 1H), 8.12 (d, J=5.6 Hz, 1H), 8.02 (d, J=8.8 Hz, 1H), 7.95 (d, J=8.8 Hz, 1H), 7.80 (dd, J=8.4, 2.0 Hz, 1H), 7.75 (d, J=7.6 Hz, 1H), 7.35 (m, 2H), 4.51 (d, J=6.4 Hz, 2H).

EXAMPLE 44

5-((7-Chloroisoquinolin-1-yl)amino)-N-(pyridin-4-ylmethyl)picolinamide

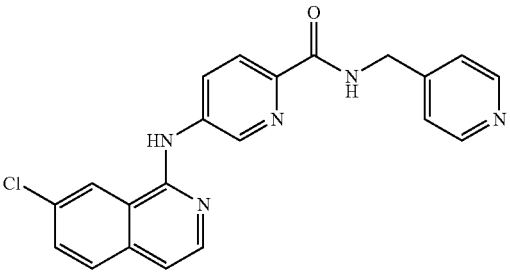 [SMILES: O=C(NCc1ccncc1)c1ccc(Nc2nccc3ccc(Cl)cc23)cn1]

Yield: 9%.

ES-MS [M+H]$^+$: 390.1; $t_R$: 3.55 min (Method A).

$^1$H NMR (400 MHz, DMSO-d$_6$) δ: 9.70 (s, 1H), 9.32 (t, J=5.6 Hz, 1H), 9.12 (d, J=2.8 Hz, 1H), 8.73 (s, 1H), 8.58 (dd, J=8.4, 2.4 Hz, 1H), 8.49 (m, 2H), 8.13 (d, J=5.6 Hz, 1H), 8.03 (d, J=8.8 Hz, 1H), 7.96 (d, J=8.4 Hz, 1H), 7.80 (dd, J=8.8, 2.0 Hz, 1H), 7.38 (d, J=5.6 Hz, 1H), 7.31 (m, 2H), 4.51 (d, J=6.4 Hz, 1H).

EXAMPLE 45

5-((7-Methoxyisoquinolin-1-yl)amino)-N-(1,2,3,4-tetrahydronaphthalen-2-yl)picolinamide

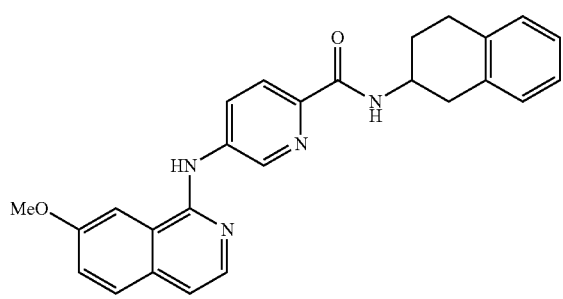 [SMILES: COc1ccc2ccnc(Nc3ccc(C(=O)NC4CCc5ccccc5C4)nc3)c2c1]

Yield: 24%.

ES-MS [M+H]$^+$: 425.2; $t_R$=4.68 min (Method A).

$^1$H NMR (400 MHz, DMSO-d$_6$) δ: 9.47 (s, 1H), 9.08 (d, J=2.4 Hz, 1H), 8.48 (dd, J=8.8, 2.4 Hz, 2H), 8.04 (d, J=8.8 Hz, 1H), 7.96 (d, J=6.4 Hz, 1H), 7.89 (s, 1H), 7.84 (d, J=9.2 Hz, 1H), 7.44 (dd, J=8.8, 2.4 Hz, 1H), 7.29 (d, J=5.6 Hz, 1H), 7.11 (m, 4H), 4.22 (m, 1H), 3.98 (s, 3H), 2.96 (m, 4H), 2.01 (m, 1H), 1.90 (m, 1H).

EXAMPLE 46

N-(6-methoxy-1,2,3,4-tetrahydronaphthalen-2-yl)-5-((7-methoxyisoquinolin-1-yl)amino)picolinamide

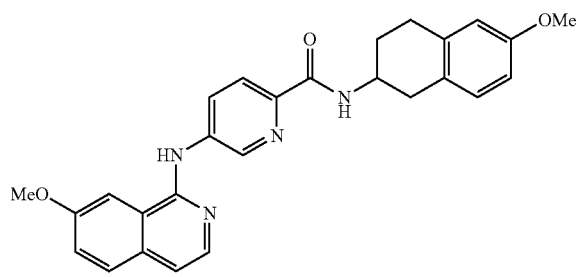 [SMILES: COc1ccc2c(c1)CCC(NC(=O)c1ccc(Nc3nccc4ccc(OC)cc34)cn1)C2]

Yield: 79%.

ES-MS [M+H]$^+$: 455.2; $t_R$=4.59 min (Method A).

$^1$H NMR (400 MHz, DMSO-d$_6$) δ: 9.47 (s, 1H), 9.07 (d, J=2.4 Hz, 1H), 8.47 (m, 2H), 8.03 (d, J=8.8 Hz, 1H), 7.96 (d, J=5.6 Hz, 1H), 7.89 (s, 1H), 7.84 (d, J=9.2 Hz, 1H), 7.44 (dd, J=9.2, 2.4 Hz, 1H), 7.29 (d, J=5.6 Hz, 1H), 7.00 (d, J=8.4 Hz, 1H), 6.70 (m, 2H), 4.19 (m, 1H), 3.98 (s, 3H), 3.72 (s, 3H), 2.88 (m, 4H), 1.99 (m, 1H), 1.90 (m, 1H). Extra signal from impurity was observed at 0.94 ppm.

EXAMPLE 47

5-((7-Methoxyisoquinolin-1-yl)amino)-N-((1,2,3,4-tetrahydronaphthalen-2-yl)methyl)picolinamide

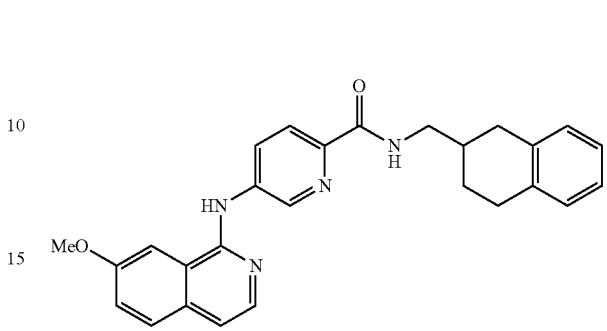

Yield: 78%.

ES-MS [M+H]$^+$: 439.3; $t_R$=4.81 min (Method A).

$^1$H NMR (400 MHz, DMSO-d$_6$) δ: 9.45 (s, 1H), 9.09 (s, 1H), 8.71 (t, J=6.0 Hz, 1H), 8.48 (dd, J=8.4, 2.4 Hz, 1H), 8.02 (d, J=8.8 Hz, 1H), 7.97 (d, J=5.6 Hz, 1H), 7.90 (s, 1H), 7.84 (d, J=8.8 Hz, 1H), 7.44 (dd, J=8.8, 2.4 Hz, 1H), 7.29 (d, J=5.6 Hz, 1H), 7.06 (s, 4H), 3.98 (s, 3H), 3.35 (m, 2H; merged with H-O-D), 2.76 (m, 4H), 2.06 (m, 1H), 1.92 (m, 1H), 1.38 (m, 1H).

EXAMPLE 48

5-((7-Cyanoisoquinolin-1-yl)amino)-N-(1,2,3,4-tetrahydronaphthalen-2-yl)picolinamide

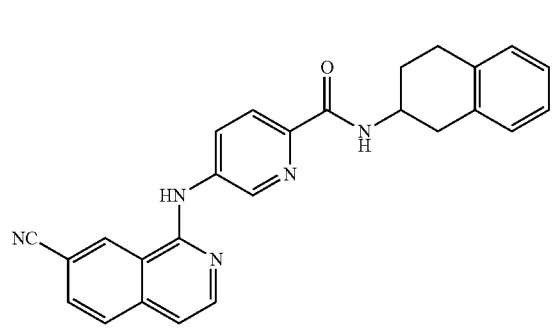 [SMILES: N#Cc1ccc2ccnc(Nc3ccc(C(=O)NC4CCc5ccccc5C4)nc3)c2c1]

Yield: 38%.

ES-MS [M+H]$^+$: 420.2; $t_R$=4.88 min (Method A).

$^1$H NMR (400 MHz, DMSO-d$_6$) δ: 9.85 (s, 1H), 9.18 (s, 1H), 9.09 (d, J=2.4 Hz, 1H), 8.58 (dd, J=8.4, 2.4 Hz, 1H), 8.53 (d, J=8.0 Hz, 1H), 8.25 (d, J=5.6 Hz, 1H), 8.07 (m, 3H), 7.41 (d, J=6.0 Hz, 1H), 7.10 (m, 4H), 4.23 (m, 1H), 2.96 (m, 4H), 2.01 (m, 1H), 1.91 (m, 1H).

EXAMPLE 49

5-((7-Cyanoisoquinolin-1-yl)amino)-N-(pyridin-3-ylmethyl)picolinamide

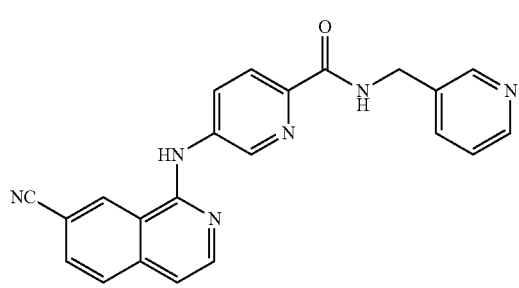 [SMILES: N#Cc1ccc2ccnc(Nc3ccc(C(=O)NCc4cccnc4)nc3)c2c1]

Yield: 28%.

ES-MS [M+H]$^+$: 381.1; $t_R$=3.52 min (Method A).

$^1$H NMR (400 MHz, DMSO-d$_6$) δ: 9.85 (s, 1H), 9.31 (t, J=6.0 Hz, 1H), 9.18 (s, 1H), 9.01 (d, J=2.0 Hz, 1H), 8.59 (m, 2H), 8.45 (dd, J=8.8, 1.6 Hz, 1H), 8.25 (d, J=5.6 Hz, 1H), 8.05 (m, 3H), 7.75 (d, J=8.0 Hz, 1H), 7.41 (d, J=6.0 Hz, 1H), 7.34 (m, 1H), 4.52 (d, J=6.4 Hz, 2H).

EXAMPLE 50

N-(benzo[c][1,2,5]thiadiazol-5-ylmethyl)-5-((7-cyanoisoquinolin-1-yl)amino)picolinamide

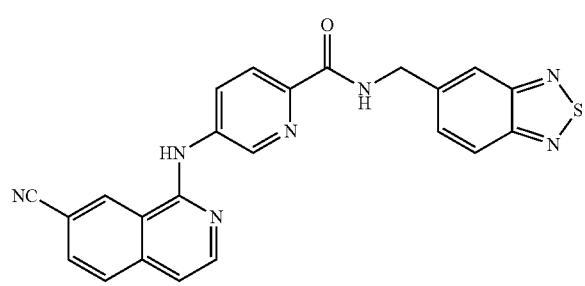 [SMILES: N#Cc1ccc2ccnc(Nc3ccc(C(=O)NCc4ccc5nsnc5c4)nc3)c2c1]

Yield: 40%.

ES-MS [M+H]$^+$: 438.1; $t_R$=4.56 min (Method A);

$^1$H NMR (400 MHz, DMSO-d$_6$) δ: 9.87 (s, 1H), 9.44 (t, J=6.4 Hz, 1H), 9.19 (s, 1H), 9.13 (d, J=2.0 Hz, 1H), 8.61 (dd, J=8.4, 2.4 Hz, 1H), 8.26 (d, J=6.0 Hz, 1H), 8.08-8.06 (m, 4H), 7.93 (s, 1H), 7.76 (dd, J=9.2, 2.4 Hz, 1H), 7.42 (d, J=5.6 Hz, 1H), 4.70 (d, J=6.4 Hz, 2H).

EXAMPLE 51

5-((5-Chloroisoquinolin-1-yl)amino)-N-(1,2,3,4-tetrahydronaphthalen-2-yl)picolinamide

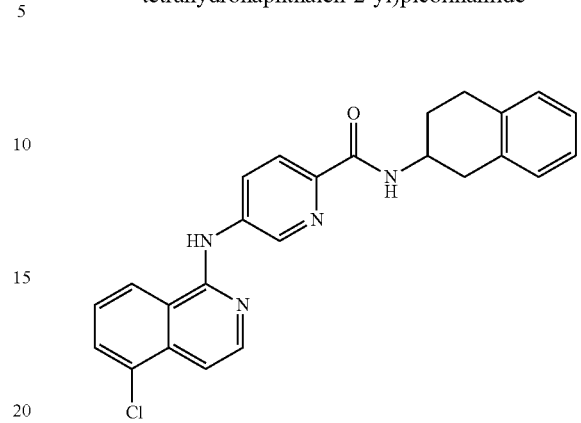

Yield: 40%.

ES-MS [M+H]$^+$: 429.2; $t_R$=5.15 min (Method A).

$^1$H NMR (400 MHz, DMSO-d$_6$) δ: 9.79 (s, 1H), 9.09 (s, 1H), 8.55 (m, 3H), 8.22 (d, J=6.0 Hz, 1H), 8.05 (d, J=8.8 Hz, 1H), 7.97 (d, J=7.6 Hz, 1H), 7.69 (t, J=8.0 Hz, 1H), 7.52 (d, J=6.0 Hz, 1H), 7.10 (m, 4H), 4.23 (m, 1H), 2.96 (m, 4H), 2.01 (m, 1H), 1.91 (m, 1H).

EXAMPLE 52

5-((5-Chloroisoquinolin-1-yl)amino)-N-((2,3-dihydrobenzofuran-5-yl)methyl)picolinamide

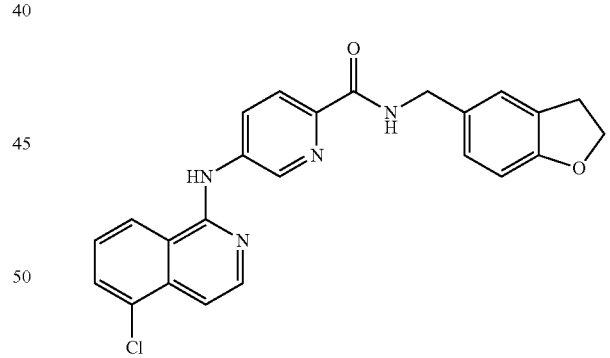

Yield: 16%.

ES-MS [M+H]$^+$: 431.1; $t_R$=4.8 min (Method A).

$^1$H NMR (400 MHz, DMSO-d$_6$) δ: 9.77 (s, 1H), 9.07 (d, J=2.0 Hz, 1H), 9.02 (t, J=6.4 Hz, 1H), 8.59-8.53 (m, 2H), 8.22 (d, J=6.4 Hz, 1H), 8.03 (d, J=8.8 Hz, 1H), 7.97 (d, J=7.6 Hz, 1H), 7.68 (dd, J=8.0, 7.6 Hz, 1H), 7.51 (d, J=5.6 Hz, 1H), 7.22 (s, 1H), 7.07 (d, J=7.6 Hz, 1H), 6.69 (d, J=8.0 Hz, 1H), 4.49 (dd, J=8.8, 8.4 Hz, 2H), 4.40 (d, J=6.0 Hz, 2H), 3.14 (dd, J=8.8, 8.4 Hz, 2H).

EXAMPLE 53

6-((7-Chloroisoquinolin-1-yl)amino)-N-(2-(pyridin-3-yl)-2-(pyrrolidin-1-yl)ethyl)nicotinamide

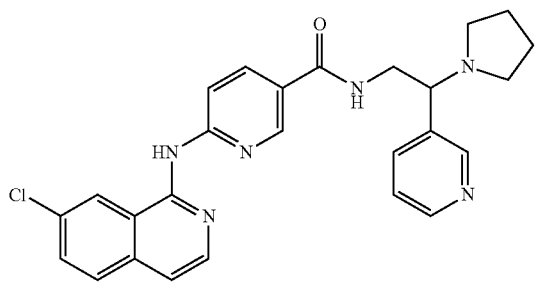 [SMILES: O=C(NCC(c1cccnc1)N1CCCC1)c1ccc(Nc2nccc3ccc(Cl)cc23)nc1]

Purified by Preparative HPLC (Method F).

Yield: 18%.

ES-MS [M+H]$^+$: 473.1; $t_R$=2.73 min (Method A).

$^1$H NMR (400 MHz, DMSO-d$_6$) δ: 10.19 (s, 1H), 8.75 (s, 1H), 8.59 (d, J=2.0 Hz, 1H), 8.47 (d, J=2.0 Hz, 1H), 8.44 (dd, J=5.2, 2.0 Hz, 1H), 8.34 (brs, 1H), 8.23 (d, J=8.8 Hz, 1H), 8.16 (d, J=5.2 Hz, 1H), 7.99 (dd, J=8.8, 2.0 Hz, 1H), 7.95 (d, J=8.8 Hz, 1H), 7.78 (d, J=8.8 Hz, 1H), 7.72 (d, J=7.6 Hz, 1H), 7.44 (d, J=5.6 Hz, 1H), 7.34 (m, 1H), 3.86 (m, 1H), 3.50 (m, 2H), 2.37 (m, 4H), 1.68 (s, 4H).

EXAMPLE 54

6-((7-Chloroisoquinolin-1-yl)amino)-N-((2,3-dihydrobenzo[b][1,4]dioxin-6-yl)methyl)nicotinamide

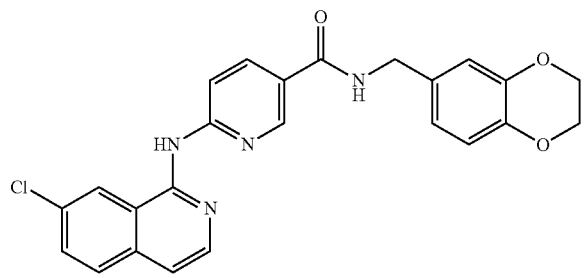

Yield: 28%.

ES-MS [M+H]$^+$: 447.1; $t_R$=2.5 min (Method B).

$^1$H NMR (400 MHz, DMSO-d$_6$) δ: 10.25 (s, 1H), 8.98 (t, J=6.0 Hz, 1H), 8.84 (d, J=1.6 Hz, 1H), 8.78 (s, 1H), 8.32 (d, J=8.8 Hz, 1H), 8.21-8.18 (m, 2H), 7.96 (d, J=8.8 Hz,1H), 7.78 (dd, J=8.0, 2.0 Hz, 1H), 7.45 (d, J=6.0 Hz, 1H), 6.83 (s, 1H), 6.80 (s, 2H), 4.37 (d, J=5.6 Hz, 2H), 4.21 (s, 4H).

EXAMPLE 55

N-benzyl-6-((7-chloroisoquinolin-1-yl)amino)nicotinamide

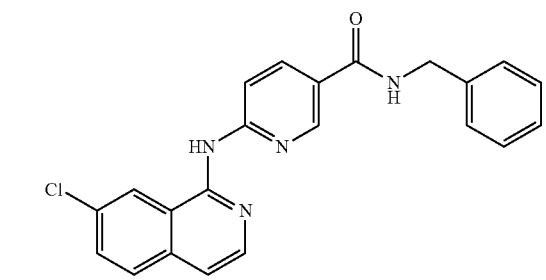 [SMILES: O=C(NCc1ccccc1)c1ccc(Nc2nccc3ccc(Cl)cc23)nc1]

Yield: 27%.

ES-MS [M+H]$^+$: 389.0; $t_R$=2.47 min (Method B).

$^1$H NMR (400 MHz, DMSO-d$_6$) δ: 10.26 (s, 1H), 9.06 (t, J=6.0 Hz, 1H), 8.86 (d, J=1.6 Hz, 1H), 8.78 (s, 1H), 8.33 (d, J=8.8 Hz, 1H), 8.22 (dd, J=8.8, 2.0 Hz, 1H), 8.19 (d, J=6.0 Hz, 1H), 7.96 (d, J=8.8 Hz, 1H), 7.78 (dd, J=8.8, 2.0 Hz, 1H), 7.45 (d, J=5.6 Hz, 1H), 7.35 (m, 4H), 7.26 (m, 1H), 4.51 (d, J=6.0 Hz, 2H).

EXAMPLE 56

6-((7-Chloroisoquinolin-1-yl)amino)-N-(4-methoxybenzyl)nicotinamide

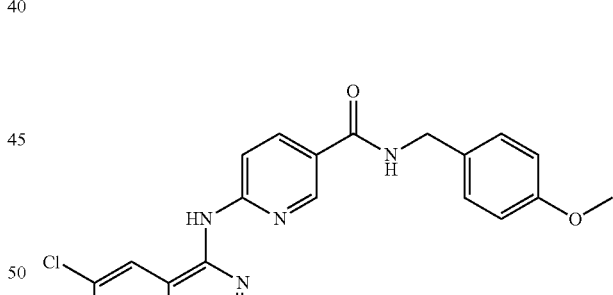

Yield: 18%.

ES-MS [M+H]$^+$: 419.0; $t_R$=2.46 min (Method B).

$^1$H NMR (400 MHz, DMSO-d$_6$) δ: 10.26 (s, 1H), 9.00 (t, J=6.0 Hz, 1H), 8.84 (d, J=2.8 Hz), 8.78 (s, 1H), 8.32 (d, J=8.8 Hz, 1H), 8.22-8.17 (m, 2H), 7.96 (d, J=8.4 Hz, 1H), 7.79 (dd, J=8.4, 2.0 Hz, 1H), 7.45 (d, J=5.6 Hz, 1H), 7.27 (d, J=8.4 Hz, 2H), 6.90 (d, J=8.8 Hz, 2H), 4.43 (d, J=6.0 Hz, 1H), 3.73 (s, 3H).

EXAMPLE 57

6-((7-Chloroisoquinolin-1-yl)amino)-N-(3-methoxybenzyl)nicotinamide

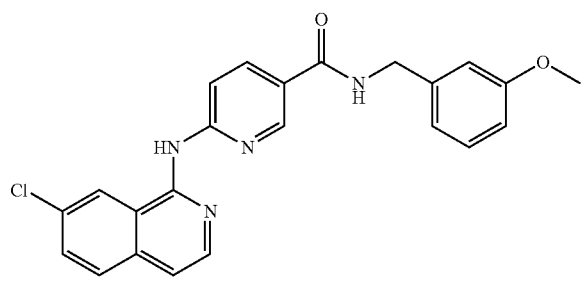 [SMILES: COc1cccc(CNC(=O)c2ccc(Nc3nccc4ccc(Cl)cc34)nc2)c1]

Yield: 14%.

ES-MS [M+H]$^+$: 419.0; $t_R$=3.66 min (Method A).

$^1$H NMR (400 MHz, DMSO-d$_6$) δ: 10.27 (s, 1H), 9.05 (t, J=6.4 Hz, 1H), 8.86 (d, J=2.0 Hz, 1H), 8.78 (s, 1H), 8.33 (d, J=8.8 Hz, 1H), 8.21 (m, 2H), 7.96 (d, J=8.8 Hz, 1H), 7.79 (dd, J=8.8, 2.0 Hz, 1H), 7.45 (d, J=6.0 Hz, 1H), 7.26 (dd, J=8.4, 7.6 Hz, 1H), 6.91 (m, 2H), 6.83 (d, J=8.8 Hz, 1H), 4.48 (d, J=6.0 Hz, 2H), 3.74 (s, 3H).

EXAMPLE 58

6-((7-Chloroisoquinolin-1-yl)amino)-N-(3,4-dimethoxybenzyl)nicotinamide

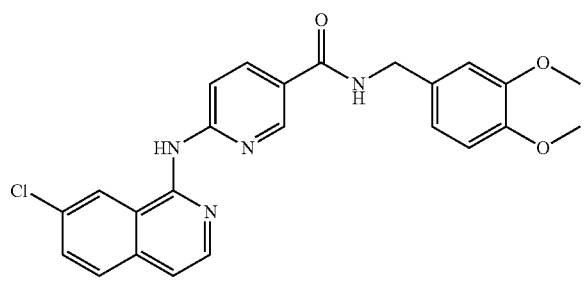 [SMILES: COc1ccc(CNC(=O)c2ccc(Nc3nccc4ccc(Cl)cc34)nc2)cc1OC]

Yield: 12%.

ES-MS [M+H]$^+$: 450.0; $t_R$=3.56 min (Method A).

$^1$H NMR (400 MHz, DMSO-d$_6$) δ: 10.21 (s, 1H), 8.94 (t, J=5.6 Hz, 1H), 8.84 (d, J=2.8 Hz, 1H), 8.77 (s, 1H), 8.31 (d, J=9.2 Hz, 1H), 8.22-8.17 (m, 2H), 7.95 (d, J=8.8 Hz, 1H), 7.78 (dd, J=8.8, 2.0 Hz, 1H), 7.44 (d, J=6.0 Hz, 1H), 6.96-6.85 (m, 3H), 4.43 (d, J=6.0 Hz, 2H), 3.74 (s, 3H), 3.73 (s, 3H).

EXAMPLE 59

N-(benzo[c][1,2,5]thiadiazol-5-ylmethyl)-6-((7-chloroisoquinolin-1-yl)amino)nicotinamide

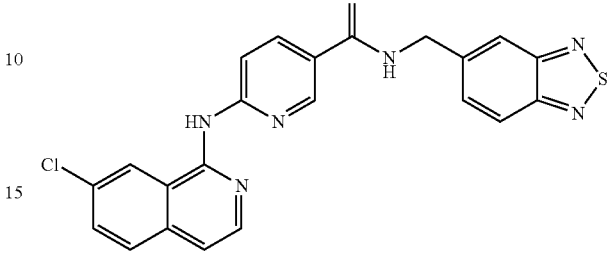

Yield: 11%.

ES-MS [M+H]$^+$: 447.0; $t_R$=3.73 min (Method A).

$^1$H NMR (400 MHz, DMSO-d$_6$) δ: 10.45 (brs, 1H), 9.26 (s, 1H), 8.91 (s, 1H), 8.81 (br s, 1H), 8.28 (m, 1H), 8.19 (br s, 1H), 8.09 (d, J=9.2 Hz, 1H), 7.97 (s, 1H), 7.83 (m, 1H), 7.74 (dd, J=8.8, 1.8 Hz, 1H), 7.48 (m, 1H), 7.09 (m, 2H), 4.71 (d, J=6.0 Hz, 2H).

EXAMPLE 60

6-((7-Chloroisoquinolin-1-yl)amino)-N-(1,2,3,4-tetrahydronaphthalen-2-yl)nicotinamide

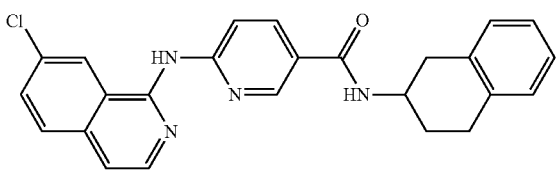 [SMILES: O=C(NC1CCc2ccccc2C1)c1ccc(Nc2nccc3ccc(Cl)cc23)nc1]

Yield: 7%.

ES-MS [M+H]$^+$: 429.0; $t_R$=5.22 min (Method C).

$^1$H NMR (400 MHz, DMSO-d$_6$) δ: 10.25 (s, 1H), 8.83 (d, J=1.6 Hz, 1H), 8.79 (s, 1H), 8.47 (d, J=7.2 Hz, 1H), 8.32 (d, J=8.4 Hz, 1H), 8.20 (m, 2H), 7.96 (d, J=8.8 Hz, 1H), 7.79 (dd, J=8.8, 2.0 Hz, 1H), 7.45 (d, J=5.6 Hz, 1H), 7.11 (m, 3H), 4.17 (m, 1H), 3.04 (m, 2H), 2.89 (m, 2H), 2.08 (m, 1H), 1.79 (m, 1H).

EXAMPLE 61

6-((7-Chloroisoquinolin-1-yl)amino)-N-((3,4-dihydro-2H-benzo[b][1,4]dioxepin-7-yl)methyl)nicotinamide

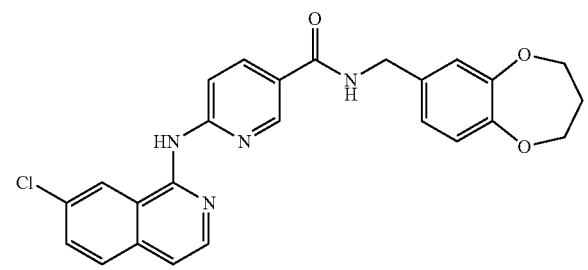 [SMILES: O=C(NCc1ccc2c(c1)OCCCO2)c1ccc(Nc2nccc3ccc(Cl)cc23)nc1]

Yield: 8%.

ES-MS [M+H]$^+$: 462.0; $t_R$=4.36 min (Method A).

$^1$H NMR (400 MHz, DMSO-d$_6$) δ: 10.19 (s, 1H), 8.93 (m, 1H), 8.80 (d, J=1.6 Hz, 1H), 8.74 (s, 1H), 8.27 (d, J=8.8 Hz, 1H), 8.16 (m, 2H), 7.91 (d, J=8.8 Hz, 1H), 7.74 (dd, J=8.8, 2.0 Hz), 7.40 (d, J=6.0 Hz, 1H), 6.88 (m, 2H), 4.35 (d, J=6.0 Hz, 2H), 4.05 (q, J=6.4 Hz, 4H), 2.04 (quint, J=6.0 Hz, 2H).

EXAMPLE 62

N-(benzo[d][1,3]dioxol-5-ylmethyl)-6-((7-chloroisoquinolin-1-yl)amino)nicotinamide

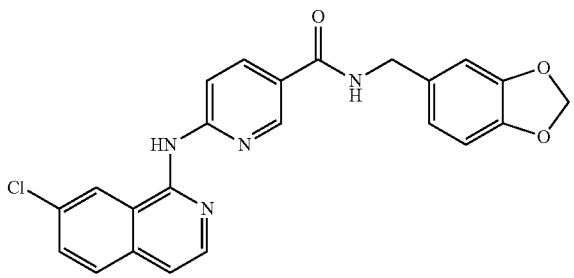 [SMILES: O=C(NCc1ccc2c(c1)OCO2)c1ccc(Nc2nccc3ccc(Cl)cc23)nc1]

TBTU was used instead of HATU.

Yield: 11%.

ES-MS [M+H]$^+$: 433.0; $t_R$=3.84 min (Method A).

$^1$H NMR (400 MHz, DMSO-d$_6$) δ: 10.26 (s, 1H), 9.00 (t, J=6.8 Hz 1H), 8.84 (d, J=2.0 Hz 1H), 8.78 (s, 1H), 8.32 (d, J=8.8 Hz, 1H), 8.21-8.17 (m, 2H), 7.95 (d, J=8.8 Hz, 1H), 7.78 (d, J=8.8 Hz, 1H), 7.44 (d, J=6.0 Hz, 1H), 6.91-6.68 (m, 3H), 5.99 (s, 2H), 4.40 (d, J=5.6 Hz, 2H).

EXAMPLE 63

6-((7-Chloroisoquinolin-1-yl)amino)-N-(chroman-6-ylmethyl)nicotinamide

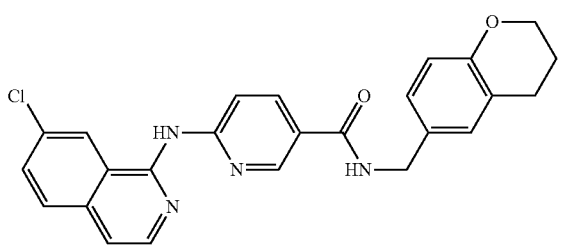 [SMILES: O=C(NCc1ccc2c(c1)CCCO2)c1ccc(Nc2nccc3ccc(Cl)cc23)nc1]

Yield: 22%.

ES-MS [M+H]$^+$: 445.1; $t_R$=3.88 min (Method A).

$^1$H NMR (400 MHz, DMSO-d$_6$) δ: 10.17 (s, 1H), 8.89 (m, 1H), 8.80 (d, J=2.4 Hz, 1H), 8.74 (s, 1H), 8.28 (d, J=8.8 Hz, 1H), 8.15 (m, 2H), 7.92 (d, J=8.4 Hz, 1H), 7.75 (d, J=8.8 Hz, 1H), 7.41 (d, J=6.0 Hz, 1H), 6.99 (m, 2H), 6.65 (d, J=8.4 Hz, 1H), 4.34 (d, J=5.6 Hz, 2H), 4.06 (t, J=5.6 Hz, 2H), 2.68 (t, d=6.8 Hz, 2H), 1.86 (m, 2H).

EXAMPLE 64

5-((7-methoxyisoquinolin-1-yl)amino)-N-(pyridin-3-ylmethyl)picolinamide

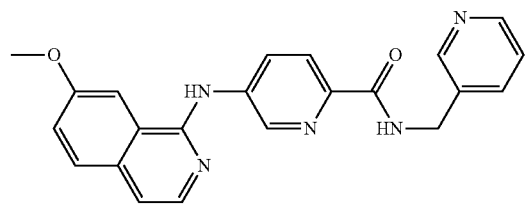 [SMILES: COc1ccc2ccnc(Nc3ccc(C(=O)NCc4cccnc4)nc3)c2c1]

Yield: 30%

ES-MS [M+H]$^+$: 386.2; $t_R$=2.95 min (method A).

$^1$H NMR (400 MHz, DMSO-d$_6$) δ: 9.46 (s, 1H), 9.27 (t, J=6.0 Hz, 1H), 9.07 (d, J=2.4 Hz, 1H), 8.57 (s, 1H), 8.51 (dd, J=8.4, 2.4 Hz, 1H), 8.45 (d, J=3.6 Hz, 1H), 8.02 (d, J=8.8 Hz, 1H), 7.96 (d, J=5.6 Hz, 1H), 7.88 (d, J=2.4 Hz, 1H), 7.84 (d, J=8.8 Hz, 1H), 7.75 (d, J=8.0 Hz, 1H), 7.44 (dd, J=9.2, 2.4 Hz, 1H), 7.35 (m, 1H), 7.29 (d, J=5.6 Hz, 1H), 4.51 (d, J=6.4 Hz, 2H), 3.98 (s, 3H).

General Procedure VI:

Following procedure K as those described in Schemes 3 or 4 compounds of formulae (XIIIc) or (XIIIb) can be prepared in the conditions described below:

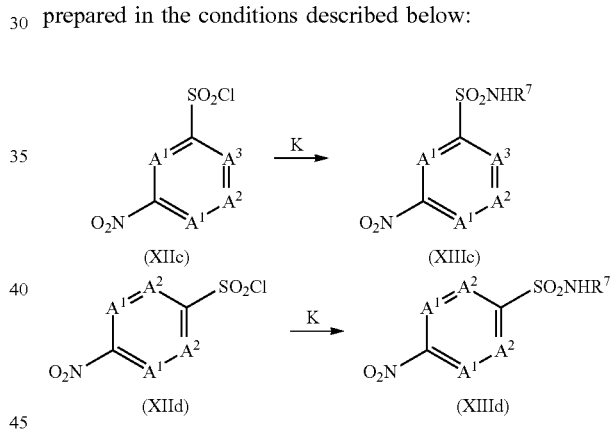

A solution of 3-nitrobenzenesulfonyl chloride (XIIc) or (XIId) (1.5 eq) dissolved in dichloromethane was added dropwise to a cooled solution of the appropriate amine (1.5-1 eq) (ex: phenylmethanamine), pyridine (3 eq) in dichloromethane (0.2 mL/mmol) at 0° C. and reaction mixture was stirred at room temperature for 5-12 h. After consumption of starting materials, as observed by TLC, reaction mass was quenched by addition of water (30 mL) and extracted with dichloromethane (3×). The combined organic extract was washed with water followed by brine solution; dried over anhydrous sodium sulphate and concentrated. The crude compound was purified by flash column chromatogrephy (methanol/dichloromethane) to afford desired sulfonamide (XIIIc) or (XIIId) (ex: N-benzyl-3-nitrobenzene-sulfonamide).

Intermediate 19:

ES-MS [M+1]$^+$: 333.8; $t_R$=4.27 min (Method B) Yield: 40-60%.

Intermediate 20:

ES-MS [M+1]$^+$: 376.8; $t_R$=2.04 min (Method B) Yield: 40-60%.

Intermediate 21:
ES-MS [M+1]$^+$: 392.8; $t_R$=1.71 min (Method B) Yield: 40-60%.
Intermediate 22:
ES-MS [M−1]$^+$: 348.9; $t_R$=4.40 min (Method B) Yield: 40-60%.
Intermediate 23:
Yield: 40-60%.
Intermediate 24:
Yield: 95%.
Intermediate 25:
Yield: 69%.

General Procedure VII:
Following procedure L as those described in Schemes 3 or 4 compounds of formulae (IVc) or (IVb) can be prepared in the conditions described below:

Fe (2 eq) and ammonium chloride (4-6 eq) was added to solution of appropriate sulfonamides (XIIIc) or (XIIId) (ex: N-benzyl-3-nitrobenzenesulfonamide) (1 eq) in ethanol:water (3:1) and reaction mixture was heated to 85° C. for 1-2 h. After consumption of the starting material, as observed by TLC, the reaction mixture was filtered through celite pad and the filtrate was concentrated to afford an aqueous suspension. The suspension was further basified with saturated sodium hydrogen carbonate solution (pH~8) and extracted with dichloromethane (3×). The combined organic extract was washed with water followed by brine solution, dried over anhydrous sodium sulphate, and concentrated. The crude material was as such taken for the next step without further purification (IVc) or (IVd) (ex: 3-amino-N-benzylbenzenesulfonamide).

Intermediate 27:
ES-MS [M+1]$^+$: 346.9; $t_R$=1.03 min (Method B). Yield: 70-80%.
Intermediate 28:
ES-MS [M+1]$^+$: 362.9; $t_R$=1.63 min (Method B). Yield: 70-80%.
Intermediate 29:
ES-MS [M−1]$^+$: 318.9; $t_R$=3.64 min (Method B). Yield: 70-80%.
Intermediate 31 (12i):
Yield: 87%.
Intermediate 32 (1jh):
Yield: 63%.

General Procedure VIII:
Following procedure M as those described in Schemes 3 or 4 compounds of formulae (Ic) or (Id) can be prepared in the conditions described below:

Pd$_2$(dba)$_3$ (0.1 eq) was added to a solution of appropriate amine (IVc) or (IVd) (ex: 3-amino-N-benzylbenzenesulfonamide) (1.1 eq), 1,7-dichloroisoquinoline (II) (1 eq), XantPhos (0.2 eq), and cesium carbonate (2 eq) in pre-degassed 1,4-dioxane (0.17 mL/mmol) and the reaction mixture was heated to 130° C. for 2-3 h. After consumption of starting materials, as observed by TLC, reaction mixture was cooled to room temperature and filtered over celite pad. The filtrate was diluted with water (50 mL) and extracted in ethyl acetate (2×). The combined organic extract was washed with brine solution followed by water, dried over anhydrous

EXAMPLE 65

3-((7-Chloroisoquinolin-1-yl)amino)-N-(2-(pyridin-3-yl)-2-(pyrrolidin-1-yl)ethyl)benzenesulfonamide

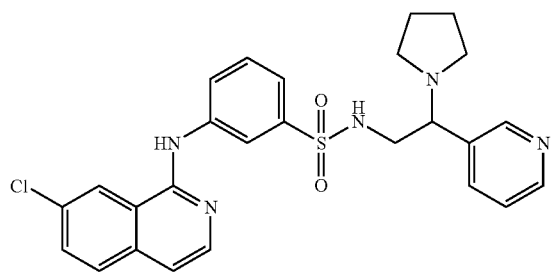 [SMILES: O=S(=O)(NCC(c1cccnc1)N1CCCC1)c1cccc(Nc2nccc3ccc(Cl)cc23)c1]

Yield: 20%.

ES-MS [M+1]$^+$: 508.7; $t_R$=0.61 min (Method E).

$^1$H NMR (400 MHz, DMSO-d$_6$) δ: 9.52 (s, 1H), 8.73 (s, 1H), 8.44 (m, 2H), 8.33 (s, 1H), 8.18 (d, J=9.2 Hz, 1H), 8.05 (d, J=6.0 Hz, 1H), 7.92 (d, J=8.8 Hz, 1H), 7.78 (dd, J=8.0, 1.6 Hz, 1H), 7.63 (d, J=8.0 Hz, 1H), 7.52 (m, 2H), 7.33 (m, 3H), 4.48 (m, 2H), 3.10 (m, 1H), 2.33 (m, 4H), 1.59 (s, 4H).

EXAMPLE 66

3-((7-Chloroisoquinolin-1-yl)amino)-N-(2-morpholino-2-(pyridin-2-yl)ethyl)benzenesulfonamide

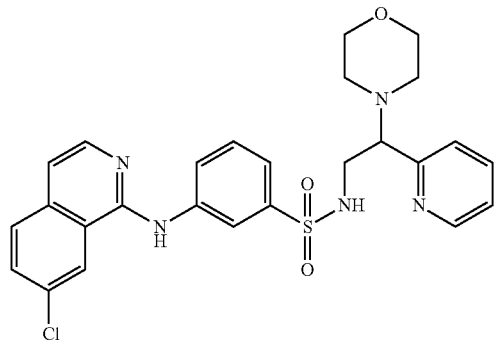 [SMILES: O=S(=O)(NCC(c1ccccn1)N1CCOCC1)c1cccc(Nc2nccc3ccc(Cl)cc23)c1]

Yield: 20%

ES-MS [M+1]$^+$: 524.7; $t_R$=0.69 min (Method E).

$^1$H NMR (400 MHz, DMSO-d$_6$, D$_2$O) δ: 9.53 (s, 1H), 8.73 (s, 1H), 8.52 (d, J=4.8, 1H), 8.36 (s, 1H), 8.20 (d, J=8.0 Hz, 1H), 8.05 (d, J=5.6 Hz, 1H), 7.92 (d, J=8.8 Hz, 1H), 7.76 (m, 2H), 7.51 (m, 2H), 7.41 (d, J=7.6 Hz, 1H), 7.28 (m, 3H), 3.73 (t, J=6.8 Hz, 1H), 3.46 (s, 4H), 3.34 (d, J=6.8 Hz, 2H; merged with H-O-D peak and unmasked after D$_2$O exchange), 2.33 (m, 4H).

EXAMPLE 67

3-((7-Chloroisoquinolin-1-yl)amino)-N-(1-methyl-1H-benzo[d][1,2,3]triazol-4-yl)benzenesulfonamide

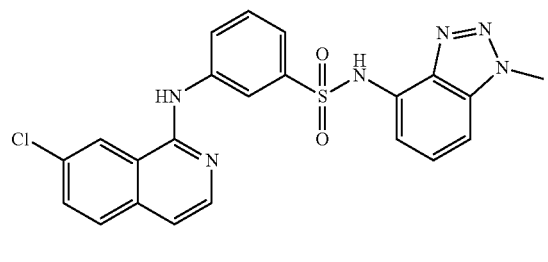 [SMILES: Cn1nnc2c(NS(=O)(=O)c3cccc(Nc4nccc5ccc(Cl)cc45)c3)cccc21]

Yield: 17%.

ES-MS [M+1]$^+$: 465.0; $t_R$=1.05 min (Method E).

$^1$H NMR (400 MHz, DMSO-d$_6$) δ: 11.12 (s, 1H), 9.51 (s, 1H), 8.69 (s, 1H), 8.49 (s, 1H), 8.14 (d, J=8.0 Hz, 1H), 8.01 (d, J=5.6 Hz, 1H), 7.91 (d, J=8.8 Hz, 1H), 7.76 (dd, J=8.8, 2.0 Hz, 1H), 7.53-7.42 (m, 4H), 7.29 (d, J=5.6 Hz, 1H), 7.24 (d, J=7.6 Hz, 1H), 4.23 (s, 3H).

EXAMPLE 68

N-benzyl-3-((7-chloroisoquinolin-1-yl)amino)benzenesulfonamide

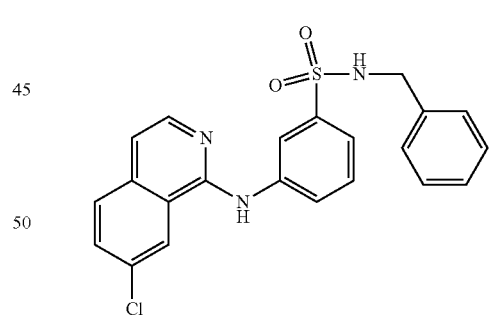

Yield: 61%.

ES-MS [M+1]$^+$: 424.9; $t_R$=1.64 min (Method E).

$^1$H NMR (400 MHz, DMSO-d$_6$) δ: 9.54 (s, 1H), 8.75 (s, 1H), 8.40 (t, J=2.0 Hz, 1H), 8.24 (dd, J=8.4 Hz, 1.2 Hz, 1H), 8.14 (t, J=6.4 Hz, 1H), 8.08 (d, J=6.0 Hz, 1H), 7.93 (d, J=8.8 Hz, 1H), 7.78 (dd, J=8.8 Hz, 1.6 Hz, 1H), 7.54 (dd, J=8.0, 7.6 Hz, 1H), 7.43 (d, J=8.0 Hz, 1H), 7.30 (m, 5H), 7.23 (m, 1H), 4.04 (d, J=6.4 Hz, 2H).

EXAMPLE 69

3-((7-Chloroisoquinolin-1-yl)amino)-N-((2,3-dihydrobenzo[b][1,4]dioxin-6-yl)methyl)benzenesulfonamide

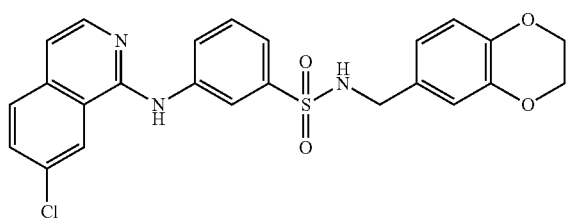 [SMILES: O=S(=O)(NCc1ccc2c(c1)OCCO2)c1cccc(Nc2nccc3ccc(Cl)cc23)c1]

Yield: 24%.

ES-MS [M+1]$^+$: 482.1; $t_R$=14.21 min (Method F).

$^1$H NMR (400 MHz, DMSO-d$_6$) δ: 9.53 (s, 1H), 8.74 (s, 1H), 8.35 (s, 1H), 8.24 (d, J=8.4 Hz, 1H), 8.09-8.03 (m, 2H), 7.92 (d, J=8.8 Hz, 1H), 7.78 (dd, J=8.8, 2.0 Hz, 1H), 7.53 (dd, J=8.4, 7.6 Hz, 1H), 7.39 (d, J=8.0 Hz, 1H), 7.30 (d, J=5.6 Hz, 1H), 6.74-6.69 (m, 3H), 4.17 (s, 4H), 3.91 (d, J=6.0 Hz, 2H).

EXAMPLE 70

3-((7-Chloroisoquinolin-1-yl)amino)-N-(1,2,3,4-tetrahydronaphthalen-2-yl)benzenesulfonamide

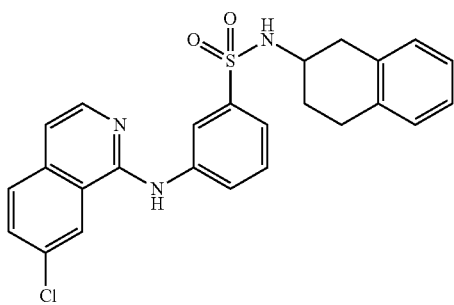 [SMILES: O=S(=O)(NC1CCc2ccccc2C1)c1cccc(Nc2nccc3ccc(Cl)cc23)c1]

Yield: 38%.

ES-MS: [M+H]$^+$: 464, 465; $t_R$=3.42 min, (Method A).

$^1$H NMR (400 MHz, CD$_3$OD) δ: 8.43-8.24 (m, 2H), 7.88-7.76 (m, 2H), 7.68 (t, J=10.6 Hz, 1H), 7.60-7.50 (m, 1H), 7.48-7.34 (m, 2H), 7.06 (t, J=15.4 Hz, 1H), 6.99-6.87 (m, 3H), 6.83 (dd, J=7.6, 1.9 Hz, 1H), 3.53-3.41 (m, 1H), 2.85 (dd, J=16.2, 5.1 Hz, 1H), 2.67 (dddd, J=34.6, 25.8, 14.0, 7.3 Hz, 3H), 1.91-1.81 (m, 1H), 1.61 (dtd, J=12.8, 10.2, 6.0 Hz, 1H).

EXAMPLE 71

3-((7-Chloroisoquinolin-1-yl)amino)-N-((1-methyl-1H-benzo[d][1,2,3]triazol-5-yl)methyl)benzenesulfonamide

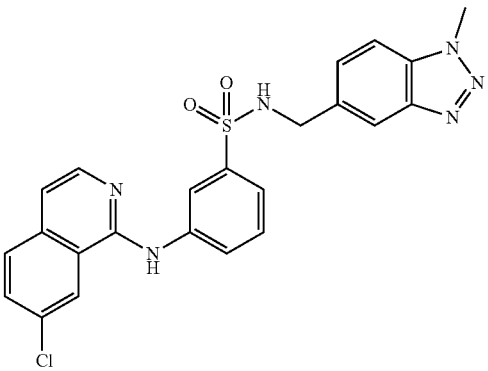 [SMILES: Cn1nnc2cc(CNS(=O)(=O)c3cccc(Nc4nccc5ccc(Cl)cc45)c3)ccc21]

Yield: 14%.

ES-MS: [M+H]$^+$: 479, 480; $t_R$=2.57 min (Method A).

$^1$H NMR (400 MHz, DMSO) δ: 9.47 (s, 1H), 8.71 (s, 1H), 8.36 (t, J=1.9 Hz, 1H), 8.27-8.16 (m, 2H), 8.07 (d, J=5.7 Hz, 1H), 7.91 (d, J=8.8 Hz, 1H), 7.85 (d, J=0.6 Hz, 1H), 7.76 (dd, J=8.7, 2.0 Hz, 1H), 7.71 (d, J=0.7 Hz, 1H), 7.50 (t, J=8.0 Hz, 1H), 7.47-7.39 (m, 2H), 7.29 (d, J=5.9 Hz, 1H), 4.22 (s, 3H) 4.20 (d, J=6.2 Hz, 2H).

EXAMPLE 72

4-((7-Chloroisoquinolin-1-yl)amino)-N-(2-morpholino-2-(pyridin-2-yl)ethyl)benzenesulfonamide

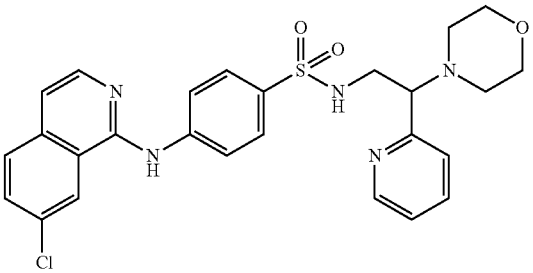 [SMILES: O=S(=O)(NCC(c1ccccn1)N1CCOCC1)c1ccc(Nc2nccc3ccc(Cl)cc23)cc1]

Yield: 21.2%.

ES-MS [M+1]$^+$: 524.1; $t_R$=8.36 min (Method F).

$^1$H NMR (400 MHz, DMSO-d$_6$) δ: 9.60 (s, NH), 8.72 (s, 1H), 8.53 (d, J=4.4 Hz, 1H), 8.12 (d, J=5.6 Hz, 1H), 8.07 (d, J=8.4 Hz, 2H), 7.94 (d, J=8.8 Hz, 1H), 7.79 (d, J=8.4 Hz, 1H), 7.75 (d, J=8.8 Hz, 2H), 7.35 (d, J=6.0 Hz, 1H), 7.29 (m, 3H), 3.72 (t, J=6.8 Hz, 1H), 3.49 (s, 4H), 3.29 (m, 2H), 2.33 (m, 4H).

EXAMPLE 73

4-((7-Chloroisoquinolin-1-yl)amino)-N-(1-methyl-1H-benzo[d][1,2,3]triazol-4-yl)benzenesulfonamide

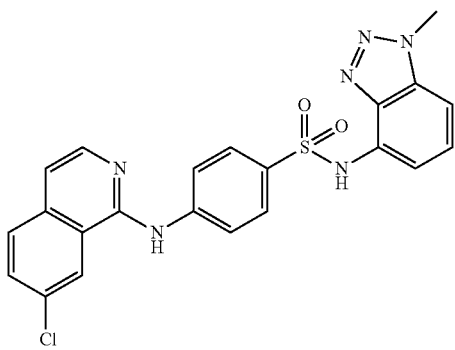 [SMILES: Cn1nnc2c(NS(=O)(=O)c3ccc(Nc4nccc5ccc(Cl)cc45)cc3)cccc21]

Yield: 5%.

ES-MS [M+1]⁺: 465.0; $t_R$=4.14 min (Method G).

¹H NMR (400 MHz, DMSO-d₆) δ: 10.95 (s, NH), 9.56 (s, 1H), 8.66 (s, 1H), 8.07 (d, J=5.6 Hz, 1H), 7.99 (d, J=8.8 Hz, 2H), 7.92 (d, J=8.8 Hz, 1H), 7.85 (d, J=8.8 Hz, 2H), 7.77 (d, J=7.6 Hz, 1H), 7.49-7.40 (m, 2H), 7.34 (d, J=6.0 Hz, 1H), 7.23 (d, J=7.6 Hz, 1H), 4.24 (s, 3H).

EXAMPLE 74

N-(benzo[c][1,2,5]thiadiazol-5-ylmethyl)-3-((7-chloroisoquinolin-1-yl)amino)benzenesulfonamide

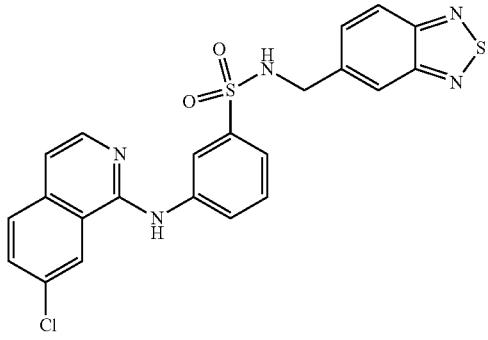 [SMILES: O=S(=O)(NCc1ccc2nsnc2c1)c1cccc(Nc2nccc3ccc(Cl)cc23)c1]

Yield: 12%.

ES-MS [M+1]⁺: 482.0; $t_R$=3.03 min (Method A).

¹H NMR (400 MHz, DMSO-d₆) δ: 9.45 (s, 1H), 8.71-8.69 (m, 1H), 8.41-8.46 (m, 2H), 8.16 (ddd, J=8.1, 2.2, 1.1 Hz, 1H), 8.07 (d, J=5.7 Hz, 1H), 7.96 (dd, J=9.1, 0.6 Hz, 1H), 7.94-7.90 (m, 2H), 7.77 (dd, J=8.7, 2.0 Hz, 1H), 7.62 (dd, J=9.1, 1.7 Hz, 1H), 7.49 (t, J=7.9 Hz, 1H), 7.44-7.41 (m, 1H), 7.31-7.29 (m, 1H), 4.28 (d, J=6.0 Hz, 2H).

EXAMPLE 75

4-((7-chloroisoquinolin-1-yl)amino)-N-((2,3-dihydrobenzo[b][1,4]dioxin-6-yl)methyl)benzenesulfonamide

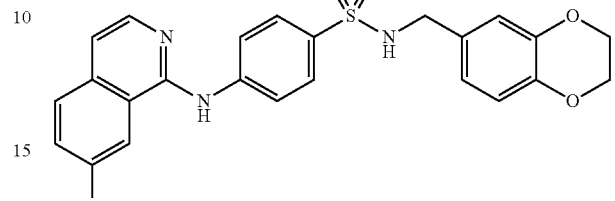

Yield: 17%.

ES-MS [M+1]⁺: 482.0, $t_R$=4.9 min (Method A).

¹H NMR (400 MHz, DMSO-d₆) δ: 9.58 (s, —NH), 8.72 (s, 1H), 8.12 (d, J=5.6 Hz, 1H, 8.07 (d, J=8.8 Hz, 2H), 7.94 (d, J=8.4 Hz, 1H), 7.85 (dd, J=6.4, 6.0 Hz, —NH), 7.79 (dd, J=8.8, 2.0 Hz, 1H), 7.72 (d, J=9.2 Hz, 2H), 7.35 (d, J=5.6 Hz, 1H), 6.76-6.69 (m, 3H), 4.18 (s, 4H), 3.49 (s, 4H), 3.86 (d, J=6.4 Hz, 2H).

EXAMPLE 76

N-(benzo[c][1,2,5]thiadiazol-5-ylmethyl)-4-((7-chloroisoquinolin-1-yl)amino)benzenesulfonamide

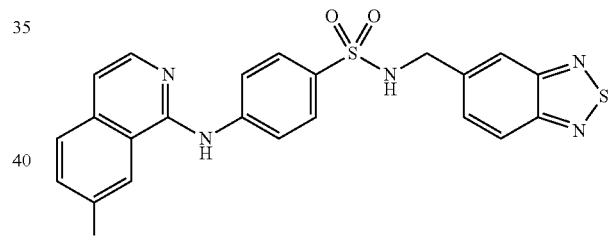

Yield: 11%

ES-MS [M+H]⁺: 482, 483, $t_R$=3.15 min (Method A).

¹H NMR (400 MHz, CD₃OD) δ: 8.47 (s, 1H), 8.06 (d, J=5.9 Hz, 1H), 7.94-7.81 (m, 5H), 7.79-7.73 (m, 2H), 7.71 (dd, J=8.7, 2.0 Hz, 1H), 7.59 (dd, J=9.1, 1.7 Hz, 1H), 7.29 (d, J=5.5 Hz, 1H), 4.28 (s, 2H).

Intermediate 33

4-((7-Chloroisoquinolin-1-yl)amino)benzenesulfonyl chloride

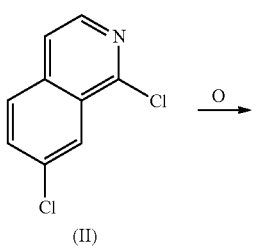

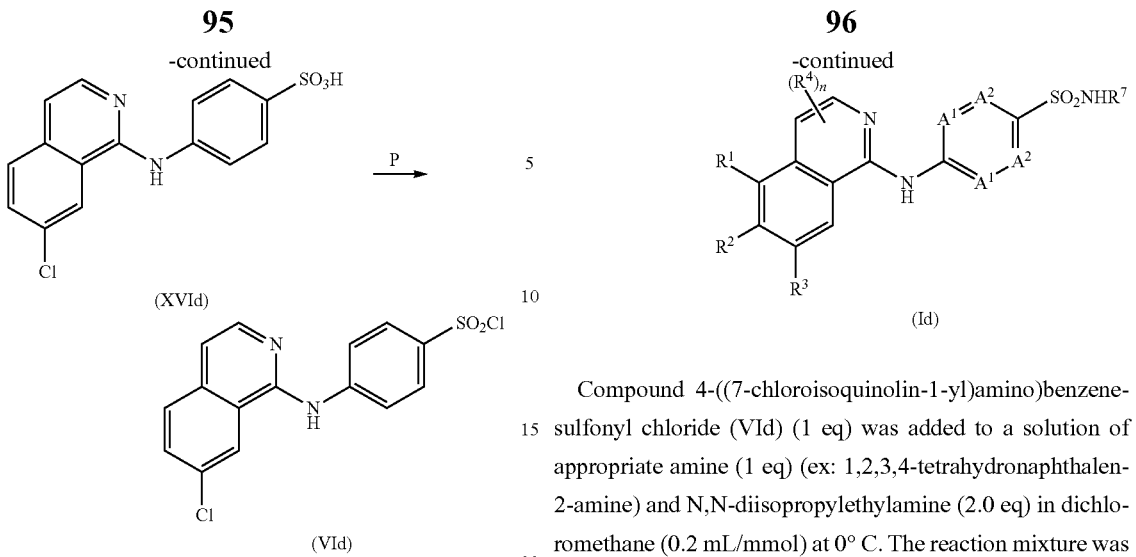

Step 1

1,7-Dichloroisoquinoline (II) (800 mg, 4.04 mmol, 1 eq) was added to a heated solution of sulfanilic acid (700 mg, 1 eq) in 50% aq. ethanol (30 mL) at 80° C. and reaction mixture was heated at same temperature for 12-15 h. After consumption of starting materials, as observed by TLC, reaction mixture was cooled to room temperature and the resultant precipitate was filtered, and washed with 50% aq. ethanol (5 mL) followed by hot methanol (10 mL) to afford compound 4-(7-chloro-isoquinolin-1-ylamino)-benzenesulfonic acid (XVId) (1.14 g) as a pale yellow solid.

Yield: 84%.

ES-MS [M−1]⁻: 333.2; $t_R$=1.47 min (Method G).

$^1$H NMR (400 MHz, DMSO-$d_6$) δ: 8.42 (s, 1H), 7.50 (d, J=5.6, 1H), 7.38 (d, J=8.0, 2H), 7.22 (m, 5H), 6.06 (d, J=5.6 Hz, 1H).

Step 2

Oxalyl chloride (152 mg, 1.2 mmol) was added to a pre-cooled mixture of compound 4-(7-chloro-isoquinolin-1-ylamino)-benzenesulfonic acid (XVId) (200 mg, 0.6 mmol), dichloromethane (10 mL) and dimethylformamide (cat.). The reaction mixture was stirred at r.t. for 12-15 h and concentrated under vacuum. The resultant suspension was further co-distilled with toluene (5×10 mL) to afford crude compound (Vid) which was taken to next step without further purification (204 mg).

Yield: 97%

General Procedure IX:

Following procedure Q as those described in Schemes 5 or 6 compounds of formulae (Ic) or (Id) can be prepared in the conditions described below:

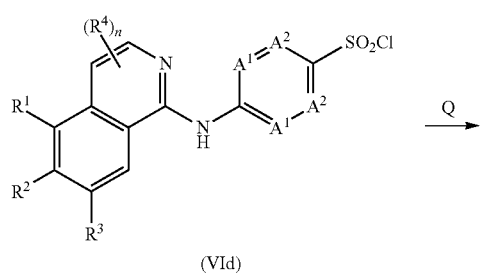

Compound 4-((7-chloroisoquinolin-1-yl)amino)benzenesulfonyl chloride (VId) (1 eq) was added to a solution of appropriate amine (1 eq) (ex: 1,2,3,4-tetrahydronaphthalen-2-amine) and N,N-diisopropylethylamine (2.0 eq) in dichloromethane (0.2 mL/mmol) at 0° C. The reaction mixture was stirred at room temperature for 3-4 h. After consumption of starting materials, as determined by TLC, reaction mixture was quenched by addition of water (10 mL) and extracted with dichloromethane (2×). The combined organic extract was washed with water (2×) followed by brine solution (20 mL), dried over anhydrous sodium sulphate, and concentrated. The crude was purified by flash column chromatography (ethyl acetate/hexanes) to afford the desired sulfonamide derivatives (Id) (ex: 4-((7-chloroisoquinolin-1-yl)amino)-N-(1,2,3,4-tetrahydronaphthalen-2-yl) benzenesulfonamide).

EXAMPLE 77

4-((7-Chloroisoquinolin-1-yl)amino)-N-(1,2,3,4-tetrahydronaphthalen-2-yl)benzenesulfonamide

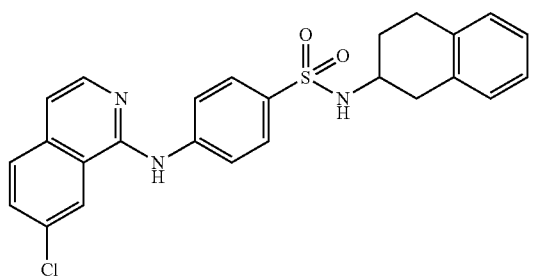 [SMILES: O=S(=O)(NC1CCc2ccccc2C1)c1ccc(Nc2nccc3ccc(Cl)cc23)cc1]

Triethylamine (3 eq) was used instead of N,N-diisopropylethylamine.

Yield: 13%.

ES-MS [M+H]⁺: 464.0; $t_R$=4.96 min (Method B).

$^1$H NMR (400 MHz, DMSO-$d_6$) δ: 9.59 (s, 1H), 8.72 (s, 1H), 8.11 (m, 3H), 7.94 (d, J=8.8 Hz, 1H), 7.79 (m, 3H), 7.63 (d, J=6.4 Hz, 1H), 7.35 (d, J=5.6 Hz, 1H), 7.02 (m, 4H), 3.34 (m, 1H), 2.80 (m, 2H), 2.66 (m, 2H), 1.83 (m, 1H), 1.60 (m, 1H).

EXAMPLE 78

4-((7-Chloroisoquinolin-1-yl)amino)-N-((1,2,3,4-tetrahydronaphthalen-2-yl)methyl)benzenesulfonamide

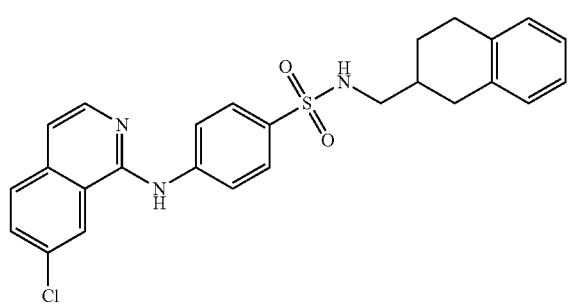 [SMILES: O=S(=O)(NCC1CCc2ccccc2C1)c1ccc(Nc2nccc3ccc(Cl)cc23)cc1]

Yield: 24%.

ES-MS [M+H]+: 477.8; $t_R$=5.08 min (Method B).

$^1$H NMR (400 MHz, DMSO-$d_6$) δ: 9.58 (s, 1H), 8.72 (s, 1H), 8.11 (d, J=5.6 Hz, 1H), 8.08 (d, J=8.8 Hz, 2H), 7.94 (d, J=8.8 Hz, 1H), 7.78 (dd, J=8.8, 2.4 Hz, 1H), 7.75 (d, J=8.8 Hz, 2H), 7.53 (t, J=6.0 Hz, 1H), 7.35 (d, J=6.0 Hz, 1H), 7.03 (m, 4H), 2.71 (m, 4H), 2.35 (m, 2H), 1.84 (m, 2H), 1.30 (m, 1H).

EXAMPLE 79

4-((7-Chloroisoquinolin-1-yl)amino)-N-((2,3-dihydrobenzo[b][1,4]dioxin-2-yl)methyl)benzenesulfonamide

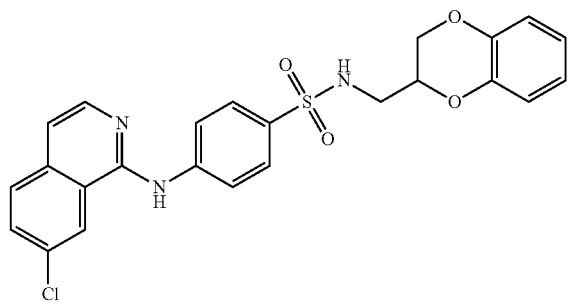 [SMILES: O=S(=O)(NCC1COc2ccccc2O1)c1ccc(Nc2nccc3ccc(Cl)cc23)cc1]

Yield: 33%.

ES-MS [M+H]+: 481.1; $t_R$=4.78 min (Method E).

$^1$H NMR (400 MHz, DMSO-$d_6$) δ: 9.57 (s, 1H), 8.68 (s, 1H), 8.07 (m, 3H), 7.91 (d, J=8.8 Hz, 1H), 7.76 (m, 4H), 7.32 (d, J=5.6 Hz, 1H), 6.80 (m, 4H), 4.24 (dd, J=11.2, 2.4 Hz, 1H), 4.15 (m, 1H), 3.92 (m, 1H), 3.03 (m, 2H).

EXAMPLE 80

N-benzyl-4-((7-chloroisoquinolin-1-yl)amino)benzenesulfonamide

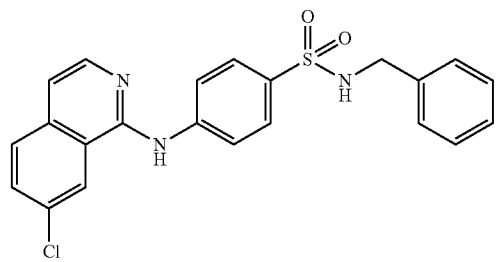 [SMILES: O=S(=O)(NCc1ccccc1)c1ccc(Nc2nccc3ccc(Cl)cc23)cc1]

Benzylamine (20 mg, 0.19 mmol, 1 eq) was added to a solution of crude compound 4-((7-chloroisoquinolin-1-yl)amino)benzenesulfonyl chloride (100 mg, 1 eq) in pyridine (5 mL) and the reaction mixture was stirred at room temperature for 3 h. After consumption of starting materials, as monitored by TLC, reaction mixture was quenched by addition of water (10 mL) and extracted with dichloromethane (2×). The combined organic extract was washed with water (2×) followed by brine solution (20 mL), dried over anhydrous sodium sulphate, and concentrated. The crude compound was purified by flash column chromatography (methanol/dichloromethane) to afford compound N-benzyl-4-((7-chloroisoquinolin-1-yl)amino)benzenesulfonamide as off-white solid (10 mg).

Yield: 13%.

ES-MS [M+1]+: 424.2; $t_R$=1.88 min (Method G).

$^1$H NMR (400 MHz, DMSO-$d_6$) δ: 9.63 (s, 1H), 8.75 (s, 1H), 8.15 (d, J=5.6 Hz, 1H), 8.11 (d, J=8.4 Hz, 1H), 7.99 (t, J=6.4 Hz, —NH), 7.97 (d, J=8.4 Hz, 1H), 7.83-7.81 (m, 3H), 7.38 (d, J=5.6 Hz, 1H), 7.35-7.26 (m, 5H), 4.0 (d, J=6.4 Hz, 2H).

Biological Assays

Compounds according to the present disclosure are capable of binding allosterically or competitively to mutated β-galactosidase enzyme thereby stabilizing the enzyme against denaturation, enhancing its catalytic activity, and promoting the reduction of GM1 ganglioside substrate accumulation.

Enhancement of β-Galactosidase Activity Measured in GM1 Fibroblasts

The capacity of the Compounds of the Disclosure to enhance mutated beta-galactosidase activity levels in GM1 fibroblasts was assayed as follows.

Materials

Fibroblasts homozygous for a GM1 gangliosidosis missense mutation (GM11473) (canine fibroblasts homozygous for the GM1 gangliosidosis missense mutation p.R60H equivalent to human p.R59H mutation) were purchased from Coriell Institute for Medical Research (Camden, N.J., USA).

Cell Culture and Compound Treatment

Fibroblasts were seeded at 4×10$^4$ cells per well in 12-well cell culture plates in Dulbecco's Modified Eagle's Media (DMEM) supplemented with 10% of fetal bovine serum (FBS), 1% penicillin/streptomycin (P/S) (Thermo Fisher Scientific, Waltham, Mass., USA) and incubated at 37° C., 5% CO$_2$ overnight for cell attachment. Subsequently, cells were incubated in the absence or presence of the compounds at the desired concentration for 4 days. After incubation, cells were washed twice with phosphate-buffered saline ("PBS") and detached using Trypsin-EDTA solution (Sigma Aldrich, St. Louis, Mo., USA) to prepare cell pellets. The pellets were stored at −80° C. until activity assays were performed.

Enzyme Activity Assay

β-Galactosidase activity in cell lysates was measured by using 4-Methylumbelliferyl-β-D-galactopyranoside substrate (Sigma Aldrich, St. Louis, Mo., USA). Briefly, lysates were resuspended in 200 μL of 0.9% NaCl containing 0.01% triton X-100 lysis buffer to promote membrane disruption. The cell suspension was sonicated and centrifuged to remove insoluble materials. Then, lysates were mixed with 4-MU-β-D-galactopyranoside in 100 mM citrate buffer (pH=4) and 100 mM NaCl for 60 min at 37° C. The reaction was terminated by adding 100 mM glycine-NaOH buffer (pH=10.7). The liberated 4-MU was measured on a GloMax Discover plate reader (Promega, Madison, Wis., USA) with excitation at 340 nm and emission at 460 nm. Protein quantification was determined using Pierce BCA Protein Assay Kit (Thermo Fisher Scientific, Waltham, Mass., USA). Measurements were interpolated in a 4-MU standard curve and normalized by protein quantity. Enzyme activities were expressed in treated cells as X-fold increase in comparison with non-treated cells (X=1 represents no enhancement).

The capacity of the Compounds of the Disclosure to produce an increase in β-galactosidase enzyme activity in canine GM1 fibroblasts bearing p.R60H canine GLB1 mutation at concentrations between 6 and 50 μM is denoted as follows:

Increase in comparison with non-treated of >2.5 fold is shown as A.

Increase in comparison with non-treated of >1.7-2.5 fold is shown as B.

Increase in comparison with non-treated of 1.2-1.7 fold is shown as C.

D means that no increase compared with non-treated cells was detected in this method.

ND means "not determined."

| Example | Activity in GM11473 fibroblasts |
|---|---|
| 1 | C |
| 2 | C |
| 3 | C |
| 4 | D |
| 5 | B |
| 6 | D |
| 7 | C |
| 8 | B |
| 9 | B |
| 10 | D |
| 11 | B |
| 12 | C |
| 13 | D |
| 14 | B |
| 15 | D |
| 16 | C |
| 17 | B |
| 18 | C |
| 19 | C |
| 20 | B |
| 21 | ND |
| 22 | ND |
| 23 | ND |
| 24 | D |
| 25 | C |
| 26 | C |
| 27 | C |
| 28 | B |
| 29 | A |
| 30 | B |
| 31 | B |
| 32 | C |
| 33 | ND |
| 34 | A |
| 35 | C |
| 36 | C |
| 37 | D |
| 38 | D |
| 39 | B |
| 40 | B |
| 41 | B |
| 42 | A |
| 43 | ND |
| 44 | ND |
| 45 | C |
| 46 | C |
| 47 | B |
| 48 | A |
| 49 | ND |
| 50 | C |
| 51 | ND |
| 52 | ND |
| 53 | C |
| 54 | C |
| 55 | C |
| 56 | D |
| 57 | C |
| 58 | D |
| 59 | C |
| 60 | C |
| 61 | D |
| 62 | D |
| 63 | C |
| 64 | ND |
| 65 | C |
| 66 | C |
| 67 | C |
| 68 | C |
| 69 | D |
| 70 | C |
| 71 | C |
| 72 | D |
| 73 | D |
| 74 | D |
| 75 | B |
| 76 | C |
| 77 | A |
| 78 | A |
| 79 | B |
| 80 | ND |

The capacity of the Compounds of the Disclosure to increase β-galactosidase activity in human fibroblasts cell lines bearing relevant GM1 missense mutations was also studied following the above mentioned protocol. Patient human cell lines were obtained from different institutions (Dr. Katsumi Higaki from the Tottori University, Tottori, Japan and Coriell Institute for Medical Research, Camden, N.J., USA). Compounds showed activity >1.5 fold in a concentration range between 12.5 μM and 50 μM in cell lines bearing the following missense mutations (p.R59H/p.R59H; p.I51T/p.I51T; p.G190D/p.G190D; p.R201C/p.R201C; p.R457Q/p.R457Q; p.C127Y/p.W161G; p.R148S/p.R148S; and p.C127Y/p.W161G).

Reduction of GM1 Ganglioside Accumulation in Culture GM1 Fibroblasts Treated with a Compound of the Disclosure An exemplary Compound of the Disclosure was assayed to determine whether treatment of GM1 gangliosidosis cells GM11473 with the exemplary compound would decrease the level of GM1 ganglioside, one of the β-galactosidase substrates. Accumulation of the β-galactosidase substrates is a cause of the disease.

Experimental Protocol

GM11473 fibroblasts were plated on 12 mm coverslips and cultured in the presence of monosialoganglioside GM1 from bovine brain (Sigma Aldrich, St. Louis, Mo., USA) at a final concentration of 0.1 mg/mL for 2 days. Subsequently, cells were treated with a Compound of the Disclosure for 4 days and GM1 ganglioside accumulation was analyzed by immunofluorescence. Briefly, cells on the coverslips were fixed with 4% paraformaldehyde in PBS for 10 minutes and permeabilized with 0.3% Triton X-100 in PBS for 15 minutes in agitation at room temperature (RT), blocked with 10% of serum in PBS with 0.5% bovine serum albumin ("PBB") for 1 hour and incubated with primary antibody anti-ganglioside GM1 antibody (Abcam, Cambridge, UK) for 16 hours at 4° C. Bound antibodies were detected with Alexa Fluor® 488 Donkey Anti-Rabbit IgG (H+L) at in PBB for 1 hour at RT. HCS CellMask Deep Red Stain and DAPI (Thermo Fisher Scientific, Waltham, Ma., USA) were used to define cell area and nuclei, respectively. Samples were mounted on slides with mounting media Prolong Gold antifade Reagent (Thermo Fisher Scientific, Waltham, Ma., USA) and fluorescence images were obtained using a Leica TCS SPE confocal laser microscopy. Fluorescence intensity was measured using Leica confocal software. For ganglioside quantification, images were taken with Widefield Fluorescence Microscope for Long-term Live Imaging microscope Olympus ScanR and analyzed with Fiji Life-line, 2014 Jun. 2 version.

Results

FIGS. 1A, 1B, 2A, and 2B show that GM1 ganglioside content was reduced in GM11473 fibroblasts after treatment with a Compound of the Disclosure (as it is shown in FIGS. 2A and 2B) compared with cells cultured in the absence of a Compound of the Disclosure (as it is shown in FIGS. 1A and 1B). FIGS. 1A and 1B show accumulation of GM1 ganglioside in GM11473 untreated cells in two separate fluorescence images for the same sample set (white color shows accumulation of GM1 ganglioside). FIGS. 2A and 2B show a reduction of GM1 ganglioside accumulation in GM11473 cells treated with a Compound of the Disclosure at 50 μM in two separate fluorescence images for the same sample set (white color shows accumulation of GM1 ganglioside).

All publications cited in this specification are incorporated herein by reference. While the disclosure has been described with reference to particular embodiments, it will be appreciated that modifications can be made without departing from the spirit of the disclosure. Such modifications are intended to fall within the scope of the appended claims.

The invention claimed is:

1. A compound of formula (I):

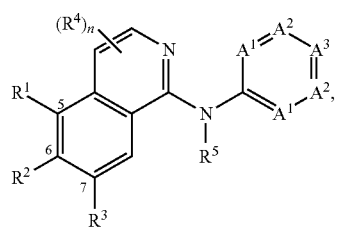

(I)

or a salt or solvate thereof, wherein:

each of $A^1$ is independently selected from the group consisting of nitrogen and CH; and each of $A^2$ and $A^3$ is independently selected from the group consisting of nitrogen, CH, and $C(R^6)$; wherein each $A^1$ is CH and each of $A^2$ and $A^3$ is independently selected from CH and $C(R^6)$, provided that only one of $A^2$ and $A^3$ is $C(R^6)$; or exactly one of $A^2$ and $A^3$ is $C(R^6)$ and no less than one and no more than two of $A^1$, $A^2$, and $A^3$ are nitrogen;

$R^1$, $R^2$, and $R^3$ are each independently selected from the group consisting of hydrogen, halogen, —CN, —ORb, and —$C_{1-4}$ alkyl, wherein said —$C_{1-4}$ alkyl group is optionally substituted by 1, 2 or 3 independently selected halogen atoms, with the proviso that at least one $R^1$, $R^2$, and $R^3$ is other than hydrogen;

$R^6$ is —B—NH—$R^7$;

B is —CO— or —$SO_2$—;

each $R^4$ is independent selected from the group consisting of halogen, —$C_{1-4}$ alkyl, —$C_{1-4}$ alkoxy, —CN and hydroxy;

n has a value selected from 0, 1 or 2;

$R^5$ is hydrogen or —$C_{1-4}$ alkyl;

$R^7$ is selected from the group consisting of —$C_{1-4}$ alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, (5- to 10-membered)-$C_{1-9}$ heteroaryl, —$C_{1-4}$ alkyl-(5- to 10-membered)-$C_{1-9}$ heteroaryl, (5- to 10-membered)-$C_{1-9}$ heterocyclyl, and —$C_{1-4}$ alkyl-(5- to 10-membered)-$C_{1-9}$ heterocyclyl; said alkyl, cycloalkyl, alkylcycloalkyl, aryl, alkylaryl, heteroaryl, alkylheteroaryl, heterocyclyl, and alkylheterocyclyl groups optionally being substituted with 1, 2, or 3 groups independently selected from the group consisting of halogen, hydroxyl, —CN, —ORb, —SRb, —$N(Rb)_2$, —$C_{1-4}$alkyl optionally substituted with 1, 2, or 3 halogen atoms, optionally substituted $C_{6-10}$ aryl, optionally substituted (5- to 10-membered)-$C_{1-9}$ heteroaryl, and (5- to 10-membered)-$C_{1-9}$ heterocyclyl; said cycloalkyl, alkylcycloalkyl, aryl, alkylaryl, heteroaryl, alkylheteroaryl, heterocyclyl, and alkylheterocyclyl is optionally fused to a further (second) ring, and each Rb is independently hydrogen, —$C_{1-4}$ alkyl, —$C_{3-10}$ cycloalkyl, or (5- to 10-membered)-$C_{1-9}$ heterocyclyl; said alkyl, cycloalkyl or heterocyclyl groups optionally being substituted by 1, 2 or 3 fluorine atoms.

2. The compound of claim 1, having the formula (IA):

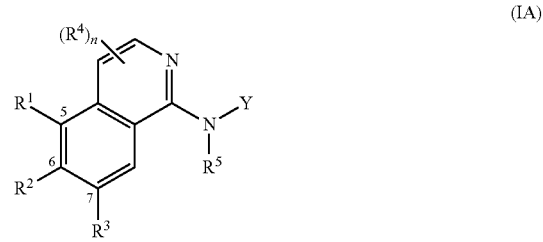

(IA)

or a salt or solvate thereof, wherein:

$R^1$, $R^2$, $R^3$, $R^4$, and $R^5$, are as defined in claim 1, with the proviso that at least one $R^1$, $R^2$, and $R^3$ is other than hydrogen;

n is 0 or 1, and

Y is selected from the group consisting of
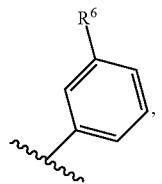 Y1
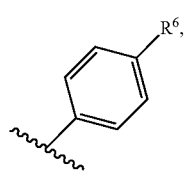 Y2
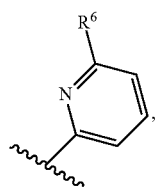 Y3
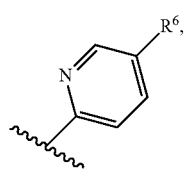 Y4
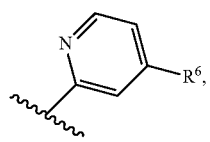 Y5
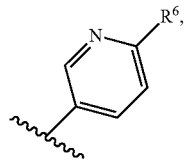 Y6
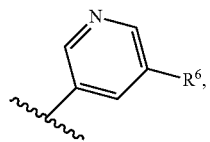 Y7
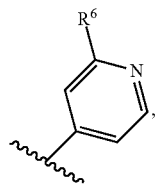 Y8
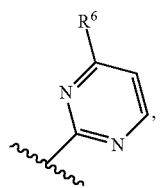 Y9
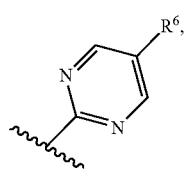 Y10
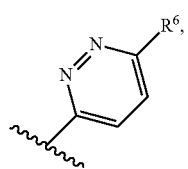 Y11
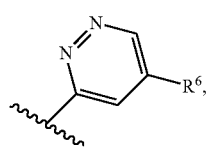 Y12
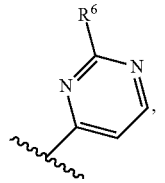 Y13
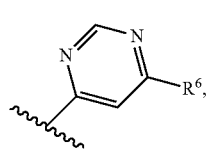 Y14
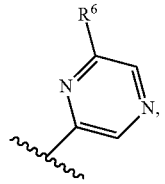 Y15
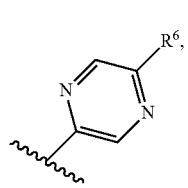 Y16
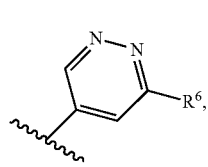 Y17

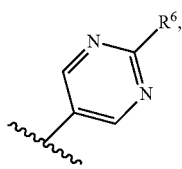
Y18

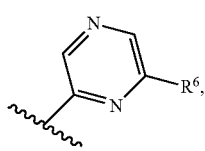
Y19

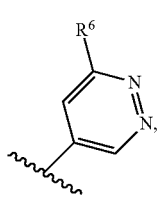
Y20

Y21

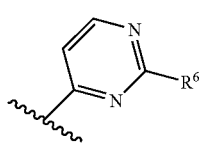
and

Y22 wherein R⁶ is as defined in claim 1.

3. The compound of claim 1, wherein $R^3$ is selected from the group consisting of halogen, —CN, and —ORb.

4. The compound of claim 2, wherein Y is selected from the group consisting of Y1 and Y2.

5. The compound of claim 2, wherein Y is selected from the group consisting of Y3, Y4, Y5, Y6, Y7, and Y8.

6. The compound of claim 2, wherein Y is selected from the group consisting of Y9, Y10, Y11, Y12, Y13, Y14, Y15, Y16, Y17, Y18, Y19, Y20, Y21, and Y22.

7. The compound of claim 1, wherein B is —CO—.

8. The compound of claim 1, wherein B is —SO₂—.

9. The compound of claim 1, wherein $R^7$ is selected from the group consisting of —$C_{1-4}$ alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, (5- to 10-membered)-$C_{1-9}$ heteroaryl, —$C_{1-4}$ alkyl-(5- to 10-membered)-$C_{1-9}$ heteroaryl, (5- to 10-membered)-$C_{1-9}$ heterocyclyl, and —$C_{1-4}$ alkyl-(5- to 10-membered)-$C_{1-9}$ heterocyclyl,
wherein said alkyl, cycloalkyl, alkylcycloalkyl, aryl, alkylaryl, heteroaryl, alkylheteroaryl, heterocyclyl, and alkylheterocyclyl groups being substituted with 1, 2, or 3 groups independently selected from the group consisting of halogen, hydroxy, —CN, —ORb, —SRb, —N(Rb)₂, —$C_{1-4}$alkyl optionally substituted with 1, 2, or 3 halogen atoms, optionally substituted —$C_{6-10}$ aryl, optionally substituted (5- to 10-membered)-$C_{1-9}$ heteroaryl, and (5- to 10-membered)-$C_{1-9}$ heterocyclyl; said cycloalkyl, alkylcycloalkyl, aryl, alkylaryl, heteroaryl, alkylheteroaryl, heterocyclyl, and alkylheterocyclyl is fused to a further (second) ring.

10. The compound of claim 1, wherein $R^7$ is —$C_{1-4}$ alkyl, wherein said alkyl is substituted with 1, 2, or 3 groups each independently selected from the group consisting of halogen, hydroxy, —CN, —ORb, —SRb, —N(Rb)₂, —$C_{1-4}$ alkyl optionally substituted with 1, 2, or 3 halogen atoms, optionally substituted —$C_{6-10}$ aryl, optionally substituted (5- to 10-membered)-$C_{1-9}$ heteroaryl, and (5- to 10-membered)-$C_{1-9}$ heterocyclyl; said aryl, heteroaryl, and heterocyclyl optionally fused to a further (second) ring.

11. The compound of claim 1, wherein $R^7$ is selected from the group consisting of —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, (5- to 10-membered)-$C_{1-9}$ heteroaryl, —$C_{1-4}$ alkyl-(5- to 10-membered)-$C_{1-9}$ heteroaryl, (5- to 10-membered)-$C_{1-9}$ heterocyclyl, and —$C_{1-4}$ alkyl-(5- to 10-membered)-$C_{1-9}$ heterocyclyl, wherein said cycloalkyl, alkylcycloalkyl, aryl, alkylaryl, heteroaryl, alkylheteroaryl, heterocyclyl, and alkylheterocyclyl is fused to a further (second) ring.

12. The compound of claim 1, wherein $R^7$ is selected from the group consisting of —$C_{1-4}$ alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, (5- to 10-membered)-$C_{1-9}$ heteroaryl, —$C_{1-4}$ alkyl-(5- to 10-membered)-$C_{1-9}$ heteroaryl, (5- to 10-membered)-$C_{1-9}$ heterocyclyl, and —$C_{1-4}$ alkyl-(5- to 10-membered)-$C_{1-9}$ heterocyclyl.

13. The compound of claim 1 selected from the group consisting of:
3-((7-chloroisoquinolin-1-yl)amino)-N-(1-methyl-1H-benzo[d][1,2,3]triazol-5-yl)benzamide;
3-((7-chloroisoquinolin-1-yl)amino)-N-(2-morpholino-2-(pyridin-2-yl)ethyl)benzamide;
3-((7-chloroisoquinolin-1-yl)amino)-N-((2,3-dihydrobenzo[b][1,4]dioxin-6-yl)methyl)benzamide;
N-benzyl-3-((7-chloroisoquinolin-1-yl)amino)benzamide;
4-((7-chloroisoquinolin-1-yl)amino)-N-((2,3-dihydrobenzo[b][1,4]dioxin-6-yl)methyl)benzamide;
4-((7-chloroisoquinolin-1-yl)amino)-N-(2-(pyridin-3-yl)-2-(pyrrolidin-1-yl)ethyl)benzamide;
4-((7-chloroisoquinolin-1-yl)amino)-N-(2-(pyridin-3-yl)-2-(pyrrolidin-1-yl)ethyl)picolinamide;
4-((7-chloroisoquinolin-1-yl)amino)-N-((2,3-dihydrobenzo[b][1,4]dioxin-6-yl)methyl)picolinamide;
N-benzyl-4-((7-chloroisoquinolin-1-yl)amino)picolinamide;
4-((7-chloroisoquinolin-1-yl)amino)-N-(4-methoxybenzyl)picolinamide;
4-((7-chloroisoquinolin-1-yl)amino)-N-(3-methoxybenzyl)picolinamide;
4-((7-chloroisoquinolin-1-yl)amino)-N-(3,4-dimethoxybenzyl)picolinamide;
N-(benzo[c][1,2,5]thiadiazol-5-ylmethyl)-4-((7-chloroisoquinolin-1-yl)amino)picolinamide;
4-((7-chloroisoquinolin-1-yl)amino)-N-(1,2,3,4-tetrahydronaphthalen-2-yl)picolinamide;
4-((7-chloroisoquinolin-1-yl)amino)-N-((3,4-dihydro-2H-benzo[b][1,4]dioxepin-7-yl)methyl)picolinamide;
4-((7-chloroisoquinolin-1-yl)amino)-N-((2,3-dihydrobenzofuran-5-yl)methyl)picolinamide;
N-(benzo[d][1,3]dioxol-5-ylmethyl)-4-((7-chloroisoquinolin-1-yl)amino)picolinamide;
4-((7-chloroisoquinolin-1-yl)amino)-N-(2-(2,3-dihydrobenzo[b][1,4]dioxin-6-yl)ethyl)picolinamide;

4-((7-chloroisoquinolin-1-yl)amino)-N-(chroman-6-ylmethyl)picolinamide;
4-((7-chloroisoquinolin-1-yl)amino)-N-((1,2,3,4-tetrahydronaphthalen-2-yl)methyl)picolinamide;
4-((7-chloroisoquinolin-1-yl)amino)-N-((2,3-dihydrobenzo[b][1,4]dioxin-2-yl)methyl)picolinamide;
4-((7-chloroisoquinolin-1-yl)amino)-N-(pyridin-3-ylmethyl)picolinamide;
4-((7-chloroisoquinolin-1-yl)amino)-N-(pyridin-4-ylmethyl)picolinamide;
4-((7-methoxyisoquinolin-1-yl)amino)-N-(2-(pyridin-3-yl)-2-(pyrrolidin-1-yl)ethyl)picolinamide;
N-((2,3-dihydrobenzo[b][1,4]dioxin-6-yl)methyl)-4-((7-methoxyisoquinolin-1-yl)amino)picolinamide;
N-benzyl-4-((7-methoxyisoquinolin-1-yl)amino)picolinamide;
5-((7-chloroisoquinolin-1-yl)amino)-N-(2-(pyridin-3-yl)-2-(pyrrolidin-1-yl)ethyl)picolinamide;
5-((7-chloroisoquinolin-1-yl)amino)-N-((2,3-dihydrobenzo[b][1,4]dioxin-6-yl)methyl)picolinamide;
N-benzyl-5-((7-chloroisoquinolin-1-yl)amino)picolinamide;
5-((7-chloroisoquinolin-1-yl)amino)-N-(4-methoxybenzyl)picolinamide;
5-((7-chloroisoquinolin-1-yl)amino)-N-(3-methoxybenzyl)picolinamide;
5-((7-chloroisoquinolin-1-yl)amino)-N-(3,4-dimethoxybenzyl)picolinamide;
N-(benzo[c][1,2,5]thiadiazol-5-ylmethyl)-5-((7-chloroisoquinolin-1-yl)amino)picolinamide;
5-((7-chloroisoquinolin-1-yl)amino)-N-(1,2,3,4-tetrahydronaphthalen-2-yl)picolinamide;
5-((7-chloroisoquinolin-1-yl)amino)-N-((3,4-dihydro-2H-benzo[b][1,4]dioxepin-7-yl)methyl)picolinamide;
5-((7-chloroisoquinolin-1-yl)amino)-N-((2,3-dihydrobenzofuran-5-yl)methyl)picolinamide;
N-(benzo[d][1,3]dioxol-5-ylmethyl)-5-((7-chloroisoquinolin-1-yl)amino)picolinamide;
5-((7-chloroisoquinolin-1-yl)amino)-N-(2-(2,3-dihydrobenzo[b][1,4]dioxin-6-yl)ethyl)picolinamide;
5-((7-chloroisoquinolin-1-yl)amino)-N-(chroman-6-ylmethyl)picolinamide;
5-((7-chloroisoquinolin-1-yl)amino)-N-(6-methoxy-1,2,3,4-tetrahydronaphthalen-2-yl)picolinamide;
5-((7-chloroisoquinolin-1-yl)amino)-N-((1,2,3,4-tetrahydronaphthalen-2-yl)methyl)picolinamide;
5-((7-chloroisoquinolin-1-yl)amino)-N-((2,3-dihydrobenzo[b][1,4]dioxin-2-yl)methyl)picolinamide;
5-((7-chloroisoquinolin-1-yl)amino)-N-(pyridin-3-ylmethyl)picolinamide;
5-((7-chloroisoquinolin-1-yl)amino)-N-(pyridin-4-ylmethyl)picolinamide;
5-((7-methoxyisoquinolin-1-yl)amino)-N-(1,2,3,4-tetrahydronaphthalen-2-yl)picolinamide;
N-(6-methoxy-1,2,3,4-tetrahydronaphthalen-2-yl)-5-((7-methoxyisoquinolin-1-yl)amino)picolinamide;
5-((7-methoxyisoquinolin-1-yl)amino)-N-((1,2,3,4-tetrahydronaphthalen-2-yl)methyl)picolinamide;
5-((7-cyanoisoquinolin-1-yl)amino)-N-(1,2,3,4-tetrahydronaphthalen-2-yl)picolinamide;
5-((7-cyanoisoquinolin-1-yl)amino)-N-(pyridin-3-ylmethyl)picolinamide;
N-(benzo[c][1,2,5]thiadiazol-5-ylmethyl)-5-((7-cyanoisoquinolin-1-yl)amino)picolinamide;
5-((5-chloroisoquinolin-1-yl)amino)-N-(1,2,3,4-tetrahydronaphthalen-2-yl)picolinamide;
5-((5-chloroisoquinolin-1-yl)amino)-N-((2,3-dihydrobenzofuran-5-yl)methyl)picolinamide;
6-((7-chloroisoquinolin-1-yl)amino)-N-(2-(pyridin-3-yl)-2-(pyrrolidin-1-yl)ethyl)nicotinamide;
6-((7-chloroisoquinolin-1-yl)amino)-N-((2,3-dihydrobenzo[b][1,4]dioxin-6-yl)methyl)nicotinamide;
N-benzyl-6-((7-chloroisoquinolin-1-yl)amino)nicotinamide;
6-((7-chloroisoquinolin-1-yl)amino)-N-(4-methoxybenzyl)nicotinamide;
6-((7-chloroisoquinolin-1-yl)amino)-N-(3-methoxybenzyl)nicotinamide;
6-((7-chloroisoquinolin-1-yl)amino)-N-(3,4-dimethoxybenzyl)nicotinamide;
N-(benzo[c][1,2,5]thiadiazol-5-ylmethyl)-6-((7-chloroisoquinolin-1-yl)amino)nicotinamide;
6-((7-chloroisoquinolin-1-yl)amino)-N-(1,2,3,4-tetrahydronaphthalen-2-yl)nicotinamide;
6-((7-chloroisoquinolin-1-yl)amino)-N-((3,4-dihydro-2H-benzo[b][1,4]dioxepin-7-yl)methyl)nicotinamide;
N-(benzo[d][1,3]dioxol-5-ylmethyl)-6-((7-chloroisoquinolin-1-yl)amino)nicotinamide;
6-((7-chloroisoquinolin-1-yl)amino)-N-(chroman-6-ylmethyl)nicotinamide;
5-((7-methoxyisoquinolin-1-yl)amino)-N-(pyridin-3-ylmethyl)picolinamide;
3-((7-chloroisoquinolin-1-yl)amino)-N-(2-(pyridin-3-yl)-2-(pyrrolidin-1-yl)ethyl)benzenesulfonamide;
3-((7-chloroisoquinolin-1-yl)amino)-N-(2-morpholino-2-(pyridin-2-yl)ethyl)benzenesulfonamide;
3-(7-chloroisoquinolin-1-yl)amino)-N-(1-methyl-1H-benzo[d][1,2,3]triazol-4-yl)benzenesulfonamide;
N-benzyl-3-((7-chloroisoquinolin-1-yl)amino)benzenesulfonamide;
3-((7-chloroisoquinolin-1-yl)amino)-N-((2,3-dihydrobenzo[b][1,4]dioxin-6-yl)methyl)benzenesulfonamide;
3-((7-chloroisoquinolin-1-yl)amino)-N-(1,2,3,4-tetrahydronaphthalen-2-yl)benzenesulfonamide;
3-(7-chloroisoquinolin-1-yl)amino)-N-((1-methyl-1H-benzo[d][1,2,3]triazol-5-yl)methyl)benzenesulfonamide;
4-((7-chloroisoquinolin-1-yl)amino)-N-(2-morpholino-2-(pyridin-2-yl)ethyl)benzenesulfonamide;
4-((7-chloroisoquinolin-1-yl)amino)-N-(1-methyl-1H-benzo[d][1,2,3]triazol-4-yl)benzenesulfonamide;
N-(benzo[c][1,2,5]thiadiazol-5-ylmethyl)-3-((7-chloroisoquinolin-1-yl)amino)benzenesulfonamide;
4-((7-chloroisoquinolin-1-yl)amino)-N-((2,3-dihydrobenzo[b][1,4]dioxin-6-yl)methyl)benzenesulfonamide;
N-(benzo[c][1,2,5]thiadiazol-5-ylmethyl)-4-((7-chloroisoquinolin-1-yl)amino)benzenesulfonamide;
4-((7-chloroisoquinolin-1-yl)amino)-N-(1,2,3,4-tetrahydronaphthalen-2-yl)benzenesulfonamide;
4-((7-chloroisoquinolin-1-yl)amino)-N-((1,2,3,4-tetrahydronaphthalen-2-yl)methyl)benzenesulfonamide;
4-((7-chloroisoquinolin-1-yl)amino)-N-((2,3-dihydrobenzo[b][1,4]dioxin-2-yl)methyl)benzenesulfonamide; and
N-benzyl-4-((7-chloroisoquinolin-1-yl)amino)benzenesulfonamide;
or a salt or solvate thereof.

14. A pharmaceutical composition, comprising a compound of claim 1, or a pharmaceutically acceptable salt or solvate thereof, and at least one pharmaceutically acceptable excipient.

15. A method of treating or preventing a condition associated with the alteration of the activity of GLB1 in a patient, comprising administering to the patient in need thereof an effective amount of a compound as defined in claim 1, or a pharmaceutically acceptable salt or solvate thereof.

16. A method of treating GM1 gangliosidosis or Morquio B syndrome in a patient, comprising administering to the patient in need thereof an effective amount of a compound as defined in claim 1, or a pharmaceutically acceptable salt or solvate thereof.

17. A method of increasing β-galactosidase activity in a patient in need thereof, comprising administering to the patient an effective amount of a compound as defined in claim 1, or a pharmaceutically acceptable salt or solvate thereof.

18. The method of claim 16, further comprising administering to the patient an effective amount of an enzyme for enzyme replacement therapy.

19. The method of claim 18, wherein the enzyme is β-galactosidase or an analog thereof.

20. The method of claim 16, further comprising administering to the patient a small molecule chaperone.

21. The method of claim 20, wherein the small molecule chaperone binds competitively to an enzyme.

22. The method of claim 20 or 21, wherein the small molecule chaperone is selected from the group consisting of iminoalditols, iminosugars, aminosugars, thiophenylglycosides, glycosidase, sulfatase, glycosyl transferase, phosphatase, and peptidase inhibitors.

23. The method of claim 22, wherein the small molecule chaperone is selected from the group consisting of 1-deoxygalactonojirimycin (DGJ), N-nonyldeoxynojirimycin (NN-DNJ), N-butyldeoxygalactonojirimycin (NB-DGJ), galactose, fluorous iminoalditol, and epi-isofagomine.

* * * * *